(12) United States Patent
Zimmer et al.

(10) Patent No.: US 11,285,219 B2
(45) Date of Patent: Mar. 29, 2022

(54) PEPTIDE-OLIGOUREA HYBRID COMPOUNDS

(71) Applicants: UREKA SARL, Mulhouse (FR); CENTRE NATIONAL DE LA RECHERCHE SCIENTIFIQUE (CNRS), Paris (FR)

(72) Inventors: Robert H. Zimmer, Mulhouse (FR); Gilles Guichard, Gradignan (FR); Juliette Fremaux, Pessac (FR); Sebastien Goudreau, Bordeaux (FR); Claire Venin, Villenave d'Ornon (FR); Laura Mauran, Gradignan (FR)

(73) Assignees: UREKA SARL, Mulhouse (FR); Centre National de la Recherche Scientifique (CNRS), Paris (FR)

(*) Notice: Subject to any disclaimer, the term of this patent is extended or adjusted under 35 U.S.C. 154(b) by 26 days.

(21) Appl. No.: 16/745,041

(22) Filed: Jan. 16, 2020

(65) Prior Publication Data
US 2020/0230249 A1 Jul. 23, 2020

Related U.S. Application Data

(60) Provisional application No. 62/794,014, filed on Jan. 18, 2019.

(51) Int. Cl.
| | |
|---|---|
| *A61K 47/59* | (2017.01) |
| *A61P 3/00* | (2006.01) |
| *C07K 7/02* | (2006.01) |
| *C07K 14/605* | (2006.01) |
| *A61K 38/00* | (2006.01) |

(52) U.S. Cl.
CPC ............ *A61K 47/59* (2017.08); *A61P 3/00* (2018.01); *C07K 7/02* (2013.01); *C07K 14/605* (2013.01); *A61K 38/00* (2013.01)

(58) Field of Classification Search
None
See application file for complete search history.

(56) References Cited

U.S. PATENT DOCUMENTS

| 5,424,286 A | 6/1995 | Eng |
| 2002/0143191 A1 | 10/2002 | Guichard et al. |
| 2005/0038105 A1 | 2/2005 | Guichard et al. |
| 2006/0211625 A1 | 9/2006 | Violette et al. |
| 2011/0117599 A1 | 5/2011 | Santer et al. |
| 2012/0329708 A1 | 12/2012 | Dimarchi et al. |
| 2015/0141323 A1 | 5/2015 | Ureka |
| 2016/0368864 A1 | 12/2016 | Goudreau et al. |
| 2017/0298112 A1 | 11/2017 | Zimmer et al. |
| 2018/0244718 A1 | 8/2018 | Guichard et al. |
| 2019/0002519 A1 | 1/2019 | Zimmer et al. |
| 2019/0142905 A1 | 5/2019 | Zimmer et al. |

FOREIGN PATENT DOCUMENTS

| JP | 2009-525744 A1 | 7/2009 |
| WO | WO 2006/086769 | 8/2006 |
| WO | WO 2010/080578 | 7/2010 |
| WO | WO 2013/102209 | 7/2013 |
| WO | WO 2017/037142 | 3/2017 |
| WO | WO 2017/037150 | 3/2017 |

OTHER PUBLICATIONS

Wiszniewska et al. "Synthesis of peptidomimetics: An evaluation of p-nitrophenyl carbamate of ethylenediamine," Letters in Peptide Science, 10: 33-39, 2003 (Year: 2003).*
Collie, Gavin W., et al., "Shaping quaternary assemblies of water-soluable non-peptide helical goldamers by sequence manipulation", Nature Chemistry, vol. 7, No. 11, Sep. 28, 2015, pp. 871-878.
Internatonal Search Report and Written Opinion for PCT/EP2020/050880, dated Mar. 13, 2020.
Fremaux, Juliette, et al., Peptide-oligourea hybrids analogue of GLP-1 with improved action in vivo, Nature Communications, vol. 10, No. 1, p. 924, Feb. 25, 2019 XP002796842, ISSN: 2041-1723.
Adelhorst, K., Hedegaard, B. B., Knudsen, L. B. & Kirk, O. Structure-activity studies of glucagon-like peptide-1. J. Biol. Chem. 269, 6275-6278 (Mar. 4, 1994).
Aisenbrey, C., et al., "Solid state NMR studies of oligourea foldamers: interaction of 15N-labelled amphiphilic helices with oriented lipid membanes", Org. Biomol. Chem., 10, 1440-1447 (2012) (Oct. 27, 2011).
Armstrong, M. J. et al. Liraglutide safety and efficacy in patients with non-alcoholic steatohepatitis (LEAN): a multicentre, double-blind, randomised, placebo-controlled phase 2 study. Lancet 387, 679-690, doi:10.1016/S0140-6736(15)00803-X (Feb. 13, 2016).
Azzarito, V., Long, K., Murphy, N. S. & Wilson, A. J. Inhibition of [alpha]-helix-mediated protein-protein interactions using designed molecules. Nat Chem 5, 161-173 (Mar. 2013).
Bain, S. C. et al. Cardiovascular safety of oral semaglutide in patients with type 2 diabetes: Rationale, design and patient baseline characteristics for the PIONEER 6 trial. Diabetes Obes. Metab. (2018) doi:10.1111/dom.13553 (Mar. 2019).
Boeijen, A., et al., "Solid-Phase Synthesis of oligourea peptidomimetics employing the Fmoc protection strategy", J. Org. Chem, 2001, 66, 8454-8462 (Nov. 17, 2001).
Boeijen, et al., "Solid-Phase Synthesis of Oligourea Peptidomimetics", Eur. J. Org. Chem., 1999, 2127-2135. (Aug. 12, 1999).

(Continued)

*Primary Examiner* — Christina Bradley

(74) *Attorney, Agent, or Firm* — Bryan D. Zerhusen, Esq.; Nicholas R. Herrel, Esq.; Cantor Colburn LLP

(57) ABSTRACT

The present description relates to peptidomimetic foldamers, and their synthesis. In particular, the description provides peptide-amino urea hybrid peptidomimetic foldamers comprising an alpha amino acid peptide portion and an oligourea portion.

11 Claims, 25 Drawing Sheets

Specification includes a Sequence Listing.

(56) References Cited

OTHER PUBLICATIONS

Buse, J. B. et al. Metabolic effects of two years of exenatide treatment on diabetes, obesity, and hepatic biomarkers in patients with type 2 diabetes: an interim analysis of data from the open-label, uncontrolled extension of three double-blind, placebo-controlled trials. Clin Ther 29, 139-153, doi:10.1016/j.clinthera.2007.01.015 (Jan. 2007).
Campbell, J. E. & Drucker, D. J. Pharmacology, Physiology, and Mechanisms of Incretin Hormone Action. Cell Metab. 17, 819-837 (Jun. 4, 2013).
Cheang, J. Y. & Moyle, P. M. Glucagon-Like Peptide-1 (GLP-I)-Based Therapeutics: Current Status and Future Opportunities beyond Type 2 Diabetes. ChemMedChem (2018), 13, 662-671 doi:10.1002/cmdc.201700781 (Apr. 6, 2018).
Chicchi, et al., "Alterations in receptor activation and divalent cation activation of agonist binding by deletion of intracellular domains of the glucagon receptor", J. Biol. Chem., 272: pp. 7765 (Mar. 21, 1997).
Cho, C., et al., "An unnatural Biopolymer", Science 1993, 261, 1303-1305 (Sep. 3, 1993).
Cho., C., et al., Synthesis and screening of linear and cyclic oligocarbamate libraries. Discovery of high affinity ligands for CPIIb/IIIa, J. Am. Chem. Soc. 1998, 120(31), 7706-7718 (Jul. 24, 1998).
Choi, Soo Hyuk, "Helical structures of unnatural peptides for biological applications", Biomedical Engineering Letters, vol. 3., No. 4, pp. 226-231, (Dec. 1, 2013).
Cusi, K. Nonalcoholic fatty liver disease in type 2 diabetes mellitus. Curr Opin Endocrinol Diabetes Obes 16, 141-149, doi:10.1097/MED.0b013e3283293015 (Apr. 2009).
Cuthbertson, D. J. et al. Improved glycaemia correlates with liver fat reduction in obese, type 2 diabetes, patients given glucagon-like peptide-1 (GLP-1) receptor agonists. PLoS One 7, e50117, doi:10.1371/journal.pone.0050117 (Dec. 6, 2012).
Degn, K. B. et al. One week's treatment with the long-acting glucagon-like peptide 1 derivative liraglutide (NN2211) markedly improves 24-h glycemia and alpha- and beta-cell function and reduces endogenous glucose release in patients with type 2 diabetes. Diabetes 53, 1187-1194 (May 2004).
Denton, E. V. et al. A β-Peptide Agonist of the GLP-1 Receptor, a Class B GPCR. Org. Lett. 15, 5318-5321 (Oct. 18, 2013).
Ding, X., Saxena, N. K., Lin, S., Gupta, N. A. & Anania, F. A. Exendin-4, a glucagon-like protein-1 (GLP-1) receptor agonist, reverses hepatic steatosis in ob/ob mice. Hepatology 43, 173-181, doi:10.1002/hep.21006 (Jan. 2006).
Douat-Casassus, et al., "Microwave-enhanced solid-phase synthesis of N,N'-linked aliphatic oligoureas and related hybrids", Org. Lett. 14, 3130-3133 (May 30, 2012).
Drucker, D. J. The biology of incretin hormones. Cell Metab 3, 153-165, doi:10.1016/j.cmet.2006.01.004 (Mar. 2006).
Drucker, D. The Cardiovascular Biology of Glucagon-like Peptide-1. Cell Metab. 24, 15-30 (Jul. 12, 2016).
Drucker, D.J., Mechanisms of Action and Therapeutic Application of Glucagon-like Peptide-1, Cell Metabolism Review, 27, 741-756 (Apr. 13, 2018).
Estieu-Gionnet, K. & Guichard, G. Stabilized helical peptides: overview of the technologies and therapeutic promises. Expert Opin. Drug Discov. 6, 937-963 (Sep. 2011).
Fischer Lucile, "Succinimidyl carbamate derivatives from N-protected alpha-amino acids and dipeptides-Synthesis of Ureidopeptides and Oligourea/Peptide Hybrids", European Journal of Organic Chemistry, No. 15:2511-2525, (May 1, 2007).
Fischer Lucile, et al., "Folding and self-assembly of aromatic and aliphatic urea oligomers: Towards connecting structure and function", Organic & Biomolecular Chemistry, 8(14):3101-3117, (Jan. 1, 2010).
Fischer, L., et al., "The canonical helix of urea oligomers at atomic resolution: insights into folding-induced axial organization", Angew. Chem. 2010, 122, 1085-1088 (Feb. 1, 2010).
Fosgerau, K. & Hoffmann, T. Peptide therapeutics: current status and future directions. Drug Discov. Today 20, 122-128 (Jan. 2015).
Fremaux, J. et al. "α-Peptide/Oligourea Chimeras: Stabilization of Short α-helices by Non Peptide Helical Foldamers", Angew. Chem. Int. Ed. Engl. , vol. 54, 2015, pp. 9816-9820 DOI: 10.1002/anie.201500901R201500901 (Jul. 1, 2015).
Fremaux, J., et al., "Influence of archiral unites with gem-dimethy substituents on the helical charater of aliphatic oligourea foldamers", Chem Comm (Camb). Aug. 28, 2013, 49(67); 7415-7. Doi:10.1039/c3cc40961a (Jun. 21, 2013).
Fremaux, J., et al., G. "Condensation approach to aliphatic oligourea foldamers: helices with N-(pyrrolidin-2-ylmethyl)ureido junctions", Angew. Chem. Int. Ed Engl. 50, 11382-11385 (Oct. 4, 2011).
Gallwitz, B. et al. Structure/Activity Characterization of Glucagon-Like Peptide-1. FEBS J. 225, 1151-1156 (Nov. 1, 1994).
Gao, H. et al. The Glucagon-Like Peptide-1 Analogue Liraglutide Inhibits Oxidative Stress and Inflammatory Response in the Liver of Rats with Diet-Induced Non-alcoholic Fatty Liver Disease. Biol Pharm Bull 38, 694-702, doi:10.1248/bpb.b14-00505 (May 2015).
Gellman, et al., "Foldamers: A Manifesto", Acc. Chem. Res. 31, 173-180 (Mar. 13, 1998).
Goodman, et al., "Foldamers as versatile frameworks for the design and evolution of function", Nat. Chem Biol. 3, 252-262 (May 2007).
Gopalakrishnan, R., Frolov, A. I., Knerr, L., Drury, W. J. & Valeur, E. Therapeutic Potential of Foldamers: From Chemical Biology Tools To Drug Candidates? J. Med. Chem. 59, 9599-9621 (Nov. 10, 2016).
Gradišar, et al., "Design of a single-chain polypeptide tetrahedron assembled from coiled-coil segments", Nat. Chem. Biol. 9, 362-366 (Apr. 28, 2013).
Gradišar, et al., "Self-assembled bionanostructures: proteins following the lead of DNA nanostructures", J. Nanobiotechnology 12, 4, 1-9, (Feb. 3, 2014).
Guichard, et al., "Synthetic foldamers", Chem. Commun. 47, 5933-5941 (Apr. 11, 2011).
Guichard, G., et al., "Effective Preparation of O-succinimidyl-2(tert-butoxycarbonylamino) ethylcarbamate derivatives from B-amino Acids. Application to the synthesis of urea-containing pseudopeptides and oligoureas", J. Org. Chem. 1999, 64, 8702-8705 (Oct. 22, 1999).
Hager, M. V., Johnson, L. M., Wootten, D., Sexton, P. M. & Gellman, S. H. β-Arrestin-Biased Agonists of the GLP-1 Receptor from β-Amino Acid Residue Incorporation into GLP-1 Analogues. J. Am. Chem. Soc. 138, 14970-14979 (Nov. 4, 2016).
Hanna, A., Connelly, K. A., Josse, R. G. & McIntyre, R. S. The non-glycemic effects of incretin therapies on cardiovascular outcomes, cognitive function and bone health. Expert Rev. Endocrinol. Metab. 10, 101-114 (Jan. 2015).
Hemmerlin C et al: "Helix-forming oligoureas: Temperature-dependent NMR, structure determination, and circular dichroism of a nonamer with functionalized side chains", Helvetica Chimica Acta, Verlag Helvetica Chimica Acta, CH, vol. 85, No. 11, Jan. 1, 2002 (Jan. 1, 2002), pp. 3692-3711, XP002417783, ISSN: 0018-019X, DOI: 10.1002/1522-2675(200211)85:11<3692::AID-HLCA3692>3.0.00;2-W oligoureas 1 and 2 (Jan. 1, 2002).
Henninot, A., Collins, J. C. & Nuss, J. M. The Current State of Peptide Drug Discovery: Back to the Future? J. Med. Chem. 2018, 61, 1382-1414 (Aug. 11, 2018) doi: 10.1021/acs.jmedchem.7b00318.
Hupe-Sodmann, K. et al. Characterisation of the processing by human neutral endopeptidase 24.11 of GLP-1 (7-36) amide and comparison of the substrate specificity of the enzyme for other glucagon-like peptides. Regul. Pept. 58, 149-156 (Aug. 22, 1995).
Jazayeri, A. et al. Crystal structure of the GLP-1 receptor bound to a peptide agonist. Nature 546, 254-258 (May 31, 2017).
Jessen, L. et al. Suppression of Food Intake by Glucagon-Like Peptide-1 Receptor Agonists: Relative Potencies and Role of Dipeptidyl Peptidase-4. Endocrinology 153, 5735-5745 (Dec. 2012).

(56) References Cited

OTHER PUBLICATIONS

Johnson, L. M. et al. A Potent α/β-Peptide Analogue of GLP-1 with Prolonged Action in Vivo. J. Am. Chem. Soc. 136, 12848-12851 (Sep. 5, 2014).

Jouihan, H. et al. Superior reductions in hepatic steatosis and fibrosis with co-administration of a glucagon-like peptide-1 receptor agonist and obeticholic acid in mice. Mol Metab 6, 1360-1370, doi:10.1016/j.molmet.2017.09.001 (Sep. 14, 2017).

Kaspar, A. A. & Reichert, J. M. Future directions for peptide therapeutics development. Drug Discov. Today 18, 807-817 (Sep. 2013).

Kreymann, B., Williams, G., Ghatei, M. A. & Bloom, S. R. Glucagon-like peptide-1 7-36: a physiological incretin in man. Lancet 2, 1300-1304 (Dec. 1987).

Lau, J. et al. Discovery of the Once-Weekly Glucagon-Like Peptide-1 (GLP-1) Analogue Semaglutide. J. Med. Chem. 58, 7370-7380 (Sep. 11, 2015).

Legrand, B., et al., "Robust helix formation in a new family of oligoureas based on a constrained bicyclic building block", Angew. Chem. Int. Ed., 2012, 51, 11267-11270 (Nov. 5, 2012).

Liskamp, R. M. J., Rijkers, D. T. S., Kruijtzer, J. A. W. & Kemmink, J. Peptides and Proteins as a Continuing Exciting Source of Inspiration for Peptidomimetics. ChemBioChem 12, 1626-1653 (Jul. 25, 2011).

Lombardo, C.M., et al., "Anatomy of an oligourea six-helix bundle", Journal of the American Chemical Society, Aug. 24, 2016, vol. 138, No. 33, p. 10522-10530 (Jul. 19, 2016).

Madsbad, S. et al. An overview of once-weekly glucagon-like peptide-1 receptor agonists—available efficacy and safety data and perspectives for the future. Diabetes Obes Metab 13, 394-407, doi:10.1111 /j.1463-1326.2011.01357.x (May 2011).

Madsbad, S. Review of head-to-head comparisons of glucagon-like peptide-1 receptor agonists. Diabetes Obes. Metab. 18, 317-332 (Apr. 2016).

Madsbad, S. The role of glucagon-like peptide-1 impairment in obesity and potential therapeutic implications. Diabetes Obes. Metab. 16, 9-21 (Jan. 2014).

Martinek, T. A. & Fülöp, F. Peptidic foldamers: ramping up diversity. Chem Soc Rev 41, 687-702 (Jan. 21, 2012).

Mauran, L., Kauffmann, B., Odaert, B. & Guichard, G. Stabilization of an α-helix by short adjacent accessory foldamers. Comptes Rendus Chim. 19, 123-131 (Jan.-Feb. 2016).

Maury, J., Le Bailly, B. A. F., Raftery, J. & Clayden, J. Conformational cooperativity between helical domains of differing geometry in oligoamide-oligourea foldamer chimeras. Chem Commun 51, 11802-11805 (Jul. 28, 2015).

McBrayer, D. N. & Tal-Gan, Y. Recent Advances in GLP-1 Receptor Agonists for Use in Diabetes Mellitus. Drug Dev Res 78, 292-299, doi:10.1002/ddr.21404 (Sep. 2017).

Miranda, L. P. et al. Design and Synthesis of Conformationally Constrained Glucagon-Like Peptide-1 Derivatives with Increased Plasma Stability and Prolonged in Vivo Activity. J. Med. Chem. 51, 2758-2765 (May 8, 2008).

Murage, E. N., Gao, G., Bisello, A. & Ahn, J.-M. Development of Potent Glucagon-like Peptide-1 Agonists with High Enzyme Stability via Introduction of Multiple Lactam Bridges. J. Med. Chem. 53, 6412-6420 (Aug. 5, 2010).

Nakade, Y., Tsukamoto, K., Iwa, M., Pappas, T. N. & Takahashi, T. Glucagon like peptide-1 accelerates colonic transit via central CRF and peripheral vagal pathways in conscious rats. Auton Neurosci 131, 50-56, doi: 10.1016/j.autneu.2006.06.007 (Jan. 30, 2007).

Nauck, M. A. et al. Efficacy and safety of the dipeptidyl peptidase-4 inhibitor, sitagliptin, compared with the sulfonylurea, glipizide, in patients with type 2 diabetes inadequately controlled on metformin alone: a randomized, double-blind, non-inferiority trial. Diabetes Obes Metab 9, 194-205, doi:10.1111/j.1463-1326.2006.00704.x (Mar. 2007).

Nauck, M. A. et al. Five weeks of treatment with the GLP-1 analogue liraglutide improves glycaemic control and lowers body weight in subjects with type 2 diabetes. Exp Clin Endocrinol Diabetes 114, 417-423, doi:10.1055/s-2006-924230 (Sep. 2006).

Nelli, et al., "Structural characterization of short hybrid urea/carbamate (U/C) foldamers: a case of partial helix unwinding", Biopolymers 100, 687-697 (Jul. 26, 2013).

Nelli, Y. R.; "Isosteric Substitutions of Urea to Thiourea and Selenourea in Aliphatic Oligourea Foldamers: Site-Specific Perturbation of the Helix Geometry", Chem. Eur. J. 2015, 21, 2870-2880. (Dec. 21, 2004).

Nelli, Y.R., et al., "An activated building block for the introduction of the histidine side chain in aliphatic oligourea foldamers", Tetrahedron, 2012, 68, 4492-4500 (Jun. 10, 2012).

Pasco, M., Dolain, C. & Guichard, G. Foldamers in Medicinal Chemistry, in Comprehensive Supramolecular Chemistry II 89-125 (Elsevier, 2017) (Nov. 2019) doi :10.1016/B978-0-12-409547-2.12565-X.

Patch, et al., "Mimicry of bioactive peptides via non-natural, sequence-specific peptidomimetic oligomers", Curr. Op. Chem. Bio., 2002, 6, 872-877 (Nov. 2002).

Pendem, N. et al., "Controlling Helix Formation in the γ-Peptide Superfamily: Heterogeneous Foldamers with Urea/Amide and Urea/Carbamate Backbones", Angew. Chem. Int. Ed. 2013, 52, 4147-4151. (Apr. 8, 2013).

Pendem, N.; et al., "Helix-Forming Propensity of Aliphatic Urea Oligomers Incorporating Noncanonical Residue Substitution Patterns", J. Am. Chem. Soc. 2013, 135, 4884-4892. (Feb. 27, 2013).

Potts, J. E. et al. The Effect of Glucagon-Like Peptide 1 Receptor Agonists on Weight Loss in Type 2 Diabetes: A Systematic Review and Mixed Treatment Comparison Meta-Analysis. PLOS ONE 10, e0126769 (Jun. 29, 2015).

Rose, K., et al., "Insulin proteinase liberates from glucagon a fragment known to have enhanced activity against Ca2++AMg2+-dependent ATPase", (1988) Biochemical Journal, vol. 256, pp. 847-851 (Dec. 15, 1988).

Runge, et al., "Different domains of the glucagon and glucagon-like peptide-1 receptors provide the critical determinants of ligand selectivity", Brit. J. Pharmacol., 138: pp. 787-794 (Mar. 2003).

Runge, S., Thøgersen, H., Madsen, K., Lau, J. & Rudolph, R. Crystal Structure of the Ligand-bound Glucagon-like Peptide-1 Receptor Extracellular Domain. J. Biol. Chem. 283, 11340-11347 (Apr. 25, 2008).

Sathyanarayana, P. et al. Effects of combined exenatide and pioglitazone therapy on hepatic fat content in type 2 diabetes. Obesity (Silver Spring) 19, 2310-2315, doi:10.1038/oby.2011.152 (Dec. 2011).

Semetey, V., et al., "Stable helical secondary structure in short-chain N,N-Linked oligoureas bearing proteininogenic side chains", Angew. Chem. Int. Ed., 41,1893-1895 (May 28, 2002).

Sharma, S., Mells, J. E., Fu, P. P., Saxena, N. K. & Anania, F. A. GLP-1 analogs reduce hepatocyte steatosis and improve survival by enhancing the unfolded protein response and promoting macroautophagy. PLoS One 6, e25269, doi:10.1371/journal.pone.0025269 (Sep. 21, 2011).

Siegel et al. Comparison of the effect of native glucagon-like peptide 1 and dipeptidyl peptidase IV-resistant analogues on insulin release from rat pancreatic islets. Eur. J. Clin. Invest. 29, 610-614 (Jul. 1999).

Siegel, E. G. et al. Biological activity of GLP-1-analogues with N-terminal modifications. Regul. Pept. 79, 93-102 (Feb. 5, 1999).

Soth and Nowick, "A peptide/Oligourea/Azapeptide Hybrid That Adopts a Hairpin Turn", J. Org. Chem. 1999, 64, 276-281 (Dec. 19, 1998).

Takemoto, Y. "Recognition and activation by ureas and thioureas: stereoselective reactions using ureas and thioureas as hydrogen-bonding donors", Org. Biomol. Chem. 2005, 3, 4299-306. (Dec. 21, 2005).

Tamaki, C., et al., Pharmacological profile and clinical trial results of a long-acting, once weekly human GLP-1 receptor agonist Dulaglutide (Genetical Recombination), Folia Pharmacologica Japonica, 2015, vol. 146, pp. 215-224 (Oct. 2015) (No abstract or English version available—ENGLISH title only).

Tamilarasu, et al., "Targeting RNA with peptidomimetic oligomers in human cells", Biorg. Med. Chem. Let., 2001, 11, 505-7. (Mar. 2001).

(56) References Cited

OTHER PUBLICATIONS

Tamilarasu, "High Affinity and Specific Binding of HIV-1 TAR RNX by a Tat-Derived Oligourea", Journal of the American Chemical Society (1999), 121 (7), 1597-1598. (Feb. 4, 1999).
Tamilarasu, "Supporting Information—High Affinity and Specific Binding of HIV-1 TAR RNA by a Tat-Derived Oligourea", Journal of the American Chemical Society (1999), 121 (7), pp. S1-S12.
Tang-Christensen, M. & Cowley, M. A. GLP-1 analogs: satiety without malaise? Am J Physiol Regul Integr Comp Physiol 293, R981-982, doi:10.1152/ajpregu.00449.2007 (Sep. 1, 2007).
Teyssières, E. et al. Proteolytically Stable Foldamer Mimics of Host-Defense Peptides with Protective Activities in a Murine Model of Bacterial Infection. J. Med. Chem. 59, 8221-8232 (Aug. 16, 2016).
Townsend, S. A. & Newsome, P. N. Review article: new treatments in non-alcoholic fatty liver disease. Aliment Pharmacol Ther 46, 494-507, doi:10.1111/apt.14210 (Sep. 2017).
Trevaskis, J. L. et al. Glucagon-like peptide-1 receptor agonism improves metabolic, biochemical, and histopathological indices of nonalcoholic steatohepatitis in mice. Am J Physiol Gastrointest Liver Physiol 302, G762-772, doi:10.1152/ajpgi.00476.2011 (Apr. 15, 2012).
Tushuizen, M. E. et al. Incretin mimetics as a novel therapeutic option for hepatic steatosis. Liver Int 26, 1015-1017, doi: 10.1111/j.1478-3231.2006.01315.x (Sep. 2006).
Underwood, C. R. et al. Crystal Structure of Glucagon-like Peptide-1 in Complex with the Extracellular Domain of the Glucagon-like Peptide-1 Receptor. J. Biol. Chem. 285, 723-730 (Jan. 2010).
Valeur, E. et al. New Modalities for Challenging Targets in Drug Discovery. Angew. Chem. Int. Ed. 56, 10294-10323 (Aug. 21, 2017).
Vilsboll, T., Christensen, M., Junker, A. E., Knop, F. K. & Gluud, L. L. Effects of glucagon-like peptide-1 receptor agonists on weight loss: systematic review and meta-analyses of randomised controlled trials. BMJ 344, d7771, doi:10.1136/bmj.d7771 (Jan. 2012).
Violette, A., et al., "Exploring helical folding of oligoureas during chain elongation by high-resolution magic-angle-spinning (HRMAS) NMR spectroscopy", Chem. Eur. J. 2008, 14, 3874-3882 (Jan. 28, 2005).
Violette, et al., "N,N'-Linked Oligoureas as Foldamers: Chain Length Requirements for Helix Formation in Protic Solvent Investigated by Circular Dichroism, NMR Spectroscopy, and Molecular Dynamics", Journal of the American Chemical Society, vol. 127, No. 7, pp. 2156-2164, XP055152097, ISSN: 0002-7863, DOI: 10.1021/ja044392b (Jan. 2005).
Wang, X. C., Gusdon, A. M., Liu, H. & Qu, S. Effects of glucagon-like peptide-1 receptor agonists on non-alcoholic fatty liver disease and inflammation. World J Gastroenterol 20, 14821-14830, doi:10.3748/wjg.v20.i40.14821 (Oct. 2014).
Wechsel, Romina, et al., "Inducing archiral aliphatic oligoureas to fold into helical conformations", Chemical Communications, vol. 50, No. 95, Jan. 1, 2014, pp. 15006-15009 (Jan. 1, 2014).
Wiszniewska, et al., "p-Nitrophenoxycarbonyl derivatives of Boc-protected diaminoalkanes in the synthesis of encephalin peptidomimetics", J. Peptide Sci. 11:579-583 (Feb. 28, 2005).
Wu, et al., "Chloride Coordination by Oligoureas: From Mononuclear Crescents to Dinuclear Foldamers", Org. Lett. 2012, 14 (3), 684-687 (Jan. 12, 2012).
Xiao, Q. et al. Biological Activities of Glucagon-Like Peptide-1 Analogues in Vitro and in Vivo. Biochemistry 40, 2860-2869 (Mar. 2001).
Yang, X., et al., "Long-acting GLP-1 analogue in V-shaped conformation by terminal polylysine modifications", Molecular Pharmaceutics., vol. 11, No. 11, (2014), pp. 4092-4099 (Nov. 3, 2014).
Zhang, Y. et al. Cryo-EM structure of the activated GLP-1 receptor in complex with a G protein. Nature 546, 248-253 (Jun. 2017).
Miller, et al., The Class B G-Protein-Coupled GLP-1 receptor: an important target for the treatment of type-2 diabetes mellitus, International Journal of Obesity Supplements, vol. 4:S9-S13 (Year Jul. 2014).

* cited by examiner

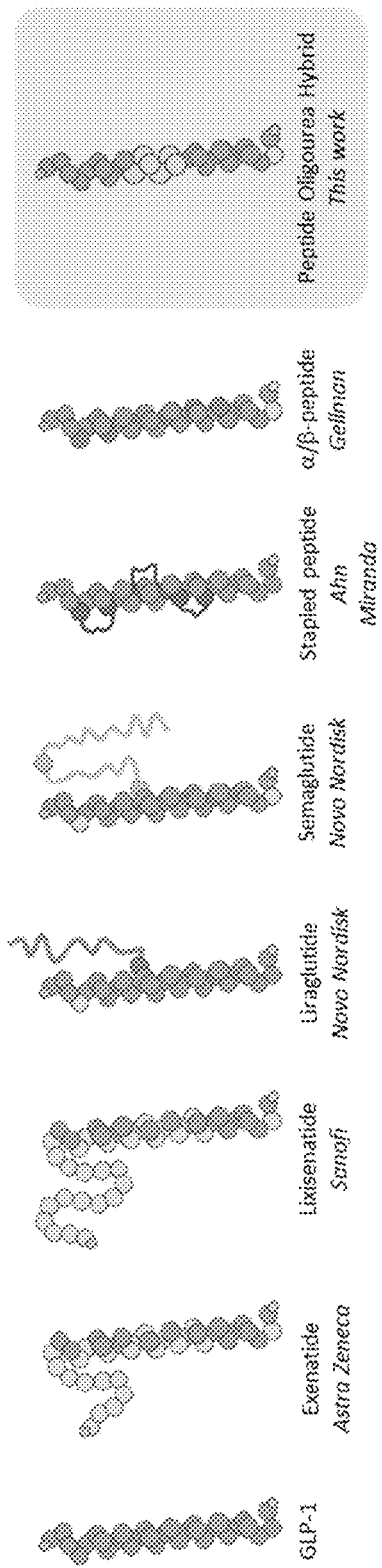
FIG. 1
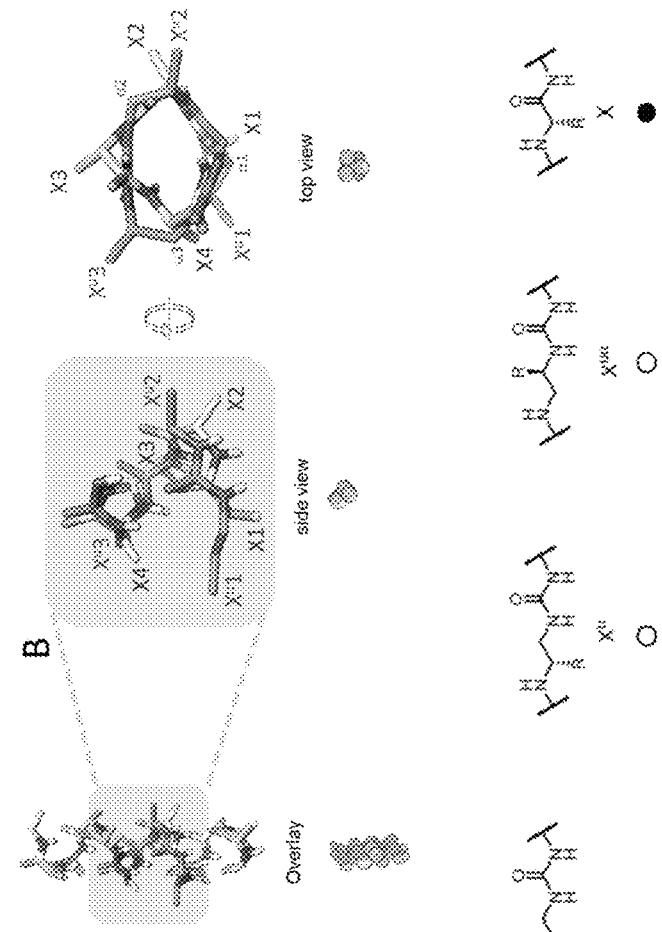
FIG. 2A
FIG. 2B
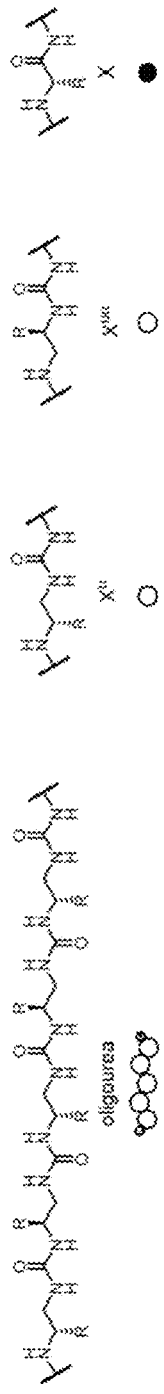
FIG. 2C

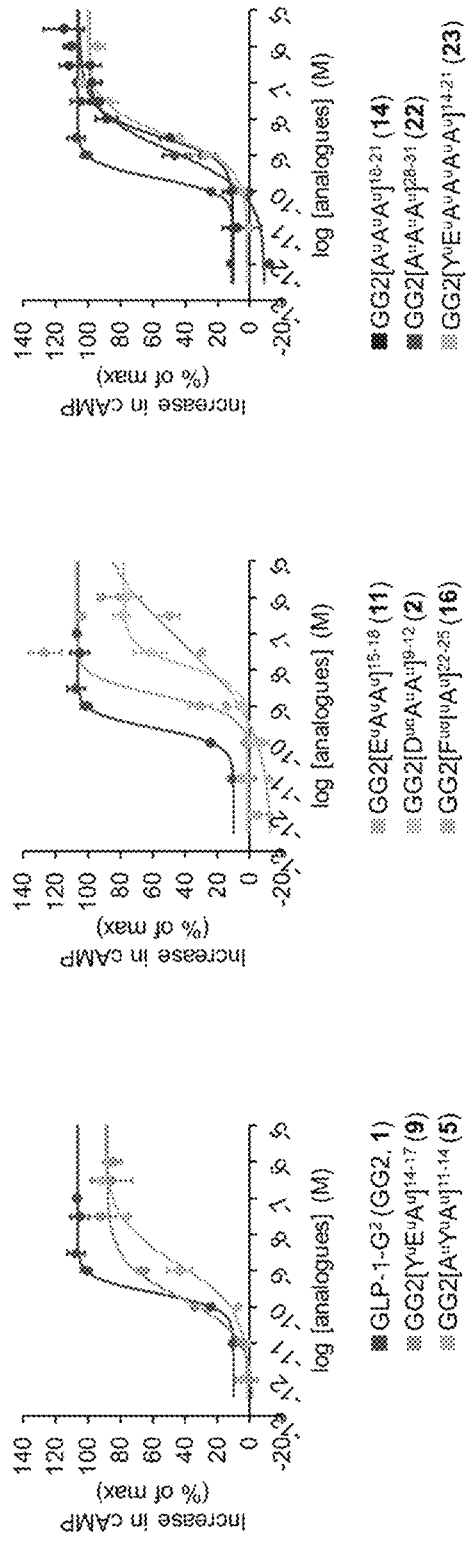
FIG. 3
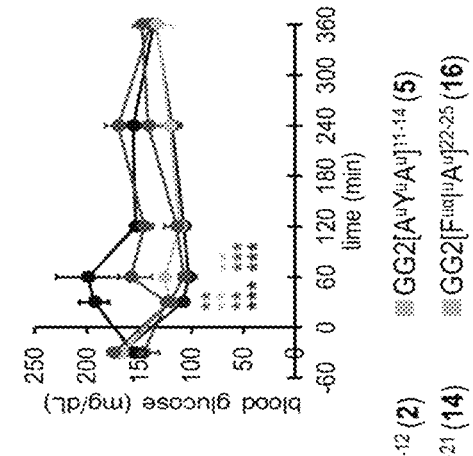
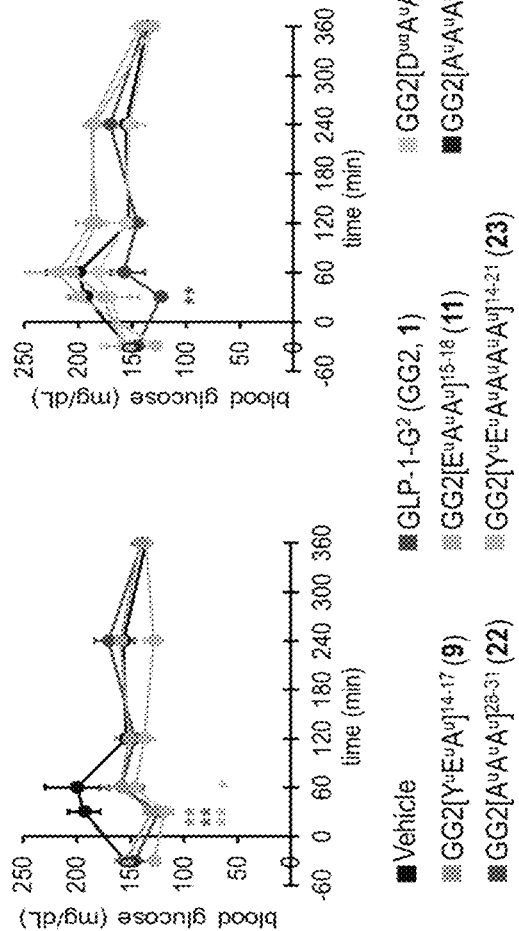
FIG. 4A
FIG. 4B
FIG. 4C

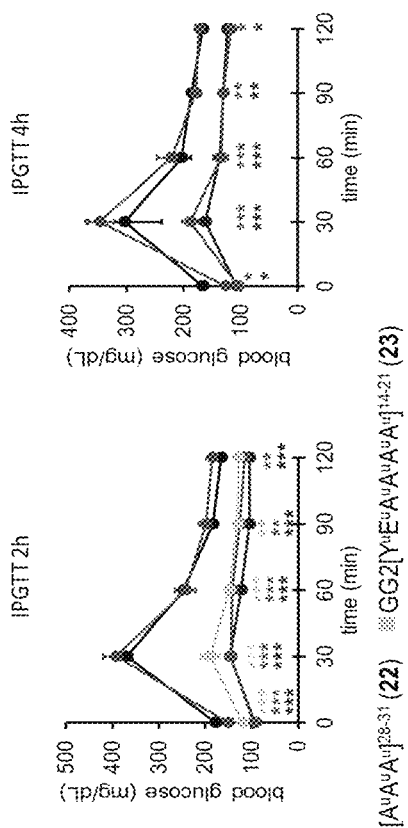
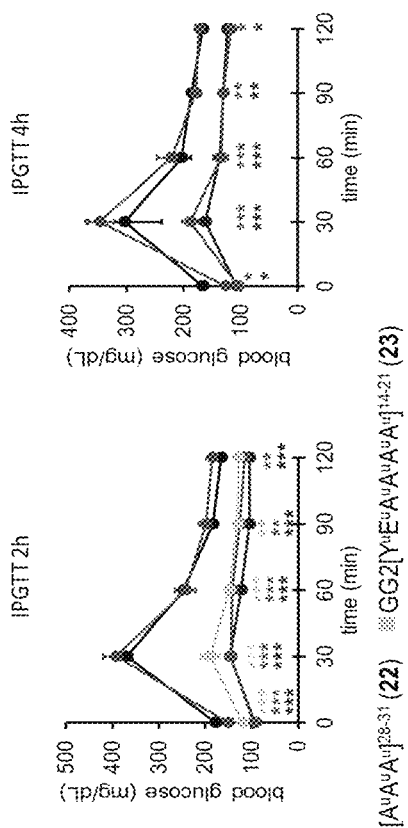
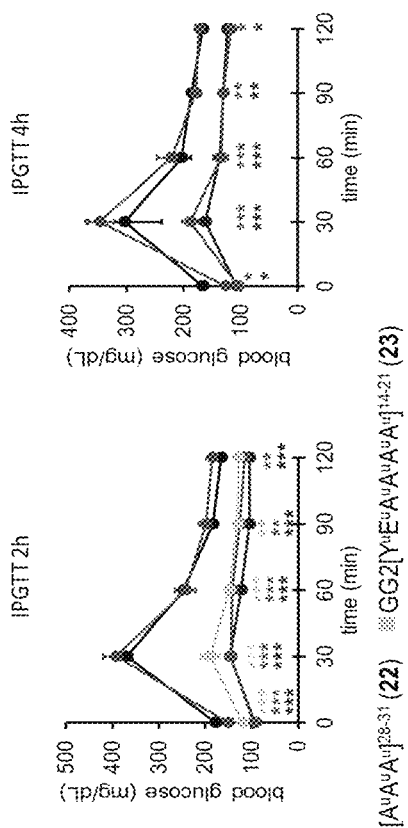
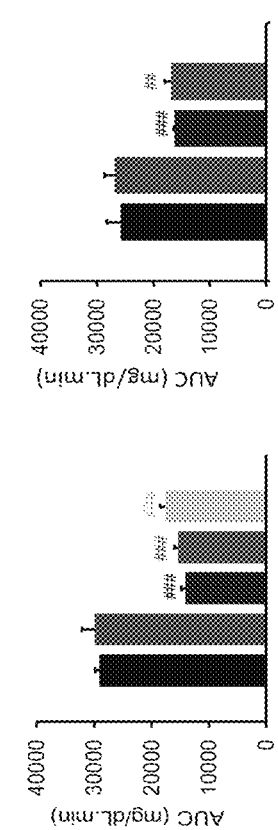
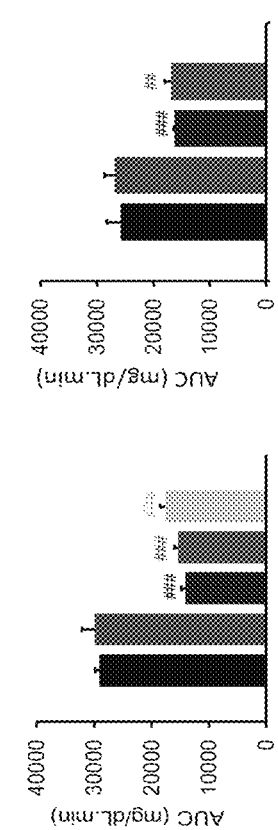
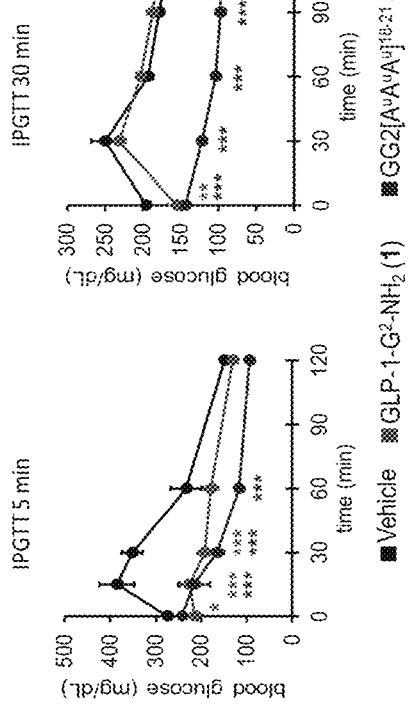
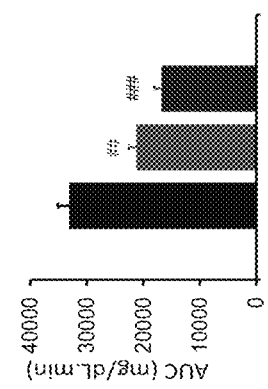

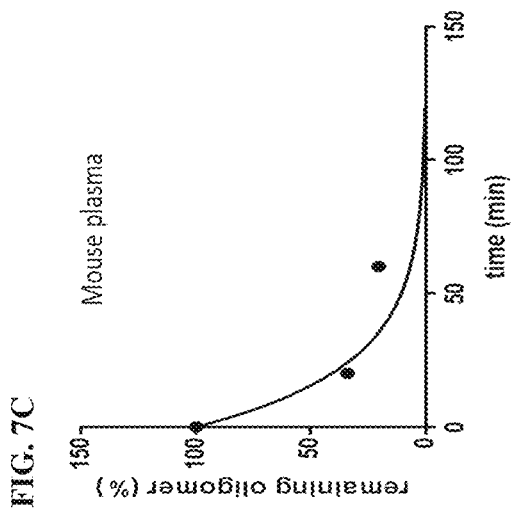
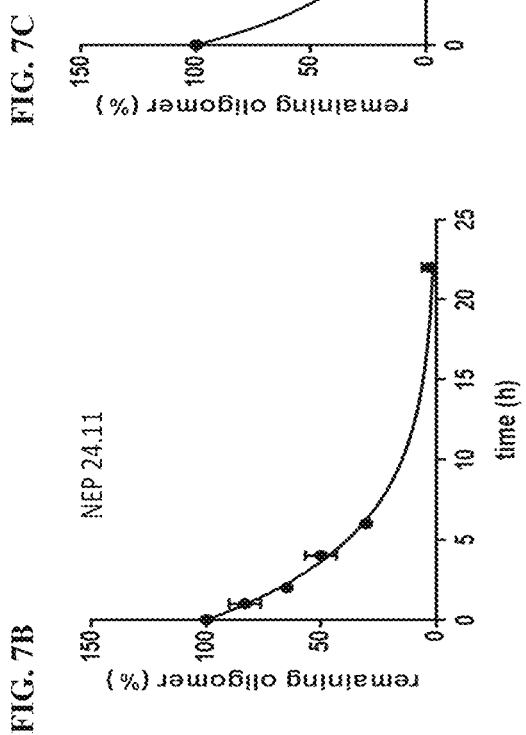
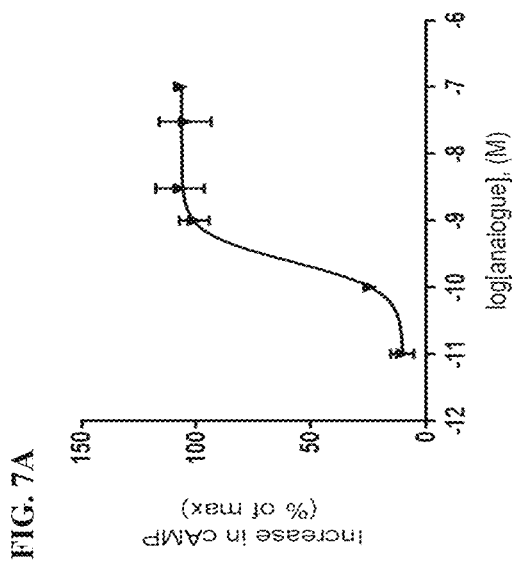
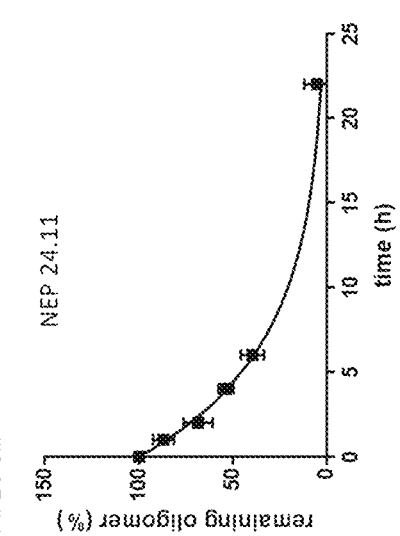
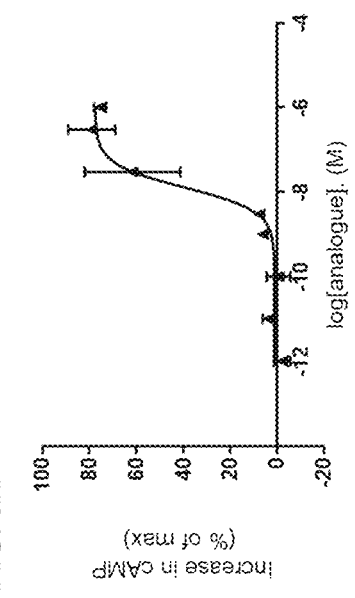

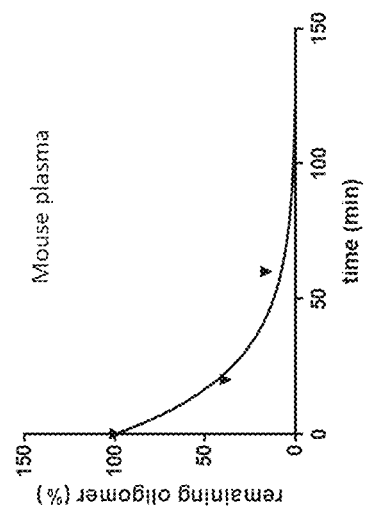
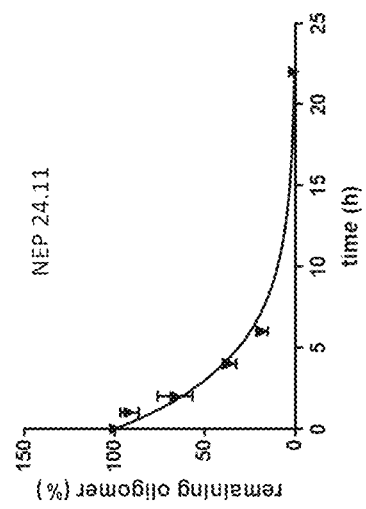
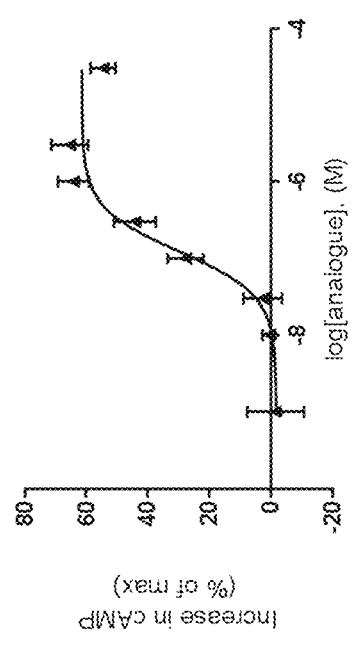
FIG. 15A
FIG. 15B
FIG. 15C
FIG. 16

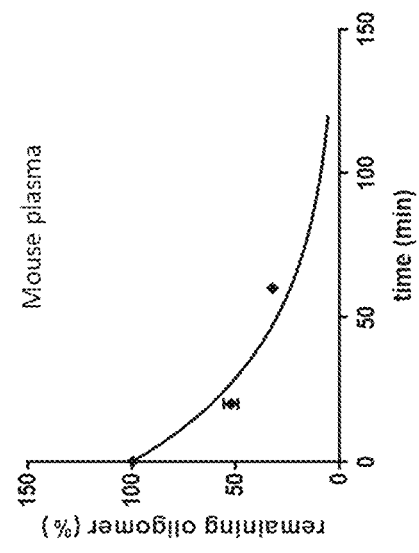
FIG. 17C
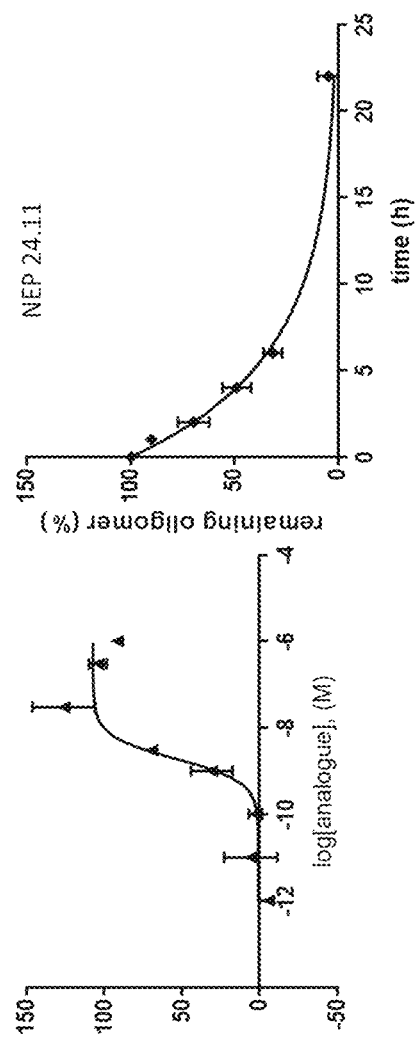
FIG. 17B
FIG. 17A
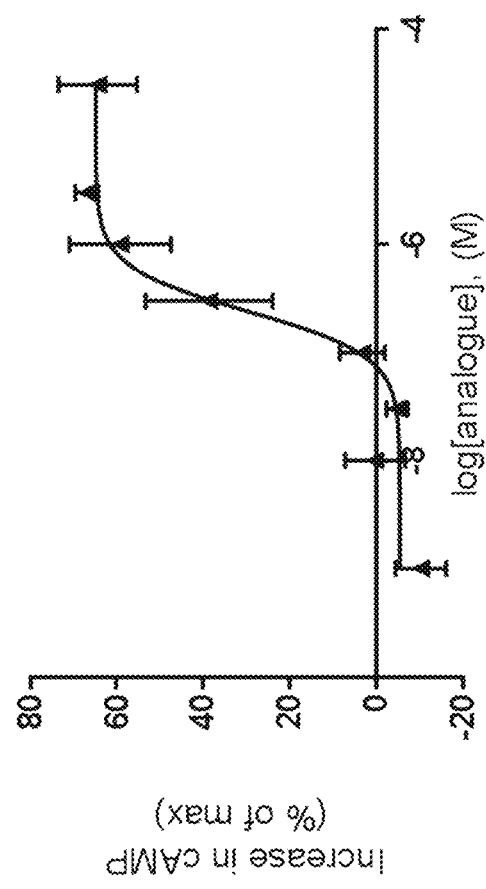
FIG. 18

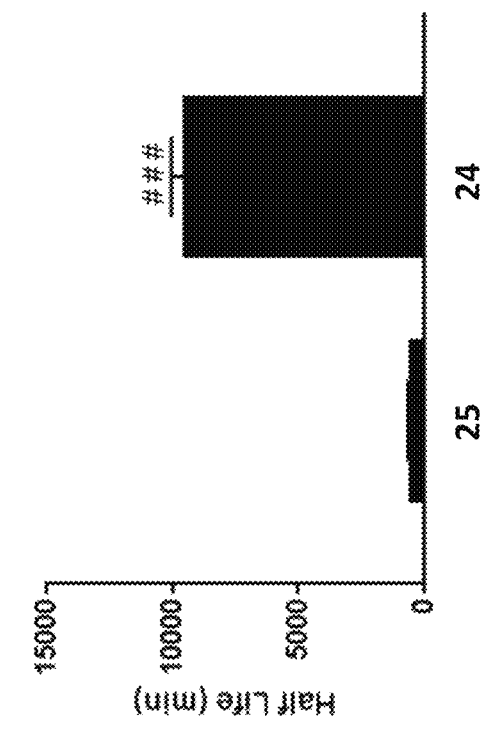
FIG. 34A
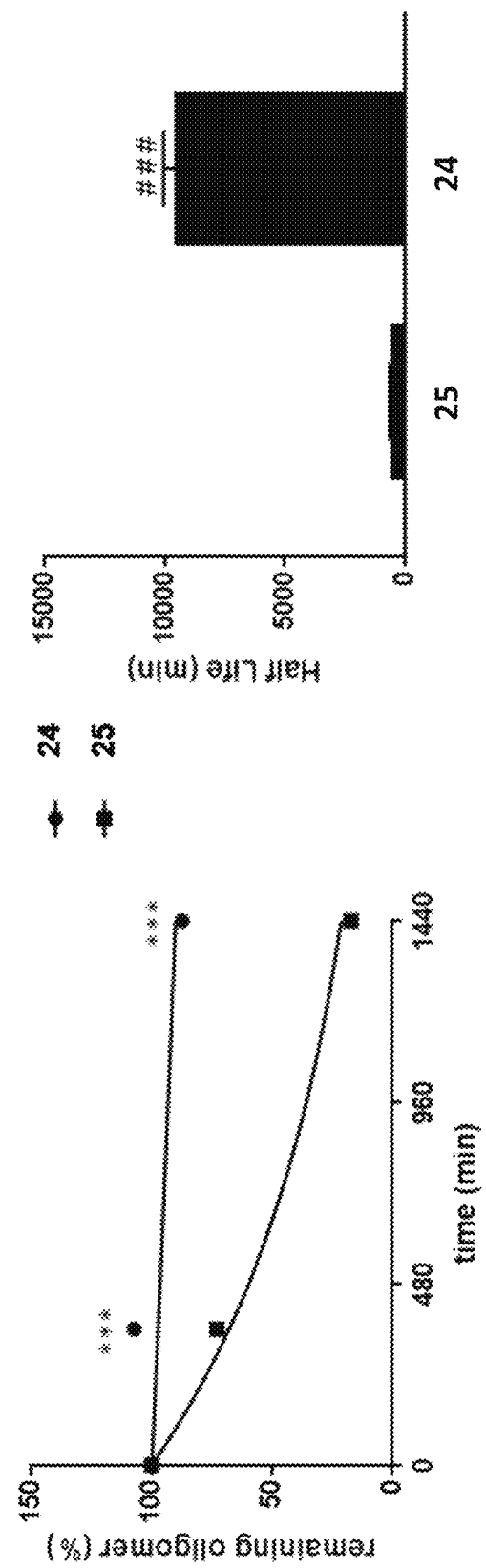
FIG. 34B
| Sequence | Compound | Half Life | SEM |
|---|---|---|---|
| 25 | Semaglutide | 11 min | 5 min |
| 24 | Semaglutide-[A$^u$A$^u$A$^u$]$^{28-31}$ | 160 h | 4 h 23 min |
FIG. 34C

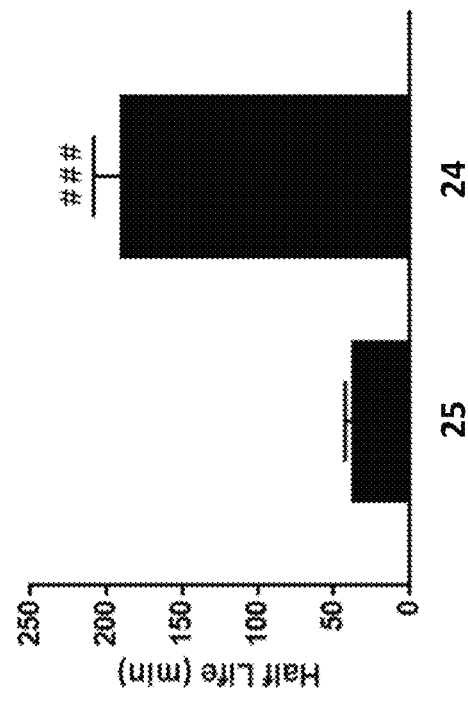
FIG. 35A
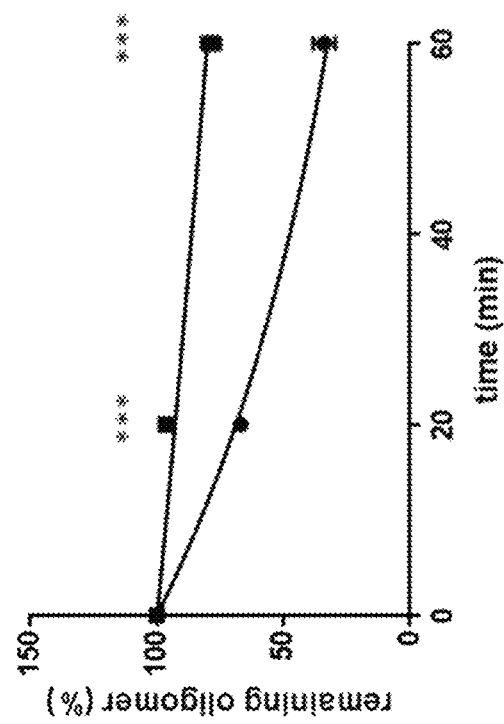
FIG. 35B
| Sequence | Compound | Half Life | SEM |
|---|---|---|---|
| 25 | Semaglutide | 38 min | 5 min |
| 24 | Semaglutide-[A$^u$A$^u$A$^u$]$^{28-31}$ | 3 h 12 min | 17 min |
FIG. 35C

| Sequence | Compound | EC50 (pM) | SEM (pM) |
|---|---|---|---|
| 25 | Semaglutide | 1.38 | 0.08 |
| 24 | Semaglutide-[$A^uA^uA^u$]$^{28-31}$ | 1.07 | 0.03 |

SEQUENCE LISTING

```
<160> NUMBER OF SEQ ID NOS: 26

<210> SEQ ID NO 1
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: C-terminal amidation

<400> SEQUENCE: 1

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: urea residue with a proteinogenic amino acid
      side chain, such as an aspartic acid side chain
<220> FEATURE:
<221> NAME/KEY: MISC_FEATURE
<222> LOCATION: (10)..(10)
<223> OTHER INFORMATION: urea residue with a proteinogenic amino acid
      side chain, such as an alanine side chain
<220> FEATURE:
<221> NAME/KEY: MISC_FEATURE
<222> LOCATION: (11)..(11)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation

<400> SEQUENCE: 2

His Gly Glu Gly Thr Phe Thr Ser Xaa Xaa Xaa Tyr Leu Glu Gly Gln
1               5                   10                  15

Ala Ala Lys Glu Phe Ile Ala Trp Leu Val Lys Gly Arg Gly
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
```

```
<222> LOCATION: (10)..(10)
<223> OTHER INFORMATION: urea residue with a proteinogenic amino acid
      side chain, such as an alanine side chain
<220> FEATURE:
<221> NAME/KEY: MISC_FEATURE
<222> LOCATION: (11)..(11)
<223> OTHER INFORMATION: urea residue with a proteinogenic amino acid
      side chain, such as an alanine side chain
<220> FEATURE:
<221> NAME/KEY: MISC_FEATURE
<222> LOCATION: (12)..(12)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation

<400> SEQUENCE: 3

His Gly Glu Gly Thr Phe Thr Ser Asp Xaa Xaa Xaa Leu Glu Gly Gln
1               5                   10                  15

Ala Ala Lys Glu Phe Ile Ala Trp Leu Val Lys Gly Arg Gly
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: urea residue with a proteinogenic amino acid
      side chain, such as an alanine side chain
<220> FEATURE:
<221> NAME/KEY: MISC_FEATURE
<222> LOCATION: (12)..(12)
<223> OTHER INFORMATION: urea residue with a proteinogenic amino acid
      side chain, such as an alanine side chain
<220> FEATURE:
<221> NAME/KEY: MISC_FEATURE
<222> LOCATION: (13)..(13)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation

<400> SEQUENCE: 4

His Gly Glu Gly Thr Phe Thr Ser Asp Val Xaa Xaa Xaa Glu Gly Gln
1               5                   10                  15

Ala Ala Lys Glu Phe Ile Ala Trp Leu Val Lys Gly Arg Gly
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: urea residue with a proteinogenic amino acid
      side chain, such as an alanine side chain
<220> FEATURE:
<221> NAME/KEY: MISC_FEATURE
<222> LOCATION: (12)..(12)
<223> OTHER INFORMATION: urea residue with a proteinogenic amino acid
      side chain, such as an tyrosine side chain
<220> FEATURE:
```

```
<221> NAME/KEY: MISC_FEATURE
<222> LOCATION: (13)..(13)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation

<400> SEQUENCE: 5

His Gly Glu Gly Thr Phe Thr Ser Asp Val Xaa Xaa Xaa Gly Gln
1               5                   10                  15

Ala Ala Lys Glu Phe Ile Ala Trp Leu Val Lys Gly Arg Gly
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: urea residue with a proteinogenic amino acid
      side chain, such as an alanine side chain
<220> FEATURE:
<221> NAME/KEY: MISC_FEATURE
<222> LOCATION: (13)..(13)
<223> OTHER INFORMATION: urea residue with a proteinogenic amino acid
      side chain, such as an alanine side chain
<220> FEATURE:
<221> NAME/KEY: MISC_FEATURE
<222> LOCATION: (14)..(14)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation

<400> SEQUENCE: 6

His Gly Glu Gly Thr Phe Thr Ser Asp Val Ser Xaa Xaa Xaa Gly Gln
1               5                   10                  15

Ala Ala Lys Glu Phe Ile Ala Trp Leu Val Lys Gly Arg Gly
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(13)
<223> OTHER INFORMATION: urea residue with a proteinogenic amino acid
      side chain, such as an alanine side chain
<220> FEATURE:
<221> NAME/KEY: MISC_FEATURE
<222> LOCATION: (14)..(14)
<223> OTHER INFORMATION: urea residue with a proteinogenic amino acid
      side chain, such as an alanine side chain
<220> FEATURE:
<221> NAME/KEY: MISC_FEATURE
<222> LOCATION: (15)..(15)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation
```

```
<400> SEQUENCE: 7

His Gly Glu Gly Thr Phe Thr Ser Asp Val Ser Ser Xaa Xaa Xaa Gln
1               5                   10                  15

Ala Ala Lys Glu Phe Ile Ala Trp Leu Val Lys Gly Arg Gly
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: urea residue with a proteinogenic amino acid
      side chain, such as an alanine side chain
<220> FEATURE:
<221> NAME/KEY: MISC_FEATURE
<222> LOCATION: (15)..(15)
<223> OTHER INFORMATION: urea residue with a proteinogenic amino acid
      side chain, such as an alanine side chain
<220> FEATURE:
<221> NAME/KEY: MISC_FEATURE
<222> LOCATION: (16)..(16)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation

<400> SEQUENCE: 8

His Gly Glu Gly Thr Phe Thr Ser Asp Val Ser Ser Tyr Xaa Xaa Xaa
1               5                   10                  15

Ala Ala Lys Glu Phe Ile Ala Trp Leu Val Lys Gly Arg Gly
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: urea residue with a proteinogenic amino acid
      side chain, such as an tyrosine side chain
<220> FEATURE:
<221> NAME/KEY: MISC_FEATURE
<222> LOCATION: (15)..(15)
<223> OTHER INFORMATION: urea residue with a proteinogenic amino acid
      side chain, such as an glutamic acid side chain
<220> FEATURE:
<221> NAME/KEY: MISC_FEATURE
<222> LOCATION: (16)..(16)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation

<400> SEQUENCE: 9

His Gly Glu Gly Thr Phe Thr Ser Asp Val Ser Ser Tyr Xaa Xaa Xaa
1               5                   10                  15

Ala Ala Lys Glu Phe Ile Ala Trp Leu Val Lys Gly Arg Gly
            20                  25                  30
```

```
<210> SEQ ID NO 10
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: urea residue with a proteinogenic amino acid
      side chain, such as an alanine side chain
<220> FEATURE:
<221> NAME/KEY: MISC_FEATURE
<222> LOCATION: (16)..(16)
<223> OTHER INFORMATION: urea residue with a proteinogenic amino acid
      side chain, such as an alanine side chain
<220> FEATURE:
<221> NAME/KEY: MISC_FEATURE
<222> LOCATION: (17)..(17)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation

<400> SEQUENCE: 10

His Gly Glu Gly Thr Phe Thr Ser Asp Val Ser Ser Tyr Leu Xaa Xaa
1               5                   10                  15

Xaa Ala Lys Glu Phe Ile Ala Trp Leu Val Lys Gly Arg Gly
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: urea residue with a proteinogenic amino acid
      side chain, such as an glutamic acid side chain
<220> FEATURE:
<221> NAME/KEY: MISC_FEATURE
<222> LOCATION: (16)..(16)
<223> OTHER INFORMATION: urea residue with a proteinogenic amino acid
      side chain, such as an alanine side chain
<220> FEATURE:
<221> NAME/KEY: MISC_FEATURE
<222> LOCATION: (17)..(17)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation

<400> SEQUENCE: 11

His Gly Glu Gly Thr Phe Thr Ser Asp Val Ser Ser Tyr Leu Xaa Xaa
1               5                   10                  15

Xaa Ala Lys Glu Phe Ile Ala Trp Leu Val Lys Gly Arg Gly
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (16)..(16)
```

<223> OTHER INFORMATION: urea residue with a proteinogenic amino acid
      side chain, such as an alanine side chain
<220> FEATURE:
<221> NAME/KEY: MISC_FEATURE
<222> LOCATION: (17)..(17)
<223> OTHER INFORMATION: urea residue with a proteinogenic amino acid
      side chain, such as an alanine side chain
<220> FEATURE:
<221> NAME/KEY: MISC_FEATURE
<222> LOCATION: (18)..(18)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation

<400> SEQUENCE: 12

His Gly Glu Gly Thr Phe Thr Ser Asp Val Ser Ser Tyr Leu Glu Xaa
1               5                   10                  15

Xaa Xaa Lys Glu Phe Ile Ala Trp Leu Val Lys Gly Arg Gly
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (17)..(17)
<223> OTHER INFORMATION: urea residue with a proteinogenic amino acid
      side chain, such as an alanine side chain
<220> FEATURE:
<221> NAME/KEY: MISC_FEATURE
<222> LOCATION: (18)..(18)
<223> OTHER INFORMATION: urea residue with a proteinogenic amino acid
      side chain, such as an alanine side chain
<220> FEATURE:
<221> NAME/KEY: MISC_FEATURE
<222> LOCATION: (19)..(19)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation

<400> SEQUENCE: 13

His Gly Glu Gly Thr Phe Thr Ser Asp Val Ser Ser Tyr Leu Glu Gly
1               5                   10                  15

Xaa Xaa Xaa Glu Phe Ile Ala Trp Leu Val Lys Gly Arg Gly
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: urea residue with a proteinogenic amino acid
      side chain, such as an alanine side chain
<220> FEATURE:
<221> NAME/KEY: MISC_FEATURE
<222> LOCATION: (19)..(19)
<223> OTHER INFORMATION: urea residue with a proteinogenic amino acid
      side chain, such as an alanine side chain
<220> FEATURE:
<221> NAME/KEY: MISC_FEATURE

```
<222> LOCATION: (20)..(20)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation

<400> SEQUENCE: 14

His Gly Glu Gly Thr Phe Thr Ser Asp Val Ser Ser Tyr Leu Glu Gly
1               5                   10                  15

Gln Xaa Xaa Xaa Phe Ile Ala Trp Leu Val Lys Gly Arg Gly
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (19)..(19)
<223> OTHER INFORMATION: urea residue with a proteinogenic amino acid
      side chain, such as an alanine side chain
<220> FEATURE:
<221> NAME/KEY: MISC_FEATURE
<222> LOCATION: (20)..(20)
<223> OTHER INFORMATION: urea residue with a proteinogenic amino acid
      side chain, such as an alanine side chain
<220> FEATURE:
<221> NAME/KEY: MISC_FEATURE
<222> LOCATION: (21)..(21)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation

<400> SEQUENCE: 15

His Gly Glu Gly Thr Phe Thr Ser Asp Val Ser Ser Tyr Leu Glu Gly
1               5                   10                  15

Gln Ala Xaa Xaa Xaa Ile Ala Trp Leu Val Lys Gly Arg Gly
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(22)
<223> OTHER INFORMATION: urea residue with a proteinogenic amino acid
      side chain, such as an phenylalanine side chain
<220> FEATURE:
<221> NAME/KEY: MISC_FEATURE
<222> LOCATION: (23)..(23)
<223> OTHER INFORMATION: urea residue with a proteinogenic amino acid
      side chain, such as an isoleucine side chain
<220> FEATURE:
<221> NAME/KEY: MISC_FEATURE
<222> LOCATION: (24)..(24)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation

<400> SEQUENCE: 16
```

His Gly Glu Gly Thr Phe Thr Ser Asp Val Ser Ser Tyr Leu Glu Gly
1               5                   10                  15

Gln Ala Ala Lys Glu Xaa Xaa Xaa Leu Val Lys Gly Arg Gly
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(23)
<223> OTHER INFORMATION: urea residue with a proteinogenic amino acid
      side chain, such as an alanine side chain
<220> FEATURE:
<221> NAME/KEY: MISC_FEATURE
<222> LOCATION: (24)..(24)
<223> OTHER INFORMATION: urea residue with a proteinogenic amino acid
      side chain, such as an alanine side chain
<220> FEATURE:
<221> NAME/KEY: MISC_FEATURE
<222> LOCATION: (25)..(25)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation

<400> SEQUENCE: 17

His Gly Glu Gly Thr Phe Thr Ser Asp Val Ser Ser Tyr Leu Glu Gly
1               5                   10                  15

Gln Ala Ala Lys Glu Phe Xaa Xaa Xaa Val Lys Gly Arg Gly
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (24)..(24)
<223> OTHER INFORMATION: urea residue with a proteinogenic amino acid
      side chain, such as an alanine side chain
<220> FEATURE:
<221> NAME/KEY: MISC_FEATURE
<222> LOCATION: (25)..(25)
<223> OTHER INFORMATION: urea residue with a proteinogenic amino acid
      side chain, such as an alanine side chain
<220> FEATURE:
<221> NAME/KEY: MISC_FEATURE
<222> LOCATION: (26)..(26)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation

<400> SEQUENCE: 18

His Gly Glu Gly Thr Phe Thr Ser Asp Val Ser Ser Tyr Leu Glu Gly
1               5                   10                  15

Gln Ala Ala Lys Glu Phe Ile Xaa Xaa Xaa Lys Gly Arg Gly
            20                  25                  30

<210> SEQ ID NO 19

```
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (25)..(25)
<223> OTHER INFORMATION: urea residue with a proteinogenic amino acid
      side chain, such as an alanine side chain
<220> FEATURE:
<221> NAME/KEY: MISC_FEATURE
<222> LOCATION: (26)..(26)
<223> OTHER INFORMATION: urea residue with a proteinogenic amino acid
      side chain, such as an alanine side chain
<220> FEATURE:
<221> NAME/KEY: MISC_FEATURE
<222> LOCATION: (27)..(27)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation

<400> SEQUENCE: 19

His Gly Glu Gly Thr Phe Thr Ser Asp Val Ser Ser Tyr Leu Glu Gly
1               5                   10                  15

Gln Ala Ala Lys Glu Phe Ile Ala Xaa Xaa Xaa Gly Arg Gly
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (26)..(26)
<223> OTHER INFORMATION: urea residue with a proteinogenic amino acid
      side chain, such as an alanine side chain
<220> FEATURE:
<221> NAME/KEY: MISC_FEATURE
<222> LOCATION: (27)..(27)
<223> OTHER INFORMATION: urea residue with a proteinogenic amino acid
      side chain, such as an alanine side chain
<220> FEATURE:
<221> NAME/KEY: MISC_FEATURE
<222> LOCATION: (28)..(28)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation

<400> SEQUENCE: 20

His Gly Glu Gly Thr Phe Thr Ser Asp Val Ser Ser Tyr Leu Glu Gly
1               5                   10                  15

Gln Ala Ala Lys Glu Phe Ile Ala Trp Xaa Xaa Xaa Arg Gly
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (27)..(27)
<223> OTHER INFORMATION: urea residue with a proteinogenic amino acid
```

```
      side chain, such as an alanine side chain
<220> FEATURE:
<221> NAME/KEY: MISC_FEATURE
<222> LOCATION: (28)..(28)
<223> OTHER INFORMATION: urea residue with a proteinogenic amino acid
      side chain, such as an alanine side chain
<220> FEATURE:
<221> NAME/KEY: MISC_FEATURE
<222> LOCATION: (29)..(29)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation

<400> SEQUENCE: 21

His Gly Glu Gly Thr Phe Thr Ser Asp Val Ser Ser Tyr Leu Glu Gly
1               5                   10                  15

Gln Ala Ala Lys Glu Phe Ile Ala Trp Leu Xaa Xaa Xaa Gly
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (28)..(28)
<223> OTHER INFORMATION: urea residue with a proteinogenic amino acid
      side chain, such as an alanine side chain
<220> FEATURE:
<221> NAME/KEY: MISC_FEATURE
<222> LOCATION: (29)..(29)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation
<220> FEATURE:
<221> NAME/KEY: MISC_FEATURE
<222> LOCATION: (30)..(30)
<223> OTHER INFORMATION: urea residue with a proteinogenic amino acid
      side chain, such as an alanine side chain

<400> SEQUENCE: 22

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Xaa Xaa Xaa
            20                  25                  30

<210> SEQ ID NO 23
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: urea residue with a proteinogenic amino acid
      side chain, such as an tyrosine side chain
<220> FEATURE:
<221> NAME/KEY: MISC_FEATURE
<222> LOCATION: (15)..(15)
<223> OTHER INFORMATION: urea residue with a proteinogenic amino acid
      side chain, such as an glutamic acid side chain
<220> FEATURE:
<221> NAME/KEY: MISC_FEATURE
<222> LOCATION: (16)..(16)
```

-continued

```
<223> OTHER INFORMATION: urea residue with a proteinogenic amino acid
      side chain, such as an alanine side chain
<220> FEATURE:
<221> NAME/KEY: MISC_FEATURE
<222> LOCATION: (17)..(17)
<223> OTHER INFORMATION: urea residue with a proteinogenic amino acid
      side chain, such as an alanine side chain
<220> FEATURE:
<221> NAME/KEY: MISC_FEATURE
<222> LOCATION: (18)..(18)
<223> OTHER INFORMATION: urea residue with a proteinogenic amino acid
      side chain, such as an alanine side chain
<220> FEATURE:
<221> NAME/KEY: MISC_FEATURE
<222> LOCATION: (19)..(19)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation

<400> SEQUENCE: 23

His Gly Glu Gly Thr Phe Thr Ser Asp Val Ser Ser Tyr Xaa Xaa Xaa
1               5                   10                  15

Xaa Xaa Xaa Phe Ile Ala Trp Leu Val Lys Gly Arg Gly
            20                  25

<210> SEQ ID NO 24
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: 2-aminoisobutyric acid
<220> FEATURE:
<221> NAME/KEY: MISC_FEATURE
<222> LOCATION: (20)..(20)
<223> OTHER INFORMATION: epsilon-amino group of the lysine is
      substituted with an (S)-22,40-dicarboxy-10,19,24-trioxo-3,6,12,15-
      tetraoxa-9,18,23-triazatetracontan-1-oyl side chain (i.e., 2xOEG-
      gammaGlu-C18 diacid, or bis-aminodiethoxyadetyl-LgammaGlu-C18
      diacid)
<220> FEATURE:
<221> NAME/KEY: MISC_FEATURE
<222> LOCATION: (28)..(28)
<223> OTHER INFORMATION: urea residue with a proteinogenic amino acid
      side chain, such as an alanine side chain
<220> FEATURE:
<221> NAME/KEY: MISC_FEATURE
<222> LOCATION: (29)..(29)
<223> OTHER INFORMATION: urea residue with a proteinogenic amino acid
      side chain, such as an alanine side chain
<220> FEATURE:
<221> NAME/KEY: MISC_FEATURE
<222> LOCATION: (30)..(30)
<223> OTHER INFORMATION: C-terminal amidation
<220> FEATURE:
<221> NAME/KEY: MISC_FEATURE
<222> LOCATION: (30)..(30)
<223> OTHER INFORMATION: urea residue with a proteinogenic amino acid
      side chain, such as an alanine side chain

<400> SEQUENCE: 24

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Xaa Xaa Xaa
            20                  25                  30

<210> SEQ ID NO 25
```

```
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: 2-aminoisobutyric acid
<220> FEATURE:
<221> NAME/KEY: MISC_FEATURE
<222> LOCATION: (20)..(20)
<223> OTHER INFORMATION: epsilon-amino group of the lysine is
      substituted with an (S)-22,40-dicarboxy-10,19,24-trioxo-3,6,12,15-
      tetraoxa-9,18,23-triazatetracontan-1-oyl side chain (i.e., 2xOEG-
      gammaGlu-C18 diacid, or bis-aminodiethoxyadetyl-LgammaGlu-C18
      diacid)

<400> SEQUENCE: 25

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg
            20                  25                  30

<210> SEQ ID NO 26
<211> LENGTH: 31
<212> TYPE: PRT
<213> ORGANISM: Artificial Sequence
<220> FEATURE:
<223> OTHER INFORMATION: Synthetic

<400> SEQUENCE: 26

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

PEPTIDE-OLIGOUREA HYBRID COMPOUNDS

CROSS-REFERENCE TO RELATED APPLICATIONS

The present application claims priority to and the benefit of U.S. Provisional Application No. 62/794,014, filed 18 Jan. 2019, titled: PEPTIDE-OLIGOUREA HYBRID COMPOUNDS, which is incorporated herein by reference in its entirety for all purposes.

INCORPORATION BY REFERENCE

In compliance with 37 C.F.R. § 1.52(e)(5), the sequence information contained in electronic file name: URZ0015_Sequence_Listing_ST25.txt; size 22.8 KB; created on: 3 Jan. 2020; using Patent-In 3.5.1, and Checker 4.4.6 is hereby incorporated herein by reference in its entirety.

FIELD

The present description relates to peptidomimetic foldamers, and their synthesis. In particular, the description provides peptide-amino urea hybrid peptidomimetic foldamers comprising an alpha amino acid peptide portion and an oligourea portion.

BACKGROUND

Interactions between proteins and/or their substrates or ligands are critical for normal cell function, physiologic signal transduction, as well as for therapeutic intervention in many pathophysiologic or disease-related processes. Proteins and peptides are capable of adopting compact, well-ordered conformations, and performing complex chemical operations, e.g., catalysis, highly selective recognition, etc. The three dimensional structure is the principal determinant that governs specificity in protein-protein and/or protein-substrate interactions. Thus, the conformation of peptides and proteins is central for their biological function, pharmaceutical efficacy, and their therapeutic preparation.

During the past decade, peptide therapeutics have gained considerable attention in pharmaceutical research and development (R&D). Indeed, peptides have proved to be valuable tools to access extra-cellular targets with medium to large active sites and they are now intensively investigated to access intracellular protein-protein interaction (PPI) targets, a very important topic in recent pharmaceutical research. This is remarkable considering peptides have important shortcomings as they generally show poor membrane permeability, poor bioavailability, and short in vivo half-life.

Protein folding is inextricably linked to function in both proteins and peptides because the creation of an "active site" requires proper positioning of reactive groups. Much effort has been invested in peptide and peptidomimetic chemistries to address those weaknesses in the hope of finding an alternative to peptides. Researches have endeavoured to identify synthetic polymer or oligomers, which display discrete and predictable (i.e., stable) folding and oligomerizing propensities (hereinafter referred to as "foldamers") to mimic natural biological systems. Insofar as these unnatural backbones are resistant to the action of proteases and peptidases, they are useful as probes having constrained conformational flexibility or as therapeutics with improved pharmacological properties, e.g., enhanced pharmacokinetic (PK) and/or pharmacodynamics (PD) features, such as potency and/or half-life. Whereas a naturally occurring polypeptide comprised entirely of α-amino acid residues will be readily degraded by any number of proteases and peptidases, foldamers, including hybrids of natural peptides and synthetic amino acid derivatives, mimetics or pseudo-peptides, are not.

Foldamers are also interesting molecules because of their conformational behavior. The elucidation of foldamers having discrete conformational propensities akin to those of natural proteins has led to explorations of peptides constructed from β-, γ-, or δ-amino acids. γ-Peptides containing residues bearing γ-substitution or α, γ-disubstitution or α, β, γ-trisubstitution have been shown to adopt a helical conformation defined by a 14-member turn that is stabilized by $C=O_{(i)} \rightarrow NH_{(i+3)}$ hydrogen bonds. Both the $3_{14}$ and $2.5_{12}$ helical backbones have been found suitable for the design of stabilized helical peptides useful for therapeutic purposes. For example, in order to cluster polar residues on one face of the helix, amphiphilic $3_{14}$-helical β-peptides have been constructed from hydrophobic-cationic-hydrophobic- or hydrophobic-hydrophobic-cationic residue triads.

A key principle of foldamer research is to use biomolecules as inspiration for the design and development of molecules with functions and capabilities beyond those found in nature, such as catalysts or artificial bio-receptors with tailored ligand specificity. As function is intimately linked with structure, the creation of new and unique foldamer architectures is a necessary step towards the goal of developing foldamers with tailored/pretematural functions. However, the construction of novel foldamer structures can be challenging, particularly the creation of multi-component architectures, which require controlled, precise self-assembly.

Oligomers of residues having a C1-C4 aminoalkylene carbamoyl structure (i.e., "oligoureas") comprising amino acid side chains or analogs thereof are in the limited list of such potential foldamers as they offer 3-D space similarity, metabolic compatibility, water solubility, and flexibility of functionalities. Like peptides, oligoureas (alkylene diamine residues having a urea bridging unit) are synthesised by iterative coupling on solid support and possess their own secondary, tertiary and quaternary structures based on their sequences. The compatibility of peptide-oligourea hybrids in biological systems and their utilisation in vivo is not well understood. However, the oligourea backbone is resistant to proteases and can be interfaced with peptide α-helices as it adopts an helical conformation that does not disrupt the peptide α-helix propagation. This is noteworthy as 1) many biologically active peptides contain an α-helix (a large fraction of PPIs involve an α-helix) and 2) those portions could potentially be replaced or partially replaced by oligoureas to preserve binding while improving the proteolytic resistance of the peptide. Such strategy would be a valuable tool to design new peptide therapeutics as their pharmaceutical properties could be improved.

The design and construction of biomimetic systems is a challenging yet potentially highly rewarding endeavour, contributing to the development of new biomaterials, catalysts, drug-delivery systems and tools for the manipulation of biological processes. The design of entirely new, non-natural folded architectures resembling biopolymers with the ability to adopt well-defined stable secondary structures comparable to those found in nature have considerable potential for use in a range of applications such as biomaterials, bio-recognition, nano-machines and as therapeutic agents. As such, there exists an ongoing need in the art for the design and production of peptidomimetic compounds that are both efficacious and that overcome one or more of the problems observed with natural amino acid structures.

SUMMARY

Oligoureas represent interesting classes of peptidomimetic foldamers that have previously received little attention. The present disclosure relates to the surprising and unexpected discovery that alpha-amino acid peptide-amino urea hybrid foldamer compounds (i.e., "peptide-amino urea hybrids" or "peptide-oligourea hybrids") can be designed, which preserve the function of the native or parental alpha-amino acid peptide, but that also demonstrate superior half-life and protease resistance. The peptide-oligourea hybrids as described herein are compounds in which a portion of the native or parental alpha-amino acid sequence is replaced or substituted by at least one amino urea residue comprising substitutions, e.g., naturally or non-naturally occurring amino acid side chains, that mimic the secondary structure conformation and biochemistry of the native or parental peptide (a substitution comprising a plurality of amino urea residues is referred to herein as an "oligourea"). In a particular aspect, it was surprisingly discovered that one can replace alpha-amino acids from the native or parental peptide with fewer amino urea residues, which can reduce the size of the peptide. Also, because the peptide-oligourea hybrid compounds as described herein can adopt desired secondary structures similar to the native or parental peptides, including, e.g., helicoidal structures, they can serve as, for example, receptor ligands, effector molecules, agonists, antagonists, modulators of protein-protein interactions, organocatalysts, or enzymes.

Thus, in one aspect, the description provides a compound of the structure:

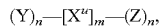

wherein, Y and Z represent alpha-amino acid residues of a native or parent peptide; each n is independently an integer ≥1; $X^u$ represents a non-peptide amino urea or ureido residue substitution of two or more alpha-amino acids of the native or parent peptide; and m is an integer ≥1, wherein the non-peptide amino urea residue substitution is configured to mimic the native or parent alpha-amino acid side-chain chemistry and/or 3-D configuration, and wherein the peptide-amino urea hybrid compound retains at least one of binding activity, biological activity or both of the native or parent peptide.

In certain embodiments, each n is independently an integer greater than or equal to two. In some embodiments, n is an integer from 2-50. In certain embodiments, m is an integer greater than or equal to 1. In some embodiments, m is an integer from 1-50. In still further embodiments, m is 1, 2, 3, 4, 5, 6, 7, 8, or 9.

In any of the aspects or embodiments described herein, $X^u$ is an optionally substituted 1,2-ethylene diamine residue including a urea linking unit such as an N-linked 2-aminoethyl carbamamoyl or 2-aminoethyl urea residue. In certain embodiments, the $X^u$ residue includes a substitution with a proteinaceous amino acid side chain at the α-carbon ($X^{ua}$), the β-carbon or both.

In certain embodiments, the peptide-amino urea hybrid compounds comprise a substitution comprising at least 1, 2, 3, 4, 5, 6, 7, 8, 9, 10, 15, 20, 25 or more non-peptide amino urea or ureido peptidomimetic residues. That is, the native or parent peptide includes a substitution of alpha-amino acids with non-peptide amino urea or ureido peptidomimetic residues. In certain embodiments, the hybrid compounds described herein comprise amino urea residues of formula I:

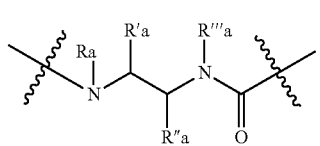

wherein $R^a$, $R'^a$, $R''^a$, and $R'''^a$ groups are independently selected from hydrogen, any side chain of a natural amino acid, linear, branched or cyclic C1-C6-alkyl, alkenyl or alkynyl; mono- or -bicyclic aryl, mono or bicyclic heteroaryl having up to five heteroatoms selected from N, O and S; mono or bicyclic aryl-C1-C6-alkyl, alkenyl or alkynyl; C1-C6-alkyloxy, aryloxy, heteroaryloxy, thio, C1-C6-alkylthio, amino, mono ordi-C1-C6-alkylamino, carboxylic acid, carboxamide mono- or di-C1-C6-alkylcarboxamine, sulfonamide, urea, mono-di or tri-substituted urea, thiourea, or guanidine.

In certain embodiments, when one of $R'^a$ or $R'''^a$ is hydrogen the other group cannot be hydrogen.

In certain embodiments, the peptide-amino urea hybrid compounds comprise a substitution comprising at least 1, 2, 3, 4, 5, 6, 7, 8, 9, 10, 15, 20, 25 or more non-peptide amino urea or ureido peptidomimetic residues. In certain embodiments, the hybrid compounds described herein comprise amino urea residues of formula II:

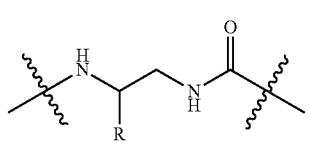

wherein R is independently selected from a hydrogen atom, an amino acid side chain, a (C1-C10) alkyl, (C1-C10) alkenyl, (C1-C10) alkynyl, (C5-C12) monocyclic or bicyclic aryl, (C5-C14) monocyclic or bicyclic aralkyl, (C5-C14) monocyclic or bicyclic heteroalkyl and (C1-C10) monocyclic or bicyclic heteroaryl group comprising up to 5 heteroatoms selected from N, O, and S, said groups being able to be non-substituted or substituted by 1 to 6 substituents further selected from the group consisting of: a halogen atom, an $NO_2$, OH, amidine, benzamidine, imidazole, alkoxy, (C1-C4) alkyl, $NH_2$, CN, trihalomethyl, (C1-C4) acyloxy, (C1-C4) monoalkylamino, (C1-C4) dialkylamino, guanidino group, bis alkylated or bis acylated guanido group.

In certain embodiments, peptide-amino urea hybrid compounds as described herein comprise amino urea substitutions of a native or parent peptide that is a naturally occurring peptide or a peptide derived from a naturally occurring protein. In certain additional embodiments, the parent peptide is a non-naturally occurring peptide or peptidomimetic. In certain embodiments, the parent peptide is glucagon-like peptide-1 (GLP-1).

In any of the aspects or embodiments described herein, the peptide-oligourea hybrid compound comprises a substitution of 2, 3, 4, 5, 6, 7, 8, 9, 10, 15, 20, 25 or more alpha-amino acids of the parent peptide with one or more amino urea residues as described herein. In certain embodiments, the number of non-peptide oligourea residues is less than the number of alpha-amino acids substituted (i.e., the number of alph-amino acids removed or replaced). In any of the aspects or embodiments described herein, the oligourea residues in the substitution comprise proteinaceous sidechains.

In certain embodiments, the peptide-oligourea hybrid compound comprises a number of amino urea residues that is at least one less than the number of alph-amino acids being substituted.

In certain embodiments, the description provides a glucagon-like peptide-1 (GLP-1) oligourea hybrid compounds. In certain additional embodiments, the GLP-1 peptide-oligourea hybrid demonstrates a resistance to dipeptidyl peptidase-4 (DPP-4) in PBS or in serum that is greater than native or naturally occurring GLP-1. In certain embodiments, the GLP-1 peptide-oligourea hybrid demonstrates a resistance to neutral endopeptidase 24.11 (NEP 24.11) in PBS or in serum that is greater than native or naturally occurring GLP-1. In certain embodiments, the GLP-1 peptide-oligourea hybrid demonstrates an EC50 of less than about 10 µM. In still additional embodiments, the GLP-1 peptide-oligourea hybrid demonstrates binding to GLP-1 receptor (GLP-1R). In certain embodiments, the GLP-1 peptide-oligourea hybrid demonstrates bioactivity in a cAMP production assay.

In any of the aspects or embodiments described herein, the peptide-oligourea hybrid has a structure selected from the group of SEQ ID NO: 2-24. In certain embodiments, the peptide-oligourea hybrid as a structures selected from SEQ ID NO: 5, 9, 11, 14, 16, 22, 23, or 24.

In an additional aspect, the description provides a pharmaceutical composition comprising a peptide-oligourea hybrid as described herein, and a pharmaceutically acceptable excipient. In certain embodiments, the pharmaceutical composition comprises an effective amount of a peptide-oligourea hybrid as described herein. In certain embodiments, the effective amount is a therapeutically effective amount or a synergistically effective amount.

In an additional aspect, the description provides a method of treating a disease, comprising administering to a subject in need thereof a composition comprising an effective amount of a peptide-oligourea hybrid as described herein, or a pharmaceutical formulation comprising the same and a pharmaceutically acceptable excipient, wherein composition is effective at treating or ameliorating at least one symptom of the disease. In certain embodiments, the disease is a metabolic disorder. In certain additional embodiments, the disease is diabetes.

In certain embodiments, the oligourea residues are coupled, joined to or contiguous with a peptide α-helix region. In certain additional embodiments, the hybrid compounds also comprise amino urea residues are "fused" to a terminus, e.g., amino terminus, carboxy terminus or both, of an α-amino acid peptide. In certain embodiments, the peptide-oligourea hybrid compounds comprise additional amino urea residues coupled to a side-chain group of a backbone residue (either an alpha amino acid, an amino urea or both).

In any aspect or embodiment described herein, the compounds can further comprise at least one additional chemical modification. In certain embodiments, the chemical modification includes at least one of, for example, acetylation, phosphorylation, methylation, glycosylation, prenylation, isoprenylation, farnesylation, geranylation, pegylation, a disulfide bond, or combination thereof.

In an additional aspect, the description provides pharmaceutically acceptable acid and base salt forms of the compounds described herein.

The oligourea foldamers and compounds as described herein, including pharmaceutically acceptable salts thereof, are useful for the preparation of a medicament and/or the treatment of disease in a subject. The compounds of the disclosure may optionally be administered with at least one of a pharmaceutically acceptable excipient, pharmacologically active agent or a combination thereof. As such, in an addition aspect the description provides compositions comprising an effective amount of a peptide-oligourea hybrid or oligourea foldamers, or a oligourea helical bundle as described herein, and a pharmaceutically acceptable carrier or excipient.

The description also provides methods of treating a disease or disorder or ameliorating the effects of the same comprising the steps of administering to an individual in need thereof, a composition comprising: an effective amount of a peptide-oligourea hybrid, oligourea foldamers, a oligourea compound, or salt form thereof as described herein, wherein the composition is effective for treating, preventing or ameliorating the effects of the disease or disorder.

In another aspect, the present description provides methods of making and using the compounds, or the compositions as described herein. For example, the oligourea compounds or oligourea foldamers as described herein can be used as a diagnostic agent or a therapeutic agent for the treatment of a disease or condition.

In an additional aspect the present description provides methods of making oligourea compounds, oligourea foldamer compounds, or peptide-oligourea compounds as described herein. Thus, in one aspect, the present description provides for the synthesis of a non-peptide helical structure. In another aspect, the present description provides methods of making and using the compounds of the disclosure.

In another embodiment, the peptide-oligourea hybrid compound is selected from the group consisting of SEQ ID NO: 2-24.

In any aspect or embodiment described herein, the c-terminus is amidated.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional advantages objects and embodiments are expressly included within the scope of the present disclosure. The publications and other materials used herein to illuminate the background of the disclosure, and in particular cases, to provide additional details respecting the practice, are incorporated by reference, and for convenience are listed in the appended bibliography.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating an embodiment of the disclosure and are not to be construed as limiting the disclosure. Further objects, features and advantages of the disclosure will become apparent from the following detailed description taken in conjunction with the accompanying figures showing illustrative embodiments of the disclosure, in which:

FIG. 1. Schematic representation of different GFP-1 analogues previously reported and of the present approach based on peptide/oligourea hybrids.

FIGS. 2A, 2B, and 2C. Comparison of α-helical and oligourea backbones. (2A) Overlay (side-views) of a peptide oligourea hybrid (derived from the crystal structures of helical peptide-oligourea hybrids[16]) over a peptide. (2B) Overlay (side- and top-views) of an oligourea triad (extracted from A, green backbone) over a tetrapeptide in α-helical conformation (gray backbone). (2C) Chemical structures of an oligourea backbone, as well of $X^u$, $X^{u\alpha}$, X residues used in this study and their associated cartoon representations.

FIG. 3. Concentration-response curves for selected analogues.

FIGS. 4A, 4B, and 4C. Blood glucose study in mice. (4A, 4B and 4C) Blood glucose concentration in normal mice (C57BL/6J, male, 20-25 g, n=3) before and after dosing: 5 μg/mouse (~50 nmol/kg) i.v. Formulation: 20 μg/mL in PBS 1×. The dosing was done at T0. (two-way anova and Bonferroni post test: *p<0.05;  p<0.01; * p<0.001)

FIGS. 5A1, 5A2, 5B1, 5B2, 5C1, 5C2, 5D1, and 5D2. (5A1, 5B1, 5C1, 5D1) Intra peritoneal glucose tolerance test (IPGTT) at different time after dosing in fasted normal mice (C57BL/6J, male, 20-25 g). Dosage: 200 μg/kg (~50 nmol/kg) i.v. Formulation: 20 μg/mF in PBS 1×. IPGTT: glucose 2 g/kg i.p. at T0, and different time points after dosing. (5A) IPGTT after 5 min (n=4). (5B) IPGTT after 30 min (n=6). (5C) IPGTT after 2 h (n=6). (5D) IPGTT after 4 h (n=3). (5A2, 5B2, 5C2, 5D2) AUC of the corresponding IPGTT curve, (two-way anova and Bonferroni post test: *p<0.05;  p<0.01; * p<0.001; one way anova with Dunnett's multiple comparison test: ## p<0.01; ### p<0.001)

FIGS. 7A, 7B, and 7C. (7A) demonstrates the concentration-response curve (receptor-mediated cAMP produced) for EC50 determination of peptide SEQ ID NO: 1 in cells expressing the GFP-1R. (7B) demonstrates the enzymatic degradation of peptide SEQ ID NO: 1 by NEP 24.11. (7C) demonstrates the mouse plasma degradation of peptide SEQ ID NO: 1.

FIGS. 8A, 8B, and 8C. (8A) demonstrates the concentration-response curve (receptor-mediated cAMP produced) for EC50 determination of peptide-oligourea hybrid SEQ ID NO: 2 in cells expressing the GLP-1R. (8B) demonstrates the enzymatic degradation of peptide SEQ ID NO: 2 by NEP 24.11. (8C) demonstrates the mouse plasma degradation results for peptide SEQ ID NO: 2.

FIGS. 15A, 15B, and 15C. (15A) demonstrates the concentration-response curve (receptor-mediated cAMP produced) for EC50 determination of peptide-oligourea SEQ ID NO: 9 in cells expressing the GLP-1R. (15B) demonstrate the enzymatic degradation of peptide-oligourea hybrid SEQ ID NO: 9 by NEP 24.11. (15C) demonstrates the mouse plasma degradation of peptide-oligourea hybrid SEQ ID NO: 9.

FIG. 16. Demonstrates the concentration-response curve (receptor-mediated cAMP produced) for EC50 determination of peptide-oligourea hybrid SEQ ID NO: 10 in cells expressing the GLP-1R.

FIGS. 17A, 17B, and 17C. (17A) Demonstrates the concentration-response curve (receptor-mediated cAMP produced) for EC50 determination of peptide-oligourea hybrid SEQ ID NO: 11 in cells expressing the GLP-1R. (17B) demonstrates the enzymatic degradation of peptide-oligourea hybrid SEQ ID NO: 11 by NEP 24.11. (17C) demonstrates the mouse plasma degradation of peptide-oligourea hybrid SEQ ID NO: 11.

FIG. 18. Demonstrates the concentration-response curve (receptor-mediated cAMP produced) for EC50 determination of peptide-oligourea hybrid SEQ ID NO: 12 in cells expressing the GLP-1R.

FIGS. 34A, 34B, and 34C. (34A) Demonstrates the mouse plasma degradation assay (two-way anova and Bonferroni post test: *$p<0.05$;  $p<0.01$; * $p<0.001$); (34B) Half life in pancreatin (two-way anova and Dunnett post test: *$p<0.05$;  $p<0.01$; * $p<0.001$); (34C) EC50 values and standard error of the mean values.

FIGS. 35A, 35B, and 35C. (35A) Demonstrates the enzymatic degradation (Pancreatin) (two-way anova and Bonferroni post test: *$p<0.05$;  $p<0.01$; * $p<0.001$); (35B) Half life in pancreatin (two-way anova and Dunnett post test: *$p<0.05$;  $p<0.01$; * $p<0.001$); (35C) EC50 values and standard error of the mean values.

DETAILED DESCRIPTION

Figure 6:
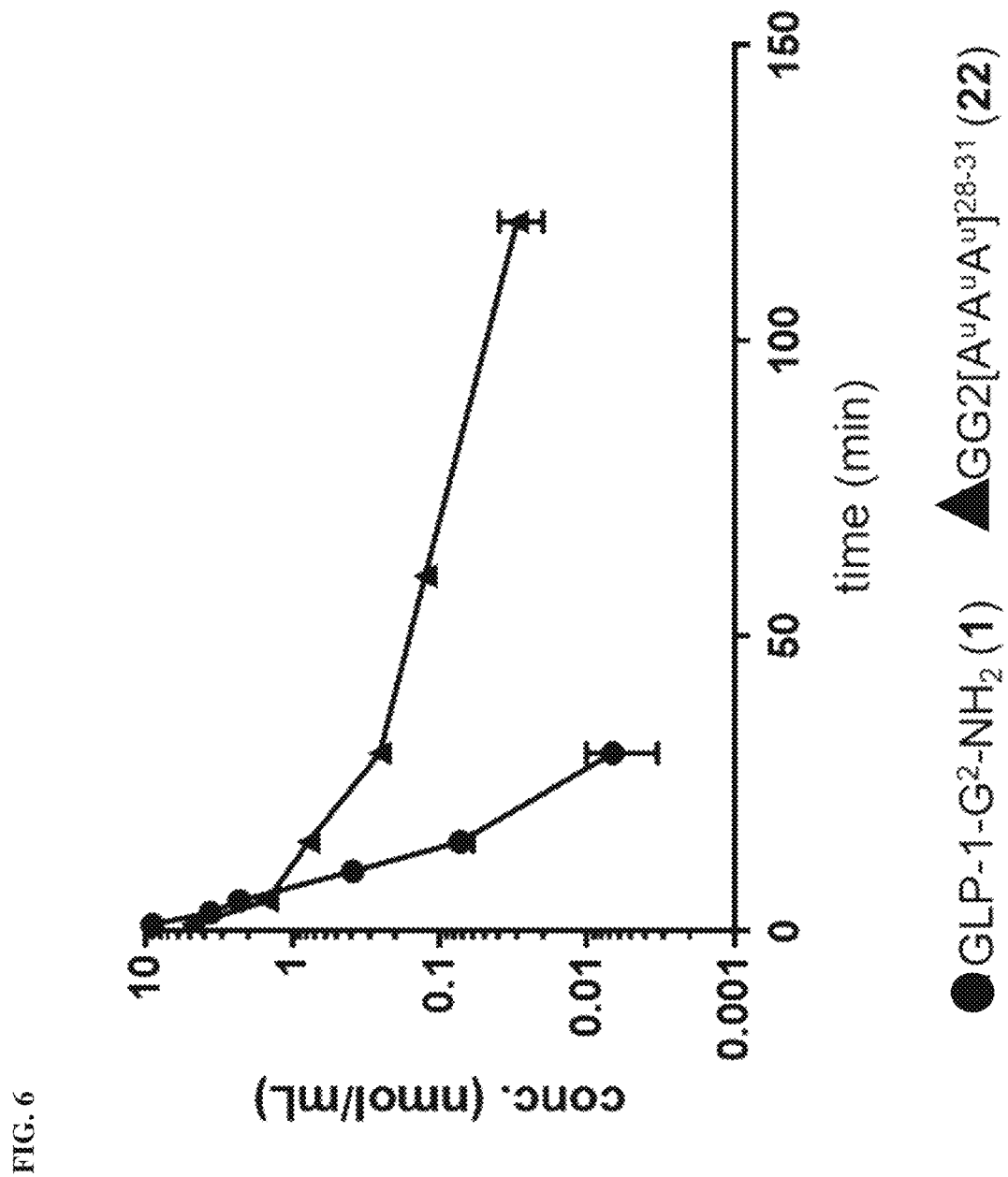
FIG. 6. Pharmacokinetic evaluation in Mice of 1 and 22 by i.v. administration. Mice (C57B16, n=3, total 36) treated with GFP-1 analogues (1 mg/kg).

The following is a detailed description of the invention provided to aid those skilled in the art in practicing the present disclosure. Those of ordinary skill in the art may make modifications and variations in the embodiments described herein without departing from the spirit or scope of the present disclosure. Unless otherwise defined, all technical and scientific terms used herein have the same meaning as commonly understood by one of ordinary skill in the art to which this disclosure belongs. The terminology used in the description of the invention herein is for describing particular embodiments only and is not intended to be limiting of the disclosure. All publications, patent applications, patents, figures and other references mentioned herein are expressly incorporated by reference in their entirety.

U.S. Provisional Patent Application No. 61/868,128 filed 21 Aug. 2013 titled: Oligourea Foldamer Organocatalysts and Methods of Their Use; U.S. Provisional Patent Application No. 61/887,651 filed 7 Oct. 2013 titled: Peptide-Oligourea Chimeric Compounds and Methods of Their Use; U.S. patent application Ser. No. 14/465,680 filed 21 Aug. 2014 titled: Peptide-oligourea Chimeric Compounds and Methods of their Use; U.S. Provisional Patent Application No. 62/212,590 filed 1 Sep. 2015 entitled: Quaternary Assemblies of Water-Soluble Non-Peptide Helical Foldamers, their Use and Production Thereof, are hereby incorporated by reference in their entirety for all purposes. Furthermore, the disclosures of each and every patent, patent application, and publication cited herein are hereby incorporated herein by reference in their entirety.

As described above, oligoureas represent interesting classes of peptidomimetic foldamers. Presently described are alpha-amino acid peptide-amino urea hybrid foldamer compounds (i.e., "peptide-amino urea hybrid" or "peptide-oligourea hybrid" compounds) that preserve the function of the native or parental alpha-amino acid peptide, but that also demonstrate superior half-life and protease resistance. The peptide-oligourea hybrid compounds as described herein are compounds in which a portion of the native or parental alpha-amino acid sequence is replaced or substituted by at least one amino urea residue comprising substitutions, e.g., naturally or non-naturally occurring amino acid side chains, that mimic the secondary structure conformation and biochemistry of the native or parental peptide (a substitution comprising a plurality of amino urea residues is referred to herein as an "oligourea"). As described herein below, it was surprisingly discovered alpha-amino acids from the native or parental peptide can be substituted or replaced with fewer amino urea residues. Because the peptide-oligourea hybrid compounds as described herein can adopt desired secondary structures similar to the native or parental peptides, including, e.g., helicoidal structures, they can serve as, for example, receptor ligands, effector molecules, agonists, antagonists, modulators of protein-protein interactions, organocatalysts, or enzymes.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The following terms are used to describe the present disclosure. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the 10 United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

"Peptides" are typically short chains of amino acid monomers linked by peptide (amide) bonds, the covalent chemical bonds formed when the carboxyl group of one amino acid reacts with the amino group of another. The shortest peptides are dipeptides, consisting of 2 amino acids joined by a single peptide bond, followed by tripeptides, tetrapeptides, etc. A polypeptide is a long, continuous, and unbranched peptide chain.

The term "amino" or "amine" as used herein refers to —NH2 and substituted derivatives thereof wherein one or both of the hydrogens are independently replaced with 20 substituents selected from the group consisting of alkyl, haloalkyl, fluoro alkyl, alkenyl, alkynyl, carbocyclyl, heterocyclyl, aryl, aralkyl, hetero aryl, hetero aralkyl, alkylcarbonyl, haloalkylcarbonyl, carbocyclylcarbonyl, fluoroalkylcarbonyl, alkenylcarbonyl, heterocyclylcarbonyl, arylcarbonyl, alkynylcarbonyl, aralkylcarbonyl, heteroarylcarbonyl, heteroaralkylcarbonyl and the sulfonyl and sulfinyl groups defined above; or when both hydrogens together are replaced with an alkylene group (to form a ring which contains the nitrogen). Representative examples include, but are not limited to methylamino, acetylamino, and dimethylamino.

"Amino acid" refers to any molecule that contains both amino and carboxylic acid functional groups, and includes any of the naturally occurring amino acids (e.g. Ala, Arg, Asn, Asp, Cys, Glu, Gin, Gly, His, Hyl, Hyp, lie, Leu, Lys, Met, Phe, Pro, Ser, Thr, Trp, Tyr, and Val) in D, L, or DL form. The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine). The term is inclusive of various types of amino acids including α-, β-, γ-, or δ-amino acids, analogs and derivatives of the same, unless the context clearly indicates otherwise.

The term "amino acid sidechain" or "amino acid residue" shall mean, within context, a radical of a D- or L-amino acid sidechain (derived from an amino acid) which functions as a substituent on another group, often an alkylene (usually a methylene) group on R2' or R3' as otherwise described herein. Preferred amino acid sidechains for use in the present disclosure are derived from the sidechains of both natural and unnatural amino acids, preferably including, for example, alanine, β-alanine, arginine, asparagine, aspartic acid, cyclohexylalanine, cysteine, cystine, glutamic acid, glutamine, glycine, phenylalanine, histidine, isoleucine, lysine, leucine, methionine, naphthylalanine, norleucine, norvaline, proline, serine, threonine, valine, tryptophan or tyrosine, among others.

Unless the context clearly indicates otherwise, the term "any amino acid" can mean any natural or synthetic amino acid, including α-, β-, γ-, or δ-amino acids, possibly modified by the presence of one or more substituents, or combinations thereof, including analogs, derivatives, mimetics, and peptoid versions of the same. More precisely the term α-amino acid means an alpha aminated amino acid with the following general structure:

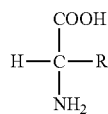

where R represents the side chain of the amino acid. In the context of the present disclosure, R therefore represents the side chain of a side or non-side amino acid. The term "natural amino acid" means any amino acid which is found naturally in vivo in a living being. Natural amino acids therefore include amino acids coded by mRNA incorporated into proteins during translation but also other amino acids found naturally in vivo which are a product or by-product of a metabolic process, such as for example ornithine which is generated by the urea production process by arginase from L-arginine. In the present disclosure, the amino acids used can therefore be natural or not. Namely, natural amino acids generally have the L configuration but also, according to the disclosure, an amino acid can have the L or D configuration. Moreover, R is of course not limited to the side chains of natural amino acid but can be freely chosen.

As used herein, a "urea" group is an organic compound with the chemical formula $CO(NH_2)_2$. The molecule has two $-NH_2$ groups joined by a carbonyl (C=O) functional group. Oligomers of, e.g., ethylenediamine residues having a urea linkage can be synthesized from ethyldiamine carbamoyl residues.

Unless indicated otherwise, the term "peptide precursor" or "parental peptide" refers, but is in no way limited to, a parental α-peptide sequence that is coupled with oligourea pseudopeptide or peptidomimetic subunits or substituting oligourea pseudopeptide subunits (i.e., exchanging one or more α-amino acids for one or more oligourea pseudopeptide subunits).

Unless indicated otherwise, the term "oligourea" refers, but is in no way limited to, a residue containing N,N'-linked urea residues including oligomers of substituted or unsubstituted N-2-ethylaminocarbamoyl or 1,2-ethylene diamine residues.

The term "compound", as used herein, unless otherwise indicated, refers to any specific chemical compound disclosed herein and includes tautomers, regioisomers, geometric isomers, and where applicable, stereoisomers, including optical isomers (enantiomers) and other steroisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomeric ally enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented within the context of the compound shown.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "amido" as used herein means an ammo group, as defined herein, appended to the parent molecular moiety through a carbonyl.

The term "cyano" as used herein means a —C≡N group.

The term "nitro" as used herein means a —NO2 group.

The term "azido" as used herein means a —N3 group.

The abbreviations Me, Et, Ph, Tf, Nf, Ts, Ms, Cbz, and Boc represent methyl, ethyl, phenyl, trifluoromethanesulfonyl, nonafluorobutanesulfonyl, p-toluenesulfonyl, methanesulfonyl, carbobenzyloxy, and tert-butyloxycarbonyl, respectively.

A more comprehensive list of the abbreviations utilized by organic chemists of ordinary skill in the art appears in the first issue of each volume of the *Journal of Organic Chemistry*; this list is typically presented in a table entitled Standard List of Abbreviations, and is incorporated herein by reference.

"Alkyl" refers to a branched or unbranched alkyl group having 1-6 carbon atoms, a branched or unbranched alkenyl group having 1-6 carbon atoms, a branched or unbranched alkinyl group having 1-6 carbon atoms. The term "alkyl" shall mean within its context a linear, branch-chained or cyclic fully saturated hydrocarbon radical or alkyl group, preferably a C1-C10, more preferably a C1-C6, alternatively a C1-C3 alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain preferred embodiments, compounds according to the present disclosure which may be used to covalently bind to dehalogenase enzymes. These compounds generally contain a side chain (often linked through a polyethylene glycol group) which terminates in an alkyl group which has a halogen substituent (often chlorine or bromine) on its distil end which results in covalent binding of the compound containing such a moiety to the protein.

The term "Alkenyl" refers to linear, branch-chained or cyclic C2-C10 (preferably C2-C6) hydrocarbon radicals containing at least one C=C bond. The term "Alkynyl" refers to linear, branch chained or cyclic C2-C10 (preferably C2-C6) hydrocarbon radicals containing at least one C≡C bond.

The term "alkylene" when used, refers to a —(CH2)n- group (n is an integer generally from 0-6), which may be optionally substituted. When substituted, the alkylene group preferably is substituted on one or more of the methylene groups with a C1-C6 alkyl group (including a cyclopropyl group or a t-butyl group), more preferably a methyl group, but may also be substituted with one or more halo groups, preferably from 1 to 3 halo groups or one or two hydroxyl groups or O—(C1-C6 alkyl) groups. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene group may be substituted with an amino acid side chain such as group obtained from an amino acid (a natural or unnatural amino acid) such as, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes C0 means that carbon is absent and is replaced with H. Thus, a range of carbon atoms which is C0-C6 includes carbons atoms of 1, 2, 3, 4, 5 and 6 and for C0, H stands in place of carbon. The term "substituted" or "optionally substituted" shall mean independently (i.e., where more than substituent occurs, each substituent is independent of another substituent), one or more substituents (independently, up to five substitutents, preferably up to three substituents, often 1 or 2 substituents on a moiety in a compound according to the present disclosure and may include substituents which themselves may be further substituted) at a carbon (or nitrogen) position anywhere on a molecule within context, and independently includes as substituents hydroxyl, thiol, carboxyl, cyano (C≡N), nitro (NO2), halogen (preferably, 1, 2 or 3 halogens, especially on an alkyl, especially a methyl group such as a trifluoromethyl), an alkyl group (preferably, C1-C10, more preferably, C1-C6), aryl (especially phenyl and substituted phenyl for example benzyl or benzoyl), alkoxy group (preferably, C1-C6 alkyl or aryl, including phenyl and substituted phenyl), thioether (C1-C6 alkyl or aryl), acyl (preferably, C1-C6 acyl), ester or thioester (preferably, C1-C6 alkyl or aryl) including alkylene ester (such that attachment is on the alkylene group, rather than at the ester function which is preferably substituted with a C1-C6 alkyl or aryl group), preferably, C1-C6 alkyl or aryl, halogen (preferably, F or Cl), amine (including a five- or six-membered cyclic alkylene amine, further including a C1-C6 alkyl amine or a C1-C6 dialkyl amine which alkyl groups may be substituted with one or two hydroxyl groups) or an optionally substituted —N(C0-C6 alkyl)C(O)(O—C1-C6 alkyl) group (which may be optionally substituted with a polyethylene glycol chain to which is further bound an alkyl group containing a single halogen, preferably chlorine substituent), hydrazine, amido, which is preferably substituted with one or two C1-C6 alkyl groups (including a carboxamide which is optionally substituted with one or two C1-C6 alkyl groups), alkanol (preferably, C1-C6 alkyl or aryl), or alkanoic acid (preferably, C1-C6 alkyl or aryl).

The term "substituted" (each substituent being independent of another substituent) shall also mean within its context of use C1-C6 alkyl, C1-C6 alkoxy, halogen, amido, carboxamido, sulfone, including sulfonamide, keto, carboxy, C1-C6 ester (oxyester or carbonylester), C1-C6 keto, urethane —O—C(O)—NR1R2 or —N(R1)-C(O)—O—R1, nitro, cyano and amine (especially including a C1-C6 alkylene-NR1R2, a mono- or di-C1-C6 alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —(CH2)m- (here, m and n are in context, 1, 2, 3, 4, 5 or 6), —S—, —S(O)—, S02- or —NH—C(O)—NH—, —(CH2)nOH, —(CH2)nSH, —(CH2)nCOOH, C1-C6 alkyl, —(CH2)nO—(C1-C6 alkyl), —(CH2)nC(O)—(C1-C6 alkyl), —(CH2)nOC(O)—(C1-C6 alkyl), —(CH2)nC(O) O—(C1-C6 alkyl), —(CH2)nNHC(O)—R1, —(CH2)nC (O)—NR1R2, —(OCH2)nOH, —(CH2O)nCOOH, C1-C6 alkyl, —(OCH2)nO—(C1-C6 alkyl), —(CH2O)nC(O)— (C1-C6 alkyl), —(OCH2)nNHC(O)—R1, —(CH2O)nC (O)—NR1R2, —S(O)2-RS, —S(O)—RS (RS is C1-C6 alkyl or a —(CH2)m-NR1R2 group), NO2, CN or halogen (F, Cl, Br, I, preferably F or Cl), depending on the context of the use of the substituent. R1 and R2 are each, within context, H or a C1-C6 alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted C1-C6 alkyl groups (methyl, ethyl or hydroxymethyl or hydroxyethyl is preferred, thus providing a chiral center), an amido group as described hereinabove, or a urethane group 0-C(O)— NR1R2 group where R1 and R2 are as otherwise described herein, although numerous other groups may also be used as substituents. Various optionally substituted moieties may be substituted independently with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

"Hydroxyl" refers the functional group —OH when it is a substituent in an organic compound.

"Heterocycle" refers to a heterocyclic group having from 4 to 9 carbon atoms and at least one heteroatom selected from the group consisting of N, O or S, and may be aromatic (heteroaryl) or non-aromatic. Thus, the heteroaryl moieties are subsumed under the definition of heterocycle, depending on the context of its use. Exemplary heteroaryl groups are described hereinabove. Exemplary nonaromatic heterocyclic groups for use in the present disclosure include, for example, pyrrolidinyl, pyrrolinyl, piperidinyl, piperazinyl, N-methylpiperazinyl, imidazolinyl, pyrazolidinyl, imidazolidinyl, morpholinyl, tetrahydropyranyl, azetidinyl, oxetanyl, oxathiolanyl, pyridone, 2-pyrrolidone, ethyleneurea, 1,3-dioxolane, 1,3-dioxane, 1,4-dioxane, phthalimide and succinimide, among others.

Heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO2-alkyl, —SO2-substituted alkyl, —SO2-aryl, oxo (═O), and —SO2-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

"Heteroaryl" refers to a heterocyclic group having from 4 to 9 carbon atoms and at least one heteroatom selected from the group consisting of N, O or S with at least one ring of this group being aromatic. Heteroaryl groups having one or more nitrogen, oxygen, or sulfur atoms in the ring (monocyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzo thiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

"Substituted heteroaryl" refers to a heterocyclic group having from 4 to 9 carbon atoms and at least one heteroatom selected from the group consisting of N, O or S with at least one ring of this group being aromatic and this group being substituted with one or more substituents selected from the group consisting of halogen, alkyl, carbyloxy, carbylmercapto, alkylamino, amido, carboxyl, hydroxyl, nitro, mercapto or sulfo, whereas these generic substituent group have meanings which are identical with definitions of the corresponding groups as defined in this legend.

The term "thiol" refers to the group —SH.

The term "thioalkoxy" refers to the group —S-alkyl.

"Amidine" refers to a functional group that has two amine groups attached to the same carbon atom with one carbon-nitrogen double bond: HN═CR'—NH"2.

"Alkoxyl" refers to an alkyl group linked to oxygen thus: R—O—, where R is an alkyl.

"Substituted alkyl" refers to a branched or unbranched alkyl, alkenyl or alkinyl group having 1-10 carbon atoms and having substituted by one or more substituents selected from the group consisting of hydroxyl, mercapto, carbylmercapto, halogen, carbyloxy, amino, amido, carboxyl, cycloalkyl, sulfo or acyl. These substituent generic groups having the meanings being identical with the definitions of the corresponding groups as defined herein.

"Halogen" refers to fluorine, bromine, chlorine, and iodine atoms.

"Acyl" denotes the group —C(O)$R_e$, where $R_e$ is hydrogen, alkyl, substituted alkyl, aryl, substituted aryl, arylalkyl, substituted arylalkyl, cycloalkyl, substituted cycloalkyl whereas these generic groups have meanings which are identical with definitions of the corresponding groups as defined in this legend.

"Acloxy" denotes the group —OAc, where Ac is an acyl, substituted acyl, heteroacyl or substituted heteroacyl whereas these generic groups have meanings which are identical with definitions of the corresponding groups as defined in this legend.

"Alkylamino" denotes the group —N$R_f R_g$, where $R_f$ and $R_g$, that are independent of one another, represent hydrogen, alkyl, substituted alkyl, aryl, substituted aryl, heteroaryl or substituted heteroaryl, whereas these generic substituents have meanings which are identical with definitions of the corresponding groups defined herein.

"Aryl" refers to an aromatic carbocyclic group having from 1 to 18 carbon atoms and being a substituted (as otherwise described herein) or unsubstituted monovalent aromatic radical having a single ring (e.g., benzene, phenyl, benzyl) or condensed (fused) rings, wherein at least one ring is aromatic (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems.

"Substituted aryl" refers to an aromatic carbocyclic group having from 1 to 18 carbon atoms and being composed of at least one aromatic ring or of multiple condensed rings at least one of which being aromatic. The ring(s) are optionally substituted with one or more substituents selected from the group consisting of halogen, alkyl, hydroxyl, carbylmercapto, alkylamino, carbyloxy, amino, amido, carboxyl, nitro, mercapto or sulfo, whereas these generic substituent group have meanings which are identical with definitions of the corresponding groups as defined in this legend.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

"Cycloalkyl" refers to a monocyclic or polycyclic alkyl group containing 3 to 15 carbon atoms.

"Substituted cycloalkyl" refers to a monocyclic or polycyclic alkyl group containing 3 to 15 carbon atoms and being substituted by one or more substituents selected from the group consisting of halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group containing 3 to 15 carbon atoms which at least one ring carbon atom of its cyclic structure being replaced with a heteroatom selected from the group consisting of N, O, S or P.

"Substituted heterocycloalkyl" refers to a monocyclic or polycyclic alkyl group containing 3 to 15 carbon atoms which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms. Preferred alkenyl groups include ethenyl (—CH=CH2), n-propenyl (—CH2CH=CH2), iso-propenyl (—C(CH3)=CH2), and the like.

"Imidazole" refers to a heterocyclic base of the general formula: $C_3H_4N_2$.

"Aralkyl group" refers to, for example, a C1-C6 alkyl group which is attached to 1 or 2 aromatic hydrocarbon rings having from 6 to 10 carbon atoms and which has a total of 7 to 14 carbon atoms, such as the benzyl, alpha-naphthylmethyl, indenylmethyl, diphenylmethyl, 2-phenethyl, 2-alpha-naphthylethyl, 3-phenylpropyl, 3-alpha-naphthylpropyl, phenylbutyl, 4-alpha-naphthylbutyl or 5-phenylpentyl groups.

"Guanidine" refers generally to the amidine of amidocarbonic acid and has the general formula of: $C(NH_2)_3$.

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

In one aspect, the description provides for oligourea compounds comprising aliphatic oligoureas at least partially encapsulating an agent. In certain embodiments, the aliphatic oligoureas form a oligourea helical bundle. In another embodiment, the aliphatic oligoureas are comprised of short amphiphilic α-helicomimetic foldamers with proteinaceous sidechains. In an embodiment, the short amphiphilic α-helicomimetic foldamers self-assemble into the oligourea helical bundle. Furthermore, the foldamers can self-assemble under aqueous conditions. Because the compounds as described herein can adopt desired secondary structures similar to native peptides, including, e.g., helicoidal structures, they can serve as, for example, receptor ligands, effector molecules, agonists, antagonists, modulators of protein-protein interactions, organocatalysts, or enzymes.

Peptide-Oligourea Hybrid Compounds

In certain embodiments, the description provides hybrid compounds comprising amino urea residues or oligomers of the same (i.e., oligoureas). For example, compounds as described herein comprise optionally substituted C1-C4 alkylene diamine residues having a urea bridging unit (e.g., N, N'-linked). In certain embodiments, the residues are formed from a C1-C4 diaminoalkyl carbamoyl. In certain embodiments, the hybrid compounds comprise one or more optionally substituted 1,2-ethylene diamine residues having a urea bridging unit, or an optionally substituted 1-(2-aminoethyl urea) residue, or 2-aminoethyl carbamoyl residue, wherein substitution is an amino acid side chain.

In one aspect, the description provides a compound of the structure:

$$(Y)_n—[X^u]_m—(Z)_n,$$

wherein, Y and Z represent alpha-amino acid residues of a native or parent peptide; each n is independently an integer $\geq 1$; $X^u$ represents a non-peptide amino urea or ureido residue substitution of two or more alpha-amino acids of the native or parent peptide; and m is an integer $\geq 1$, wherein the non-peptide amino urea residue substitution is configured to mimic the native or parent alpha-amino acid side-chain chemistry and/or 3-D configuration, and wherein the peptide-amino urea hybrid compound retains at least one of binding activity, biological activity or both of the native or parent peptide.

In certain embodiments, each n is independently an integer greater than or equal to two. In some embodiments, n is an integer from 2-50. In certain embodiments, m is an integer greater than or equal to 1. In some embodiments, m is an integer from 1-50. In still further embodiments, m is 1, 2, 3, 4, 5, 6, 7, 8, or 9.

In any of the aspects or embodiments described herein, $X^u$ is an optionally substituted 1,2-ethylene diamine residue including a urea linking unit such as an N-linked 2-aminoethyl carbamamoyl or 1-(2-aminoethyl urea) residue. In certain embodiments, the $X^u$ residue includes a substitution with a proteinaceous amino acid side chain at the second, i.e., α-carbon ($X^{u\alpha}$), the β-carbon or both.

In certain aspects, the present description provides peptide-oligourea hybrid foldamer compounds comprising alpha-amino acid residues, and non-peptide oligourea residues.

In certain aspects the non-peptide oligourea residues form a helix.

In certain embodiments, the non-peptide oligourea helical foldamer is an aliphatic oligourea. In a particular embodiment, the non-peptide oligourea helical foldamer is a short amphiphilic α-helicomimetic foldamer with proteinaceous side-chains.

In certain embodiments, the peptide-oligourea hybrid compounds comprise a substitution comprising at least 1, 2, 3, 4, 5, 6, 7, 8, 9, 10, 15, 20, 25 or more non-peptide amino urea or ureido peptidomimetic residues. That is, the native or parent peptide includes a substitution of alpha-amino acids with non-peptide amino urea or ureido peptidomimetic residues. In certain embodiments, the hybrid compounds described herein comprise amino urea residues of formula I:

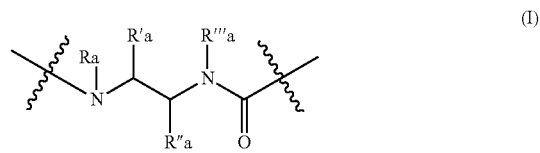

(I)

wherein R$^a$, R$'^a$, R$''^a$, and R$'''^a$ groups are independently selected from hydrogen, any side chain of a natural amino acid, linear, branched or cyclic C1-C6-alkyl, alkenyl or alkynyl; mono- or -bicyclic aryl, mono or bicyclic heteroaryl having up to five heteroatoms selected from N, O and S; mono or bicyclic aryl-C1-C6-alkyl, alkenyl or alkynyl; C1-C6-alkyloxy, aryloxy, heteroaryloxy, thio, C1-C6-alkyl-thio, amino, mono ordi-C1-C6-alkylamino, carboxylic acid, carboxamide mono- or di-C1-C6-alkylcarboxamine, sulfonamide, urea, mono-di or tri-substituted urea, thiourea, or guanidine.

In certain embodiments, when one of R$'^a$ or R$''^a$ is hydrogen the other group cannot be hydrogen.

In certain embodiments, the peptide-oligourea hybrid compounds comprise a substitution comprising at least 1, 2, 3, 4, 5, 6, 7, 8, 9, 10, 15, 20, 25 or more non-peptide amino urea or ureido peptidomimetic residues. In certain embodiments, the hybrid compounds described herein comprise amino urea residues of formula II:

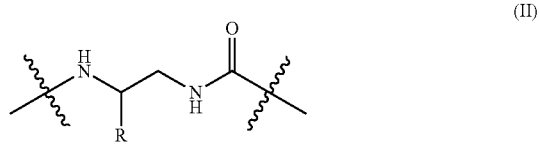

(II)

wherein R is independently selected from a hydrogen atom, an amino acid side chain, a (C1-C10) alkyl, (C1-C10) alkenyl, (C1-C10) alkynyl, (C5-C12) monocyclic or bicyclic aryl, (C5-C14) monocyclic or bicyclic aralkyl, (C5-C14) monocyclic or bicyclic heteroalkyl and (C1-C10) monocyclic or bicyclic heteroaryl group comprising up to 5 heteroatoms selected from N, O, and S, said groups being able to be non-substituted or substituted by 1 to 6 substituents further selected from the group consisting of: a halogen atom, an NO$_2$, OH, amidine, benzamidine, imidazole, alkoxy, (C1-C4) alkyl, NH2, CN, trihalomethyl, (C1-C4) acyloxy, (C1-C4) monoalkylamino, (C1-C4) dialkylamino, guanidino group, bis alkylated or bis acylated guanido group.

In further embodiments, the peptide-oligourea hybrid compounds comprise at least 1, 2, 3, 4, 5, 6, or more non-peptide amino urea or ureido peptidomimetic and oligomers thereof, wherein the amino urea residues have a structure selected from the group consisting of:

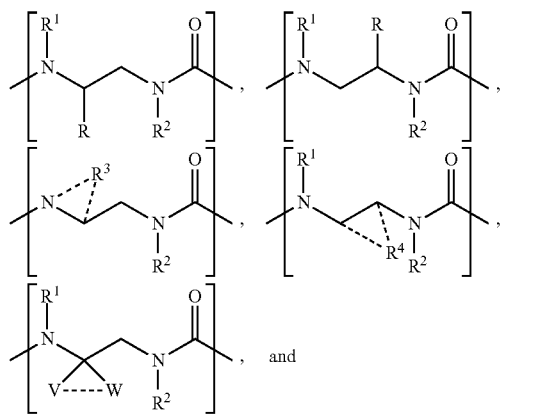

wherein R is independently selected from the group consisting of hydrogen, any side chain of a natural amino acid, linear, branched or cyclic C1-C6-alkyl, alkenyl or alkynyl; mono- or -bicyclic aryl, mono or bicyclic heteroaryl having up to five heteroatoms selected from N, O and S; mono or bicyclic aryl-C1-C6-alkyl, alkenyl or alkynyl; C1-C6-alkyloxy, aryloxy, heteroaryloxy, thio, C1-C6-alkylthio, amino, mono ordi-C1-C6-alkylamino, carboxylic acid, carboxamide mono- or di-C1-C6-alkylcarboxamine, sulfonamide, urea, mono-di or tri-substituted urea, thiourea, guanidine;

wherein R$^1$ is independently selected from the group consisting of hydrogen, linear, branched or cyclic C1-C6-alkyl, alkenyl or alkynyl; mono- or -bicyclic aryl, mono or bicyclic heteroaryl having up to five heteroatoms selected from N, O and S;

wherein R$^2$ is independently selected from the group consisting of hydrogen, linear, branched or cyclic C1-C6-alkyl, alkenyl or alkynyl; mono- or -bicyclic aryl, mono or bicyclic heteroaryl having up to five heteroatoms selected from N, O and S;

wherein R$^3$ together with the carbon and nitrogen atoms to which it is attached independently defines a substituted or unsubstituted, monocyclic or bicyclic C3-C10 heterocyclic ring having one or more N, O, or S atom(s) as the heteroatom(s); and substitutents on the cycloalkyl, cycloalkenyl or heterocycle moieties are independently selected from the group consisting of linear, branched or cyclic C1-C6 alkyl, aralkyl, —O—C(O)—NR$^1$R$^2$ or —N(R$^1$)—C(O)—O—R$^1$, C1-C6 alkylene-NR$^1$R$^2$, —(CH$_2$)$_n$—NH—C(=NR$^1$)NHR$^2$, —NH—, —NHC(O)—, —O—, =O, —(CH$_2$)$_m$— (here, m and n are in context, 1, 2, 3, 4, 5 or 6), —S—, —S(O)—, SO$_2$— or —NH—C(O)—NH—, —(CH$_2$)$_n$OH, —(CH$_2$)$_n$SH, —(CH$_2$)$_n$COOH, —(CH$_2$)$_n$O—(C1-C6 alkyl), —(CH$_2$)$_n$C(O)—(C1-C6 alkyl), —(CH$_2$)$_n$OC(O)—(C1-C6 alkyl), —(CH$_2$)$_n$C(O)O—(C1-C6 alkyl), —(CH$_2$)$_n$NHC(O)—R$^1$, —(CH$_2$)$_n$C(O)—NR$^1$R$^2$, —(OCH$_2$)$_n$OH, —(OCH$_2$)$_n$O—(C1-C6 alkyl), —(CH$_2$O)$_n$C(O)—(C1-C6 alkyl), —(OCH$_2$)$_n$NHC(O)—R$^1$, —(CH$_2$O)$_n$C(O)—NR$^1$R$^2$, —NO$_2$, —CN, or -halogen.R1 and R2 are each, within context, H or a C1-C6 alkyl group;

wherein R$^4$ together with the carbon atoms to which it is attached independently defines a substituted or unsubstituted, monocyclic or bicyclic C3-C10 cycloalkyl, cycloalkenyl or heterocyclic ring having one or more N, O, or S atom(s) as the heteroatom(s); and substitutents on the cycloalkyl, cycloalkenyl or heterocycle moieties are independently selected from the group consisting of linear, branched or cyclic C1-C6 alkyl, aralkyl, —O—C(O)—NR$^1$R$^2$ or —N(R$^1$)—C(O)—O—R$^1$, C1-C6 alkylene-NR$^1$R$^2$, —(CH$_2$)$_n$—NH—C(=NR$^1$)NHR$^2$, —NH—, —NHC(O)—, —O—, =O, —(CH$_2$)$_m$— (here, m and n are in context, 1, 2, 3, 4, 5 or 6), —S—, —S(O)—, SO$_2$— or —NH—C(O)—NH—, —(CH$_2$)$_n$OH, —(CH$_2$)$_n$SH, —(CH$_2$)$_n$COOH, —(CH$_2$)$_n$O—(C1-C6 alkyl), —(CH$_2$)$_n$C(O)—(C1-C6 alkyl), —(CH$_2$)$_n$OC(O)—(C1-C6 alkyl), —(CH$_2$)$_n$C(O)O—(C1-C6 alkyl), —(CH$_2$)$_n$NHC(O)—R$^1$, —(CH$_2$)$_n$C(O)—NR$^1$R$^2$, —(OCH$_2$)$_n$OH, —(OCH$_2$)$_n$O—(C1-C6 alkyl), —(CH$_2$O)$_n$C(O)—(C1-C6 alkyl), —(OCH$_2$)$_n$NHC(O)—R$^1$, —(CH$_2$O)$_n$C(O)—NR$^1$R$^2$, —NO2, —CN, or -halogen, R$^1$ and R$^2$ are each, within context, H or a C1-C6 alkyl group; and wherein V and W are combined, together with the carbon atoms to which they are bonded, and independently define a substituted or unsubstituted, monocyclic or bicyclic C3-C10 cycloalkyl, cycloalkenyl or heterocyclic ring having one or more N, O, or S atom(s) as the heteroatom(s).

In any of the aspects or embodiments described herein, the peptide-oligourea hybrid compound comprises a substitution of 2, 3, 4, 5, 6, 7, 8, 9, 10, 15, 20, 25 or more alpha-amino acids of the parent peptide with one or more amino urea residues as described herein. In certain embodiments, the number of non-peptide oligourea residues is less than the number of alpha-amino acids substituted (i.e., the number of alph-amino acids removed or replaced). In any of the aspects or embodiments described herein, the oligourea residues in the substitution comprise proteinaceous sidechains.

In certain embodiments, the peptide-oligourea hybrid compound comprises a number of amino urea residues that is at least one less than the number of alph-amino acids being substituted. In certain embodiments, the peptide-oligourea hybrid compound comprises a number of non-peptide oligourea residues according to the function:

[X$^u$]$_m$=(X)$_{(p-q)}$, wherein,

X$^u$ and m are defined as above;

X is an alpha-amino acid residue of the parent peptide;

p is an integer ≥2 and q is a non-zero integer at least one less than p.

In certain embodiments, peptide-oligourea hybrid compounds as described herein comprise amino urea substitutions of a native or parent peptide that is a naturally occurring peptide or a peptide derived from a naturally occurring protein. In certain additional embodiments, the parent peptide is a non-naturally occurring peptide or peptidomimetic. In certain embodiments, the parent peptide is glucagon-like peptide-1 (GLP-1).

In certain embodiments, the description provides a glucagon-like peptide-1 (GLP-1) oligourea hybrid compounds. In certain additional embodiments, the GLP-1 peptide-oligourea hybrid demonstrates a resistance to dipeptidyl peptidase-4 (DPP-4) in PBS or in serum that is greater than native or naturally occurring GLP-1. In certain embodiments, the GLP-1 peptide-oligourea hybrid demonstrates a resistance to neutral endopeptidase 24.11 (NEP 24.11) in PBS or in serum that is greater than native or naturally occurring GLP-1. In certain embodiments, the GLP-1 peptide-oligourea hybrid demonstrates an EC50 of less than about 10 µM. In still additional embodiments, the GLP-1 peptide-oligourea hybrid demonstrates binding to GLP-1 receptor (GLP-1R). In certain embodiments, the GLP-1 peptide-oligourea hybrid demonstrates bioactivity in a cAMP production assay.

In any of the aspects or embodiments described herein, the peptide-oligourea hybrid has a structure selected from the group of SEQ ID NO: 2-24. In certain embodiments, the peptide-oligourea hybrid as a structures selected from SEQ ID NO: 5,9, 11, 14, 16, 22, 23, or 24.

In certain embodiments, the peptide-oligourea hybrid compound has a secondary structure similar to a native or parent peptide. As such, the secondary structure can act in a fashion similar to that of the native or parent peptide. For example, the secondary structure of the oligourea compound can be biologically active. By way of another example, the secondary structure can act as a receptor ligand, an effector molecule, an agonist, an antagonist, a modulator of protein-protein interactions, an organocatalyst, or an enzyme. In certain alternative embodiments, the peptide-oligourea hybrid compound may have a secondary structure that provides a function not found in nature. For example, the oligourea compound may be a catalyst with tailored substrate specificity.

In certain embodiments, the peptide-oligourea hybrid compounds comprise a peptide portion (i.e., a sequence of α-amino acid residues) contiguous with or coupled to an oligourea portion (i.e., a sequence of oligourea residues). In certain embodiments, the peptide portion comprises at least 2 α-amino acids. In certain additional embodiments, the oligourea portion comprises a non-peptide oligourea helical foldamer, for example, non-peptide oligourea peptidomimetic residues. The non-peptide oligourea helical foldamer portion can be an aliphatic oligourea. The non-peptide oligourea helical foldamer can be a short amphiphilic α-helicomimetic foldamer, which may include proteinaceous side chains.

In any of the compounds described herein, the peptide portion may comprise an α-amino acid sequence corresponding to a biologically active peptide or a fragment thereof.

In still additional embodiments, the peptide-oligourea hybrid compound as described herein is biologically active. The biological activity can stem from the peptide or the oligourea portion. For example, in certain embodiments, the compounds as described herein are enzymatically active. In still additional embodiments, the compounds as described herein are configured to bind target proteins. In certain embodiments the target protein is a cytosolic protein. In certain embodiments, the target protein is a membrane protein. In certain embodiments, the membrane protein is a receptor. In still additional embodiments, the receptor is a growth factor receptor or a G-Protein Coupled Receptor (GPCR) or a fragment thereof. In an embodiment, the peptide-oligourea hybrid is biologically and/or enzymatically active.

In certain aspects, the description provides peptide-oligourea hybrid compounds that adopt stable secondary structures, including, e.g., linear, cyclic, or helicoidal, tertiary structure, and/or quaternary structures, wherein the hybrids comprise a sequence of amino acids (i.e., a polypeptide) that has been substituted by amino urea residues that are contiguous with or coupled to the peptide backbone. In certain embodiments, the amino acid sequence comprises α-amino acids. In an additional embodiments, peptide-oligourea hybrid compound comprises two or more, e.g., 3, 4, 5, 6, 7, 8, 9, 10, 11, 12, 13, 14, 15, 16, 17, 18, 19, 20, 21, 22, 23, 24, 25, 26, 27, 28, 29, 30 or more, non-peptide amino urea residues as described herein representing a substitution of two or more amino acids from the native or parental peptide.

In any of the embodiments described herein, the peptide-oligourea hybrid compound comprises an oligourea portion contiguous with or covalently linked or joined to at least one of the amino terminus (N'), the carboxyl terminus (C'), within the peptide sequence or a combination thereof. In an embodiment, the peptide-oligourea hybrid compound comprises an oligourea portion covalently linked or joined to the C' of the peptide portion. In certain embodiments, the peptide-oligourea hybrid compound comprises an oligourea portion covalently linked or coupled to the peptide backbone downstream from the N' and upstream of the C' peptide portions.

In any of the embodiments described herein, the peptide-oligourea hybrid compound comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more amino urea residues. In a preferred embodiment, the amino urea residues of the described peptide-oligourea hybrid compounds are joined in a chain that is bound at both ends to peptide potions.

In any of the embodiments described herein, the peptide-oligourea hybrid compound comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more residues.

In another aspect, the description provides oligourea compounds and peptide-oligourea hybrid compounds as described herein further comprising at least one additional chemical modification. In certain embodiments, the chemical modification includes at least one of, for example, acetylation, phosphorylation, methylation, glycosylation, prenylation, isoprenylation, farnesylation, geranylation, pegylation, a disulfide bond, or combination thereof.

Pharmaceutical Forms

In an additional aspect, the description provides a pharmaceutical composition comprising a peptide-oligourea hybrid as described herein, and a pharmaceutically acceptable excipient. In certain embodiments, the pharmaceutical composition comprises an effective amount of a peptide-oligourea hybrid as described herein. In certain embodiments, the effective amount is a therapeutically effective amount or a synergistically effective amount.

The compounds or compositions as described herein including pharmaceutically acceptable salts thereof are useful for the preparation of a medicament and/or the treatment of disease in a subject. In the case where a salt of a compound is desired and the compound/composition is produced in the form of the desired salt, it can be subjected to purification as such. In the case where a compound/composition is produced in the free state and its salt is desired, the compound/composition is dissolved or suspended in a suitable organic solvent, followed by addition of an acid or a base to form a salt. As such, in an addition aspect the description provides compositions comprising an effective amount of a peptide-oligourea hybrid as described herein, and a pharmaceutically acceptable carrier or excipient.

The compounds or compositions of the description may optionally be administered with at least one of a pharmaceutically acceptable excipient, pharmacologically active agent or a combination thereof. These novel, unnatural peptidomimetics are resistant or wholly immune to peptidase and protease degradation and are conformationally restrained. Thus, they are useful as tools to model peptide and protein conformations in aqueous solutions. The compounds are also useful as non-enzymatically degradable probes to mimic protein behavior in solution. As such, the description further provides the compositions comprising an effective amount of a chimeric compound as described herein, and a pharmaceutically acceptable carrier or excipient.

Certain compounds or composition of the description and their salts may exist in more than one crystal form and the present disclosure includes each crystal form and mixtures thereof. Certain compounds/compositions of the disclosure and their salts may also exist in the form of solvates, for example hydrates, and the present disclosure includes each solvate and mixtures thereof.

Certain compounds/compositions of the disclosure may contain one or more chiral centers, and exist in different optically active forms. When compounds/compositions of the disclosure contain one chiral center, the compounds/compositions exist in two enantiomeric forms and the present disclosure includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound or composition of the description contains more than one chiral center, it may exist in diastereoisomeric forms. The diastereoisomeric compounds may be separated by methods known to those skilled in the art, for example chromatography or crystallization and the individual enantiomers may be separated as described above. The present disclosure includes each diastereoisomer of compounds of the disclosure and mixtures thereof.

Certain compounds of the disclosure may exist in different tautomeric forms or as different geometric isomers, and the present disclosure includes each tautomer and/or geometric isomer of compounds of the disclosure and mixtures thereof.

Certain compounds or compositions of the disclosure may exist in different stable conformational forms which may be separable. Torsional asymmetry due to restricted rotation about an asymmetric single bond, for example because of steric hindrance or ring strain, may permit separation of different conformers. The present disclosure includes each conformational isomer of compounds of the disclosure and mixtures thereof.

Certain compounds of the disclosure may exist in zwitterionic form and the present disclosure includes each zwitterionic form of compounds of the disclosure and mixtures thereof.

The present disclosure encompasses all possible isomers including tautomers and mixtures thereof. Where chiral carbons lend themselves to two different enantiomers, both enantiomers are contemplated as well as procedures for separating the two enantiomers.

The present disclosure also relates to pharmaceutically acceptable salts, racemates, and optical isomers thereof. The compounds of this disclosure typically contain one or more chiral centers. Accordingly, this disclosure is intended to include racemic mixtures, diasteromers, enantiomers and mixture enriched in one or more steroisomer. The scope of the disclosure as described and claimed encompasses the racemic forms of the compounds as well as the individual enantiomers and non-racemic mixtures thereof.

Many of the compounds of the disclosure may be provided as salts with pharmaceutically compatible counterions (i.e., pharmaceutically acceptable salts).

The term "pharmaceutically acceptable salt" is used throughout the specification to describe, where applicable, a salt form of one or more of the compounds or prodrugs described herein which are presented to increase the solubility of the compound in the gastric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure. In a preferred embodiment, the description provides pharmaceutically acceptable salts of the modified peptides as described herein, which retain the biological effectiveness and properties of the parent compounds and which are not biologically or otherwise harmful as the dosage administered. The compounds of this disclosure are capable of forming both acid and base salts by virtue of the presence of amino and carboxy groups respectively.

A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, parabromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-I,4-dioate, hexyne-I,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, ~-hydroxybutyrate, glycolate, maleate, tartrate, methanesulfonate, propanesulfonate, naphthalene-I-sulfonate, naphthalene-2-sulfonate, mandelate and the like salts.

Preferred pharmaceutically acceptable acid addition salts include those formed with mineral acids such as hydrochloric acid and hydrobromic acid, and especially those formed with organic acids such as maleic acid. Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di-lower alkyl-N (hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

Prodrugs

The description also provides prodrug forms of the above described peptide-oligourea hybrid compounds, wherein the prodrug is metabolized in vivo to produce an analog or derivative as set forth above. Indeed, some of the described compounds may be a prodrug for another analog or derivative. The term "prodrug" is well understood in the art and refers to an agent which is converted into the parent drug in vivo by some physiological chemical process (e.g., a prodrug on being brought to the physiological pH is converted to the desired drug form). For example, see *Remington's Pharmaceutical Sciences,* 1980, vol. 16, Mack Publishing Company, Easton, Pa., 61 and 424.

Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a prodrug would be a compound of the present disclosure wherein it is administered as an ester (the "pro-drug") to facilitate transmittal across a cell membrane where water solubility is not beneficial, but then it is metabolically hydrolyzed to the carboxylic acid once inside the cell where water solubility is beneficial. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this disclosure include but are not limited to carboxylic acid substituents (e.g., —C(O)2H or a moiety that contains a carboxylic acid) wherein the free hydrogen is replaced by (C1-C4)alkyl, (Cz-C12)alkanoyloxymethyl, (C4-C9)1-(alkanoyloxy)ethyl, I-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, I-methyl-1-10 (alkoxycarbonyloxy)ethyl having from 5 to 8 carbon atoms, N-(alkoxycarbonyl)aminomethyl having from 3 to 9 carbon atoms, 1-(N-(alkoxycarbonyl)

amino) ethyl having from 4 to 10 carbon atoms, 3-phthalidyl, 4-crotonolactonyl, gamma-butyrolacton-4-yl, di-N,N—(C1-C2)alkylamino(C2-C3)alkyl (such as ~-dimethylaminoethyl), carbamoyl-(C1-C2)alkyl, N,N-die C1-C2)-alkylcarbamoyl-(C1-15 C2)alkyl and piperidino-, pyrrolidino- or morpholino(C2-C3)alkyl.

Other exemplary pro-drugs release an alcohol or amine of a compound of the disclosure wherein the free hydrogen of a hydroxyl or amine substituent is replaced by (C1-C6) alkanoyloxymethyl, 1-((C1-C6)alkanoyloxy)ethyl, I-methyl-1-((C1-C6)alkanoyloxy)ethyl, (C1-C6)alkoxycarbonyl-oxymethyl, N—(C1-C6)alkoxycarbonylamino-20 methyl, succinoyl, (C1-C6)alkanoyl, α-amino($C_1$-$C_4$)alkanoyl, arylactyl and α-aminoacyl, or α-aminoacyl-a-aminoacyl wherein said α-aminoacyl moieties are independently any of the naturally occurring L-amino acids found in proteins, —P(O)(OH)2'-P(O)(O(C1-C6)alkyl)2 or glycosyl (the radical resulting from detachment of the hydroxyl of the hemiacetal of a carbohydrate).

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective 30 Groups in Organic Synthesis, 2nd ed.; Wiley: New York, 1991). Protected forms of the inventive compounds are included within the scope of this disclosure.

The term "chemically protected form," as used herein, pertains to a compound in which one or more reactive functional groups are protected from undesirable chemical reactions, that is, are in the form of a protected or protecting group (also known as a masked or masking group). It may be convenient or desirable to prepare, purify, and/or handle the active compound in a chemically protected form.

By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1991), and Protective Groups in Organic Synthesis (T. Green and P. Wuts; 3rd Edition; John Wiley and Sons, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH3, —OAc). For example, an aldehyde or ketone group may be protected as an acetal or ketal, respectively, in which the carbonyl group (C(=O)) is converted to a diether (C(OR)2), by reaction with, for example, a primary alcohol. The aldehyde or ketone group is readily regenerated by hydrolysis using a large excess of water in the presence of acid. For example, an amine group may be protected, for example, as an amide (NRC(=O)R) or a urethane (—NRC(=O)OR), for example, as: a methyl amide (—NHC(=O)CH3); a benzyloxy amide (—NHC(=O)OCH2C6HsNHCbz); as a t-butoxy amide (NHC=(=O)OC(CH3)3, —NHBoc); a 2-biphenyl-2-propoxy amide (NHC(=O)OC(CH3) 2C6H4C6HsNHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical.

For example, a carboxylic acid group may be protected as an ester or an amide, for example, as: a benzyl ester; a t-butyl ester; a methyl ester; or a methyl amide. For example, a thiol group may be protected as a thioether (—SR), for example, as: a benzyl thioether; or an acetamidomethyl ether (—SCH2NHC(=O)CH3). In at least certain examples, the compounds disclosed herein can be used in the treatment of disorders associated with pathogen infection. Disorders associated with infection by pathogens include, but are not limited to, infection by viruses (DNA viruses, RNA viruses, animal viruses, and the like), bacteria (e.g., gram positive bacteria, gram negative bacteria, acid-fast bacteria, and the like), fungi, parasitic microbes, nematodes, and the like.

The term "pharmaceutically acceptable derivative" is used throughout the specification to describe any pharmaceutically acceptable prodrug form (such as an ester, amide other prodrug group) which, upon administration to a patient, provides directly or indirectly the present compound or an active metabolite of the present compound. The term "independently" is used herein to indicate that the variable, which is independently applied, varies independently from application to application.

Formulations

Suitable routes for administration include oral, peroral, rectal, vassal, topical (including ocular, buccal and sublingual), vaginal and parental (including subcutaneous, intramuscular, intravitreous, intravenous, intradermal, intrathecal and epidural). The preferred route of administration will depend upon the condition of the patient, the toxicity of the compound and the site of infection, among other considerations known to the clinician.

The therapeutic composition of the disclosure comprises about 1% to about 95% of the active ingredient, single-dose forms of administration preferably comprising about 20% to about 90% of the active ingredient and administration forms which are not single-dose preferably comprising about 5% to about 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The pharmaceutical compositions of the present disclosure are prepared in a manner known per se, for example by means of convential mixing, granulating, coating, dissolving or lyophilizing processes.

Preferably, solutions of the active ingredient, and in addition also suspensions or dispersions, especially isotonic aqueous solutions, dispersions or suspensions, are used, it being possible for these to be prepared before use, for example in the case of lyophilized compositions which comprise the active substance by itself or together with a carrier, for example mannitol. The pharmaceutical compositions can be sterilized and/or comprise excipients, for example preservatives, stabilizers, wetting agents and/or emulsifiers, solubilizing agents, salts for regulating the osmotic pressure and/or buffers, and they are prepared in a manner known per se, for example by means of convential dissolving or lyophilizing processes. The solutions or suspensions mentioned can comprise viscosity-increasing substances, such as sodium carboxymethylcellulose, carboxymethylcellulose, dextran, polyvinylpyrrolidone or gelatin.

Pharmaceutically acceptable forms include, for example, a gel, lotion, spray, powder, pill, tablet, controlled release tablet, sustained release tablet, rate controlling release tablet, enteric coating, emulsion, liquid, salts, pastes, jellies, aerosols, ointments, capsules, gel caps, or any other suitable form that will be obvious to one of ordinary skill in the art.

Suspensions in oil comprise, as the oily component, the vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, arachidinic acid, behenic acid or corresponding unsaturated acids, for example oleic acid, elaidic acid, euric acid, brasidic acid or linoleic acid, if appropriate with the addition of antioxidants, for example vitamin E, .beta.-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are therefore, for example: ethyl oleate, isopropyl myristate, isopropyl palmitate, "Labrafil M 2375" (polyoxyethylene glycerol trioleate from Gattefosee, Paris), "Labrafil M 1944 CS" (unsaturated polyglycolated glycerides prepared by an alcoholysis of apricot kernel oil and made up of glycerides and polyethylene glycol esters; from Gattefosee, Paris), "Labrasol" (saturated polyglycolated glycerides prepared by an alcoholysis of TCM and made up of glycerides and polyethylene glycol esters; from Gattefosee, Paris) and/or "Miglyol 812" (triglyceride of saturated fatty acids of chain length C8 to C12 from Huls AG, Germany), and in particular vegetable oils, such as cottonseed oil, almond oil, olive oil, castor oil, sesame oil, soybean oil and, in particular, groundnut oil.

The preparation of the injection compositions is carried out in the customary manner under sterile conditions, as are bottling, for example in ampoules or vials, and closing of the containers.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients.

Suitable carriers are, in particular, fillers, such as sugars, for example lactose, sucrose, mannitol or sorbitol cellulose preparations and/or calcium phosphates, for example tricalcium phosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinyl-pyrrolidine, and/or, if desired, desintegrators, such as the above mentioned starches, and furthermore carboxymethyl-starch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidine, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate.

By "controlled release" it is meant for purposes of the present disclosure that therapeutically active compound is released from the preparation at a controlled rate or at a specific site, for example, the intestine, or both such that therapeutically beneficial blood levels (but below toxic levels) are maintained over an extended period of time, e.g., providing a 12 hour or a 24 hour dosage form.

The term "rate controlling polymer" as used herein includes hydrophilic polymers, hydrophobic polymers or mixtures of hydrophilic and/or hydrophobic polymers that are capable of retarding the release of the compounds in vivo. In addition, many of the same polymers can be utilized to create an enteric coating of a drug, drug suspension, or drug matrix. It is within the skill of those in the art to modify the coating thickness, permeability, and dissolution characteristics to provide the desired controlled release profile (e.g., drug release rate and locus) without undue experimentation.

Examples of suitable controlled release polymers to be used in this disclosure include hydroxyalkylcellulose, such as hydroxypropylcellulose and hydroxypropylmethyl-cellulose; poly(ethylene)oxide; alkylcellulose such as ethycellulose and methylcellulose; carboxymethylcellulose; hydrophilic cellulose derivatives; polyethylene glycol; polyvinylpyrrolidone; cellulose acetate; cellulose acetate butyrate; cellulose acetate phthalate; cellulose acetate trimellitate; polyvinylacetate phthalate; hydroxypropylmethylcellulose phthalate; hydroxypropylmethylcellulose acetate succinate; poly(alkyl methacrylate); and poly(vinyl acetate). Other suitable hydrophobic polymers include polymers or copolymers derived from acrylic or methacrylic acid esters, copolymers of acrylic and methacrylic acid esters, zein, waxes, shellac and hydrogenated vegetable oils.

To ensure correct release kinetics, the controlled release preparation of this disclosure contains about 5 and 75% by weight, preferably about 20 and 50% by weight, more preferably about 30 to 45% by weight controlled release polymer(s) and about 1 to 40% by weight, preferably about 3 to 25% by weight active compounds. The controlled release preparation according to the disclosure can preferably include auxiliary agents, such as diluents, lubricants and/or melting binders. Preferably, the excipients are selected to minimize the water content of the preparation. Preferably, the preparation includes an antioxidant. Suitable diluents include pharmaceutically acceptable inert fillers such as microcrystalline cellulose, lactose, dibasic calcium phosphate, saccharides, and/or mixtures of any of the foregoing. The diluent is suitably a water soluble diluent. Examples of diluents include microcrystalline cellulose such as Avicel ph112, Avicel pH101 and Avicel pH102; lactose such as lactose monohydrate, lactose anhydrous, and Pharmatose DCL 21; dibasic calcium phosphate such as Emcompress; mannitol; starch; sorbitol; sucrose; and glucose. Diluents are carefully selected to match the specific formulation with attention paid to the compression properties. Suitable lubricants, including agents that act on the flowability of the powder to be compressed are, for example, colloidal silicon dioxide such as Aerosil 200; talc; stearic acid, magnesium stearate, and calcium stearate. Suitable low temperature melting binders include polyethylene glycols such as PEG 6000; cetostearyl alcohol; cetyl alcohol; polyoxyethylene alkyl ethers; polyoxyethylene castor oil derivatives; polyoxyethylene sorbitan fatty acid esters; polyoxyethylene stearates; poloxamers; and waxes.

To improve the stability in the controlled release preparation, an antioxidant compound can be included. Suitable antioxidants include sodium metabisulfite; tocopherols such as alpha, beta, or delta-tocopherol tocopherol esters and alpha-tocopherol acetate; ascorbic acid or a pharmaceutically acceptable salt thereof; ascorbyl palmitate; alkyl gallates such as propyl gallate, Tenox PG, Tenox s-1; sulphites or a pharmaceutically acceptable salt thereof; BHA; BHT; and monothioglycerol.

The controlled release preparation according to the disclosure preferably can be manufactured by blending the compounds with the controlled release polymer(s) and auxiliary excipients followed by direct compression. Other methods for manufacturing the preparation include melt granulation. Preferred melt granulation techniques include melt granulation together with the rate controlling polymer(s) and diluent(s) followed by compression of the granules and melt granulation with subsequent blending with the rate controlling polymer(s) and diluents followed by compression of the blend. As desired prior to compression, the blend and/or granulate can be screened and/or mixed with auxiliary agents until an easily flowable homogeneous mixture is obtained.

Oral dosage forms of the controlled release preparation according to the disclosure can be in the form of tablets, coated tablets, enterically coated tablets or can be multiparticulate, such as in the form of pellets or mini-tablets. If desired, capsules such as hard or soft gelatin capsules, can contain the multiparticulates. If desired, the multiparticulate oral dosage forms can comprise a blend of at least two populations of pellets or mini-tablets having different controlled-release in vitro and/or in vivo release profiles. If desired, one of the pellet or mini-tablet populations can comprise immediate release multiparticulate, such as multiparticulates formed by conventional means.

If desired, the controlled release matrix tablets or multiparticulates of this disclosure can be coated with a controlled release polymer layer so as to provide additional controlled release properties. Suitable polymers that can be used to form this controlled release layer include the rate controlling polymers listed above.

As desired, the tablets, pellets or mini-tablets according to the disclosure can be provided with a light-protective and/or cosmetic film coating, for example, film-formers, pigments, anti-adhesive agents and plasticizers. Such a film former may consist of fast-dissolving constituents, such as low-viscosity hydroxypropylmethylcelluose, for example Methocel E5 or D14 or Pharmacoat 606 (Shin-Etsu). The film coating may also contain excipients customary in film-coating procedures, such as light-protective pigments, for example iron oxide, or titanium dioxide, anti-adhesive agents, for example talc, and also suitable plasticizers such as PEG 400, PEG 6000, and diethyl phthalate or triethyl citrate.

The controlled release polymer of this disclosure may consist of a hydrogel matrix. For instance, the compounds can be compressed into a dosage form containing a rate controlling polymer, such as HPMC, or mixture of polymers which when wet will swell to form a hydrogel. The rate of release from this dosage form is controlled both by diffusion from the swollen tablet mass and by erosion of the tablet surface over time. The rate of release may be controlled both by the amount of polymer per tablet and by the inherent viscosities of the polymers used.

Dyes or pigments can be admixed to the tablets or coated tablet coatings, for example for identification or characterization of different doses of active ingredient.

Pharmaceutical compositions, which can be used orally, are also hard capsules of gelatin and soft, closed capsules of gelatin and a plasticizer, such as glycerol or sorbitol. The hard capsules can contain the active ingredient in the form of granules, mixed for example with fillers, such as maize starch, binders and/or lubricants, such as talc or magnesium stearate, and stabilizers if appropriate. In soft capsules, the active ingredient is preferably dissolved or suspended in suitable liquid excipients, such as greasy oils, paraffin oil or liquid polyethylene glycols or fatty acid esters of ethylene glycol or propylene glycol, it being likewise possible to add stabilizers and detergents, for example of the polyethylene sorbitan fatty acid ester type.

Other oral forms of administration are, for example, syrups prepared in the customary manner, which comprise the active ingredient, for example, in suspended form and in a concentration of about 5% to 20%, preferably about 10% or in a similar concentration which results in a suitable individual dose, for example, when 5 or 10 ml are measured out. Other forms are, for example, also pulverulent or liquid concentrates for preparing of shakes, for example in milk. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parenteral administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and if appropriate stabilizers. The active ingredient can also be present here in the form of a lyophilisate, if appropriate together with excipients, and be dissolved before parenteral administration by addition of suitable solvents. Solutions such as are used, for example, for parental administration can also be used as infusion solutions. Preferred preservatives are, for example. Antioxidants, such as ascorbic acid, or microbicides, such as sorbic or benzoic acid.

Ointments are oil-in-water emulsions, which comprise not more than 70%, but preferably 20-50% of water or aqueous phase. The fatty phase consists, in particular, hydrocarbons, for example vaseline, paraffin oil or hard paraffin's, which preferably comprise suitable hydroxy compounds, such as fatty alcohol's or esters thereof, for example cetyl alcohol or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerol, propylene glycol, sorbitol and/or polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example hydrogenated coconut-fatty acid triglycerides, or, preferably, hydrogenated oils, for example hydrogenated groundnut or castor oil, and furthermore fatty acid partial esters of glycerol, for example glycerol mono- and/or distearate, and for example, the fatty alcohols. They also contain emulsifiers and/or additives mentioned in connection with the ointments which increase uptake of water.

Creams are oil-in-water emulsions, which comprise more than 50% of water. Oily bases used are, in particular, fatty alcohols, for example lauryl, cetyl or stearyl alcohols, fatty acids, for example palmitic or stearic acid, liquid to solid waxes, for example isopropyl myristate, wool wax or beeswax, and/or hydrocarbons, for example vaseline (petrolatum) or paraffin oil. Emulsifiers are surface-active substances with predominantly hydrophilic properties, such as corresponding nonionic emulsifiers, for example fatty acid esters of poly alcohols or ethyleneoxy adducts thereof, such as polyglyceric acid fatty acid esters or polyethylene sorbitan fatty esters (Tweens), and furthermore polyoxyethylene fatty alcohol ethers or polyoxyethylene fatty acid esters, or corresponding ionic emulsifiers, such as alkali metal salts of fatty alcohol sulfates, for example sodium lauryl sulfate, sodium cetyl sulfate or sodium stearyl sulfate, which are usually used in the presence of fatty alcohols, for example cetyl stearyl alcohol or stearyl alcohol. Additives to the aqueous phase are, inter alia, agents which prevent the creams from drying out, for example poly alcohols, such as glycerol, sorbitol, propylene glycol and/or polyethylene glycols, and furthermore preservatives and odoriferous substances.

Pastes are creams and ointments having secretion-absorbing powder constituents, such as metal oxides, for example titanium oxide or zinc oxide, and furthermore talc and/or aluminum silicates, which have the task of binding the moisture or secretions present.

Foams are administered from pressurized containers and they are liquid oil-in-water emulsions present in aerosol for. As the propellant gases, halogenated hydrocarbons, such as chlorofluoro-lower alkanes, for example dichlorofluoromethane and dichlorotetrafluoroethane, or, preferably, non-halogenated gaseous hydrocarbons, air, N.sub.2 O, or carbon dioxide are used. The oily phases used are, inter alia, those mentioned above for ointments and creams, and the additives mentioned there are likewise used.

Tinctures and solutions usually comprise an aqueous-ethanolic base to which, humectants for reducing evaporation, such as poly alcohols, for example glycerol, glycols and/or polyethylene glycol, and re-oiling substances, such as fatty acid esters with lower polyethylene glycols, i.e. lipophilic substances soluble in the aqueous mixture to substitute the fatty substances removed from the skin with the ethanol, and, if necessary, other excipients and additives, are admixed.

Co-Adminstered Formulations

In an additional aspect, the description provides co-adminstered formulations comprising a peptide-oligourea hybrid compound as described herein, and at least one additional thereapeutic agent. The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects of the present disclosure, one or more of the present compounds described herein, are coadministered in combination with at least one additional bioactive agent. In particularly preferred aspects of the disclosure, the co-administration of compounds results in synergistic activity and/or therapy.

According to an embodiment, the agent to be co-administered is selected from the group comprising anti-cancer agents, antiviral agents (especially including anti-HIV agents and anti-HCV agents), antimicrobial agents, and antifungal agents. The anti-cancer agents can include, e.g., everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HD AC inhbitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatinib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdRi KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Methods of Treatment

In an additional aspect, the description provides a method of treating a disease, comprising administering to a subject in need thereof a composition comprising an effective amount of a peptide-oligourea hybrid as described herein, or a pharmaceutical formulation comprising the same and a pharmaceutically acceptable excipient, wherein composition is effective at treating or ameliorating at least one symptom of the disease. In certain embodiments, the disease is a metabolic disorder. In certain additional embodiments, the disease is diabetes.

The term "treatment" as used herein includes any treatment of a condition or disease in an animal, particularly a mammal, more particularly a human, and includes: (i) preventing the disease or condition from occurring in a subject which may be predisposed to the disease but has not yet been diagnosed as having it; (ii) inhibiting the disease or condition, i.e. arresting its development; relieving the disease or condition, i.e. causing regression of the condition; or (iii) ameliorating or relieving the conditions caused by the disease, i.e. symptoms of the disease.

The term "effective" is used to describe an amount of a compound, composition or component which, when used within the context of its intended use, effects an intended result.

The term "therapeutically effective amount" refers to that amount which is sufficient to effect treatment, as defined herein, when administered to a mammal in need of such treatment. The therapeutically effective amount will vary depending on the subject and disease state being treated, the severity of the affliction and the manner of administration, and may be determined routinely by one of ordinary skill in the art.

The disclosure also relates to a process or method for treatment of disease states. The oligourea compounds or chimeric compounds can be administered prophylactically or therapeutically as such or in the form of pharmaceutical compositions, preferably in an amount, which is effective against the diseases mentioned. With a warm-blooded animal, for example a human, requiring such treatment, the compounds are used, in particular, in the form of pharmaceutical composition. A daily dose of about 0.1 to about 5 g, preferably 0.5 g to about 2 g, of a compound of the present disclosure is administered here for a body weight of about 70 kg.

The description provides methods of treating a disease or disorder or ameliorating the effects of the same comprising the steps of administering to an individual in need thereof, a composition comprising an effective amount of a chimeric compound or a oligourea compound as described herein, and a pharmaceutically acceptable carrier or excipient, wherein the composition is effective for treating, preventing or ameliorating the effects of the disease or disorder.

The compounds or compositions described above are used for the manufacture of a medication for use in the treatment of a disease, disorder or condition. The term "disease involving deregulation of cell proliferation and/or angiogenesis" means, in the context of the disclosure, any human or animal disease affecting one or more organs.

Disease states of conditions which may be treated using compounds or compositions according to the present disclosure include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

Other disease states or conditions which may be treated by compounds or compositions according to the present disclosure include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barre syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Other exemplary diseases include, but are not limited to, rheumatoid arthritis, osteoarthritis, juvenile chronic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, atopic dermatitis, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein *purpurea*, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthopathy, arthropathy, Reiter's disease, psoriatic arthropathy, ulcerative colitic arthropathy, enteropathic synovitis, *chlamydia, yersinia* and *salmonella* associated arthropathy, spondyloarthopathy, atheromatous disease/arteriosclerosis, atopic allergy, autoimmune bullous disease, pemphigus vulgaris, pemphigus *foliaceus*, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjodgren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis *nigricans*, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasculitis of the kidneys, lyme disease, discoid lupus erythematosus, male infertility idiopathic or NOS, sperm autoimmunity, multiple sclerosis (all subtypes), insulin-dependent diabetes mellitus, sympathetic ophthalmia, pulmonary hypertension secondary to connective tissue disease, Goodpasture's syndrome, pulmonary manifestation of polyarteritis *nodosa*, acute rheumatic fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis and vitiligo. The human antibodies, and antibody portions of the disclosure can be used to treat autoimmune diseases, in particular those associated with inflammation, including, rheumatoid spondylitis, allergy, autoimmune diabetes, autoimmune uveitis.

Still additional disease states or conditions which can be treated by compounds or compositions according to the present disclosure include aceruloplasminemia, Achondrogenesis type II, achondroplasia, Acrocephaly, Gaucher disease type 2, acute intermittent *porphyria*, Canavan disease, Adenomatous Polyposis *Coli*, ALA dehydratase deficiency, adenylosuccinate lyase deficiency, Adrenogenital syndrome, Adrenoleukodystrophy, ALA-D *porphyria*, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alstrom syndrome, Alexander disease, Amelogenesis imperfecta, ALA dehydratase deficiency, Anderson-Fabry disease, androgen insensitivity syndrome, Anemia Angiokeratoma *Corporis Diffusum*, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome#arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dube syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic *porphyria*), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic *porphyria*, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic *porphyria*, erythropoietic protoporphyria, erythropoietic uroporphyria, Friedreich's ataxia, familial paroxysmal polyserositis, *porphyria cutanea tarda*, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic *porphyria*), haemochromatosis, Hallgren syndrome, sickle cell anemia, hemophilia, hepatoerythropoietic *porphyria* (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysyl-hydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis *nigricans* (SADDAN), Li-Fraumeni syndrome, sarcoma, breast, leukemia, and adrenal gland (SBFA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic *porphyria* (variegate *porphyria*), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alstrom syndrome), Vrolik disease, Waardenburg syndrome, Warburg Sjo Fledelius Syndrome, Weissenbacher-Zweymuller syndrome, Wolf-Hirschhom syndrome, Wolff Periodic disease, Weissenbacher-Zweymuller syndrome and Xeroderma pigmentosum, among others.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

The methods herein include administering to the subject (including a subject identified as in need of such treatment) an effective amount of a compound described herein, or a composition described herein to produce a desired effect. Identifying a subject in need of such treatment can be in the judgment of the subject or a health care professional and can be subjective (e.g., opinion) or objective (e.g., measurable by a test or diagnostic method). The therapeutic methods of the disclosure, which include prophylactic treatment, in general comprise administration of a therapeutically effective amount of at least one of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like).

In another aspect, the present description provides methods of making and using the peptide-oligourea hybrid compounds or the oligourea compounds as described herein. For example, in certain aspects, the peptide-oligourea hybrid compounds or the oligourea compound as described herein can be used as a diagnostic agent.

In one embodiment, the disclosure provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with protein-expression related disease (including misfolding), in which the subject has been administered a therapeutic amount of a compound or a composition herein sufficient to treat the disease or symptoms thereof. The level of Marker determined in the method can be compared to known levels of Marker in either healthy normal controls or in other afflicted patients to establish the subject's disease status. In certain embodiments, a second level of Marker in the subject is determined at a time point later than the determination of the first level, and the two levels are compared to monitor the course of disease or the efficacy of the therapy. In certain embodiments, a pre-treatment level of Marker in the subject is determined prior to beginning treatment according to this disclosure; this pre-treatment level of Marker can then be compared to the level of Marker in the subject after the treatment commences, to determine the efficacy of the treatment.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier. The compound is conveniently administered in any suitable unit dosage form, including but not limited to one containing less than lmg, 1 mg to 3000 mg, preferably 5 to 500 mg of active ingredient per unit dosage form. An oral dosage of about 25-250 mg is often convenient. The active ingredient is preferably administered to achieve peak plasma concentrations of the active compound of about 0.00001-30 mM, preferably about 0.1-30 µM.

This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent. The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Methods of Preparation

In another aspect, the present description provides methods of making and using the compounds or compositions of the description. For example, in one embodiment, the description provides a method of making an oligourea compound composition of the description comprising fabricating a peptide-oligourea hybrid foldamer compound.

Additional, exemplary methods for performing the synthesis of compounds as described herein are provided below.

It is understood that the examples and embodiments described herein are for illustrative purposes only and that various substitutions, modifications or changes in light thereof will be suggested to persons skilled in the art and are included within the spirit and purview of this application and are considered within the scope of the appended claims. The following examples are given by way of example of the preferred embodiments, and are in no way considered to be limiting to the disclosure. For example, the relative quantities of the ingredients may be varied to achieve different desired effects, additional ingredients may be added, and/or similar ingredients may be substituted for one or more of the ingredients described. All publications, patents, and patent applications cited herein are hereby incorporated by reference in their entirety for all purposes.

EXAMPLES

Peptide-oligourea hybrids design and functional assay. Peptide-oligourea hybrid design started with GLP-1-NH$_2$ and the introduction of a glycine in position 2 of GLP-1 instead of alanine (GLP-1-G$^2$, Compound 1 and SEQ ID NO: 1) as it is known to prevent DPP-4 degradation.[31-33] We then identified the amount of consecutive amino acid residues that can be replaced by ureido units. This aspect was important considering GLP-1 has key interactions with GLP-1R at both end of the peptide.[27,30] If an oligourea portion placed in the middle of the peptide induced a torsion or an elongation that is not exactly the same as the polypeptide it replaces, a drastic negative impact on the affinity would be expected. We thus decided to start our investigation by replacing four consecutive amino acids (X$_4$) with three consecutive ureido residues (X$^u_3$) based on our model suggesting that this combination gives the best overlaps of the terminal atoms (FIGS. 2A-2C). It is noteworthy that the diameter of the triad helix turn is slightly larger than the peptide α-helix turn and it should be taken into account when designing hybrids.

TABLE 1

Bioactivity of GLP-1 and cognate peptide-oligourea analogues in cAMP production functional assay.

| SEQ ID NO./Comp. # | Sequence | Compound | EC50 (nM)[a] | SE (nM)[b] | Potency (%)[c] |
|---|---|---|---|---|---|
| 26 | H—HAEGT FTSDV SSYLE GQAAK EFIAW LVKGR G—OH | GLP-1 | 0.10[d] | 0.01[e] | 250 |
| 1 | H—HGEGT FTSDV SSYLE GQAAK EFIAW LVKGR G—NH2 (1) | GLP-1-G$^2$ (GG2) | 0.24 | 0.06 | 100 |
| 26 | $^H$HAEGTFTSDVSSYLEGQAAKEFIAWLVKGRG$^{OH}$ | GLP-1 | 0.10[d] | 0.01[e] | 250 |
|  | $^H$HGEGTFTSDVSSYLEGQAAKEFIAWLVKGRG$^{NH_2}$ | GLP-1-G$^2$ (GG2) | 0.24 | 0.06 | 100 |
| 2 | $^H$HGEGTFTSD░░░░YLEGQAAKEFIAWLVKGRG$^{NH_2}$ | GG2[D$^{U\alpha}$A$^U$A$^U$]$^{9-12}$ | 13 | 3 | 2 |
| 3 | $^H$HGEGTFTSDA░░░░LEGQAAKEFIAWLVKGRG$^{NH_2}$ | GG2[A$^U$A$^U$A$^U$]$^{10-13}$ | 650 | 100 | 0.04 |
| 4 | $^H$HGEGTFTSDV░░░░EGQAAKEFIAWLVKGRG$^{NH_2}$ | GG2[A$^U$A$^U$A$^U$]$^{11-14}$ | 97 | 9 | 0.2 |
| 5 | $^H$HGEGTFTSDV░░░░EGQAAKEFIAWLVKGRG$^{NH_2}$ | GG2[A$^U$Y$^U$A$^U$]$^{11-14}$ | 1.6 | 0.5 | 15 |
| 6 | $^H$HGEGTFTSDVS░░░░GQAAKEFIAWLVKGRG$^{NH_2}$ | GG2[A$^U$A$^U$A$^U$]$^{12-15}$ | >10000 | N/A | <0.01 |
| 7 | $^H$HGEGTFTSDVSS░░░░QAAKEFIAWLVKGRG$^{NH_2}$ | GG2[A$^U$A$^U$A$^U$]$^{13-16}$ | >10000 | N/A | <0.01 |
| 8 | $^H$HGEGTFTSDVSSY░░░░AAKEFIAWLVKGRG$^{NH_2}$ | GG2[A$^U$A$^U$A$^U$]$^{14-17}$ | 353 | 58 | 0.07 |
| 9 | $^H$HGEGTFTSDVSSY░░░░AAKEFIAWLVKGRG$^{NH_2}$ | GG2[Y$^U$E$^U$A$^U$]$^{14-17}$ | 0.18 | 0.07 | 135 |
| 10 | $^H$HGEGTFTSDVSSYL░░░░AKEFIAWLVKGRG$^{NH_2}$ | GG2[A$^U$A$^U$A$^U$]$^{15-18}$ | 123 | 23 | 0.2 |
| 11 | $^H$HGEGTFTSDVSSYL░░░░AKEFIAWLVKGRG$^{NH_2}$ | GG2[E$^U$A$^U$A$^U$]$^{15-18}$ | 1.9 | 0.4 | 13 |
| 12 | $^H$HGEGTFTSDVSSYLE░░░░KEFIAWLVKGRG$^{NH_2}$ | GG2[A$^U$A$^U$A$^U$]$^{16-19}$ | 240 | 36 | 0.1 |
| 13 | $^H$HGEGTFTSDVSSYLEG░░░░EFIAWLVKGRG$^{NH_2}$ | GG2[A$^U$A$^U$A$^U$]$^{17-20}$ | 1603 | 187 | 0.01 |
| 14 | $^H$HGEGTFTSDVSSYLEGQ░░░░FIAWLVKGRG$^{NH_2}$ | GG2[A$^U$A$^U$A$^U$]$^{18-21}$ | 4.1[f] | 0.9[e] | 6 |
| 15 | $^H$HGEGTFTSDVSSYLEGQA░░░░IAWLVKGRG$^{NH_2}$ | GG2[A$^U$A$^U$A$^U$]$^{19-22}$ | >10000 | N/A | <0.01 |
| 16 | $^H$HGEGTFTSDVSSYLEGQAAKE░░░░LVKGRG$^{NH_2}$ | GG2[F$^{U\alpha}$I$^U$A$^U$]$^{22-25}$ | 62 | 28 | 0.4 |
| 17 | $^H$HGEGTFTSDVSSYLEGQAAKEF░░░░VKGRG$^{NH_2}$ | GG2[A$^U$A$^U$A$^U$]$^{23-26}$ | 3926 | 2751 | 0.01 |
| 18 | $^H$HGEGTFTSDVSSYLEGQAAKEFI░░░░KGRG$^{NH_2}$ | GG2[A$^U$A$^U$A$^U$]$^{24-27}$ | >10000 | N/A | <0.01 |
| 19 | $^H$HGEGTFTSDVSSYLEGQAAKEFIA░░░░GRG$^{NH_2}$ | GG2[A$^U$A$^U$A$^U$]$^{25-28}$ | 368 | 169 | 0.07 |
| 20 | $^H$HGEGTFTSDVSSYLEGQAAKEFIAW░░░░RG$^{NH_2}$ | GG2[A$^U$A$^U$A$^U$]$^{26-29}$ | 26 | 6 | 0.9 |
| 21 | $^H$HGEGTFTSDVSSYLEGQAAKEFIAWL░░░░G$^{NH_2}$ | GG2[A$^U$A$^U$A$^U$]$^{27-30}$ | 2.8 | 0.9 | 8 |

TABLE 1-continued

Bioactivity of GLP-1 and cognate peptide-oligourea analogues in cAMP production functional assay.

| SEQ ID NO./Comp. # | Sequence | Compound | EC50 (nM)$^a$ | SE (nM)$^b$ | Potency (%)$^c$ |
|---|---|---|---|---|---|
| 22 | $^H$HGEGTFTSDVSSYLEGQAAKEFIAWLVAAA$^{NH}$2 | GG2[A$^U$A$^U$A$^U$]$^{28-31}$ | 1.2 | 0.3 | 19 |
| 23 | $^H$HGEGTFTSDVSSYAAAAAIAWLVKGRG$^{NH}$2 | GG2[Y$^U$E$^U$A$^U$A$^U$A$^U$]$^{14-21}$ | 3.4 | 0.8 | 7 |

Oligourea inserts (triads and hexads) are shown as green boxes. The highlighted amino acids in the GLP-1 sequence generated the highest decrease of activity in the Ala scan: bold, underline = very high decrease, underline = high decrease.
$^a$GLP-1R potency (EC$_{50}$).
$^b$Standard error (SE) on the EC$_{50}$.
$^c$Percentage of potency compare to GLP-1-G$^2$.
$^d$Mean value of 26 experiments.
$^e$Standard error of the mean (SEM) on the EC$_{50}$.
$^f$Mean value of 4 experiments.

Next, we turned our attention to the side chains of the removed tetrapeptide. Our model suggested that the projection of the side chains of X$^u$ residues would not be the same as the native X residues they replaced (FIG. 2B). Indeed, examination of the model suggested that the side chain of X$^U$1 did not project in the same direction as in X1. However, it suggested that a ureido residue with its side chain shifted to the second backbone methylene (i.e. α-C)[18] would give a similar projection. The second side chain (X$^u$2) gave the best fit with the corresponding α-amino acid side chain (X2) based on this model. On the other hand, the third amino acid side chain seemed to be the least imitable as it is superimposed with a urea nitrogen of the third ureido residue X$^u$3. However, our model also suggested that this third ureido residue could mimic the fourth amino acid residue (X4) by changing the substitution pattern (shift to the second methylene—α-C). Overall, our model suggested that mimicking the precise projection of α-amino acid side chains was possible although not necessary trivial.

Considering the relative difficulty to select the most appropriate side chains in ureido units to mimic a given tetrapeptide segment with high fidelity, we thus decided to start with an Ala$^u$ triad (A$^U$A$^U$A$^U$) scan for simplification. The objective was to avoid any negative impact of the amino urea side chains on the potency so the observed activity would correlate the loss of affinity predicted from the Ala scan (FIG. 3)[48,49] A lower activity than predicted would mean a negative impact coming from the backbone modification. In our first round of syntheses, the known helical portion of GFP-1 spanning residues 9 to 31 was scanned with Ala$^u$ triads (A$^U$A$^U$A$^U$). We avoided however to synthesise hybrids lacking D9 or F22, considering that these amino acids are requisite for potency (Table 1). All compounds were synthesized using standard solid phase synthesis techniques and μwave assistance.[22]

The agonistic activity of these hybrids were obtained by functional assays using cells expressing the GFP-1R and by measuring the receptor-mediated cAMP produced (see supporting information). As expected, GFP-1-G$^2$ (1) was 2.5 times less potent than GFP-1, with still a 50% effective concentration (EC$_{50}$) of 0.24 nM. Interestingly, many hybrids from the Ala$^u$ triad scan proved to be potent, demonstrating the good overlaps of the oligourea backbone with the peptide backbone. The most active hybrids were selected and native side chains were introduced in the oligourea triads in new rounds of synthesis with focus on recovering the most important side chain interactions: D9, Y13, E15, F22, and I23. Table 1 shows a selection of the most representative results obtained in this study. Interestingly, in most cases the reintroduction of the native side chains improved the potency of the GLP-1-oligourea hybrids. GG2[Y$^U$E$^U$A$^U$]$^{14-17}$ (9) even gave a better affinity (0.18 nM) than the native peptide 1 (0.24 nM). It is noteworthy that hybrids GG2[D$^{uα}$A$^u$A$^u$]$^{9-12}$ (2, 13 nM) and GG2[F$^{uα}$I$^u$A$^u$]$^{22-25}$ (16, 62 nM) which contain native side chains and shifted substitution pattern still preserve substantial affinity with GLP-1R, although with over a hundred fold loss compared to the native peptide. Nevertheless, considering the importance of the modifications, the mere observation that oligourea triads can mimic those capital interactions is remarkable. We also investigated the possibility to introduce two successive triads by synthesizing compound GG2[Y$^u$E$^u$A$^u$A$^u$A$^u$]$^{14-21}$ (23), which comes from the combination of 9 (0.18 nM) and 14 (4.1 nM). We were delighted to find that 23 was still active (3.4 nM) with a similar potency to 14, considering that 25% of the GLP-1 sequence was replaced by oligoureas.

Enzymatic and mouse plasma degradation studies. Having in hands active hybrids, we then turn our attention to their stability toward proteolysis. Since homooligoureas are fully resistant to proteases,[20] improved proteolytic protection was expected for hybrids compare to their native peptide 1. As mentioned above, the two main identified proteases for the degradation of GLP-1 in vivo are DPP-4 and NEP-24.11. As the glycine in position 2 of our analogues prevents the specific DDP-4 cleavage between residues 2 and 3, our attention was turned toward the later. NEP 24.11 (Neutral endopeptidase 24.11, also known as Neprilysin, CD 10, MME, and CALLA) is an unspecific membrane protease that quickly cleaves GLP-1 at multiple sites.[35] It was showed that a GLP-1 analogue with improved half-life in a NEP 24.11 degradation assay had prolonged action in mice, therefore making this assay relevant to evaluate the potential efficacy in vivo of our compounds.[40] In addition to NEP 24.11, mouse plasma was also utilized to assess the stability or our compounds.

TABLE 2

NEP 24.11 and mouse plasma degradation assays.

| SEQ ID NO. | Compound | Potency (%)[a] | NEP 24.11 $t_{1/2}$ (h)[b] | SEM (h)[c] | Mouse Plasma $t_{1/2}$ (min)[d] | SEM (min)[e] | In vivo activity[f] |
|---|---|---|---|---|---|---|---|
| 1 | GLP-1-G$^2$-NH$_2$ (GG2) | 100 | 3.6 | 0.1 | 16 | 1 | + |
| 2 | GG2[D$^{u\alpha}$A$^u$A$^u$]$^{9-12}$ | 2 | 4.4 | 0.4 | 17 | 1 | |
| 5 | GG2[A$^u$Y$^u$A$^u$]$^{11-14}$ | 15 | 2.9 | 0.3 | 23 | 3 | + |
| 9 | GG2[Y$^u$E$^u$A$^u$]$^{14-17}$ | 135 | 3.0 | 0.2 | 17 | 1 | + |
| 11 | GG2[E$^u$A$^u$A$^u$]$^{15-18}$ | 13 | 3.9 | 0.4 | 31* | 3 | |
| 14 | GG2[A$^u$A$^u$A$^u$]$^{18-21}$ | 6 | 4.9 | 0.8 | 38*** | 2 | +++ |
| 16 | GG2[F$^{u\alpha}$I$^u$A$^u$]$^{22-25}$ | 0.4 | 1.8 | 0.1 | 38*** | 5 | |
| 22 | GG2[A$^u$A$^u$A$^u$]$^{28-31}$ | 19 | 4.5 | 0.5 | >60*** | na | +++ |
| 23 | GG2[Y$^u$E$^u$A$^u$A$^u$A$^u$A$^u$]$^{14-21}$ | 7 | 6.1* | 0.9 | 39*** | 5 | +++ |

[a]Percentage of potency (cAMP production) compared to GLP-1-G$^2$ (see Table 1). [b]Half-life of the GLP-1 analogues in NEP 24.11 degradation assay: mean value of three replicates. [c]Standard error of the mean on the NEP 24.11 $t_{1/2}$. [d]Half-life of the GLP-1 analogues in mouse plasma degradation assay: mean value of four replicates. [e]Standard error of the mean on the mouse plasma $t_{1/2}$. [f]Indicator of in vivo activity. + = active, + + + = more active. (one way anova with Dunnett's multiple comparison test: *p < 0,05; ***p < 0,001)

Figure 32:
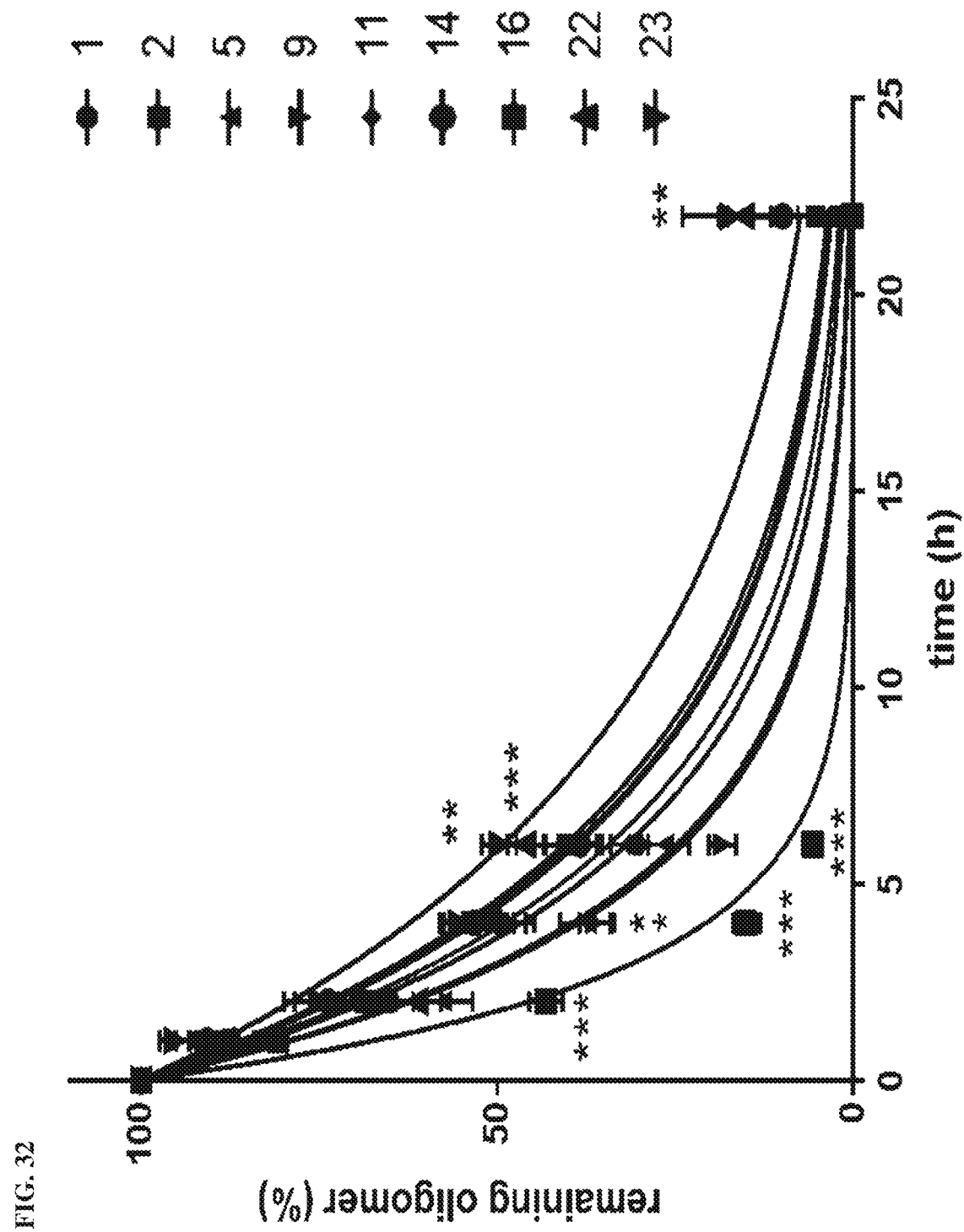
FIG. 32. Demonstrates the enzymatic degradation by NEP 24.11 of the respective peptides (SEQ ID NO: 2, 3, 6, 10, 12, 15, 17, 23, and 24). (two-way anova and Bonferroni post test: *$p<0.05$;  $p<0.01$; * $p<0.001$).

The half-lives of compounds 1, 2, 5, 9, 11, 14, 16, 22, and 23 in presence of NEP 24.11 and in presence of mouse plasma were determined by following the decay of the analogues by LCMS (Table 2). In the NEP 24.11 degradation assay, the native peptide 2 had a half-life of 3.6 h and unfortunately the hybrids 5, 9, and 16 showed diminished half-lives of 2.9 h, 3.0 h and 1.8 h respectively. Although these $t_{1/2}$ values were not significantly different from the $t_{1/2}$ of peptide 1 (3.6 h), statistical significance was obtained at the 4 h time point for these three hybrids demonstrating their lower stability (FIG. 32). Those results were intriguing, as we did not expect lower proteolytic protection for some hybrids. Further investigations showed no indication that the cleavage sites for the destabilized hybrids were located in or next to the oligourea triads making it more puzzling. Nevertheless, in two cases (22, 23) the permutation of 4 amino acids for an oligourea triad improved significantly the proteolytic protection of the hybrids (Table 2 and FIG. 32). It is also noteworthy that the analogue 23 where 8 amino acids were replaced by 2 triads had a significant increase of its half-life.

In mouse plasma degradation assay, the native peptide 1 had a half-life of 16 min and hybrids 2, 5, and 9 had similar $t_{1/2}$ of 17, 23 and 17 min respectively. Interestingly, hybrids 11, 14, 16, 22, and 23 had significantly longer half-lives. In the case of 22, a half-life of >60 min was observed, which represents over 3.8-folds improvement compared to peptide 1. Over the eight hybrids selected, five had improved stability in mouse plasma with the insertion of the triad at various positions on the peptide. The proteolytic stability to NEP 24.11 could predict mostly the results in mouse plasma. The next step was to investigate if these improvements in half-lives could be transposed in vivo.

In vivo studies. Although improving the proteolytic protection or the plasmatic stability of some hybrids represented a significant milestone, the most important question remained: are those improvements reflected in vivo? To answer this important question we conducted three sets of studies.

In the first study, we evaluated the effect of the analogues on the blood glucose concentration of normal mice (FIG. 4). The fed mice were treated with the analogues and their blood glucose concentration was monitored before and after dosing for 6 h. The native peptide GLP-1-G$^2$ (1) showed a decreased of blood glucose concentration after 30 min, proving its efficacy in vivo, although for a short time as a rapid raise to the initial concentration level is observed after 1 h. Hybrids 5 and 9 showed efficacy but no improvement, indicated by a similar blood glucose curve to peptide 1 (FIG. 4A). Hybrids 2, 11, and 16 showed no activity (FIG. 4B) since no initial drop in blood glucose concentration was observed and the curves resembled the vehicle one. Most interestingly, hybrids 14, 22, and 23 showed an improved efficacy compare to the native peptide 1 (FIG. 4C). Indeed, a decrease of blood glucose concentration is observed after 30 min and the effect is preserved for 4 h after dosing.

These results were well predicted by the plasma stability of the hybrids as all the compounds (2, 5, and 9) with similar plasma stability to peptide 1 gave comparable results in vivo. The compounds with lower potencies 2 (2%) and 16 (0.4%) showed no effect after 30 min and were therefore less effective than peptide 1 (100%), although 16 had longer half-life in plasma (16 vs 38 min). This indicates that passing a certain threshold, the potency is just not good enough to produce an observable effect. In the case of hybrid 11, no effect was observed on the blood glucose after 30 min of the injection. These results were more difficult to explain as the mouse plasma half-life of 11 is prolonged (31 min) and the potency (13%) is comparable to 14 (6%), 22 (19%) and 23 (7%). As expected, the three best compounds in vivo, 14, 22, and 23, had all (1) improved stability in NEP 24.11 degradation assays, (2) prolonged half-lives in mouse plasma and (3) decent potency. This is noteworthy as these analogues are at least 10-fold less potent then GFP-1-G$^2$ (2), meaning that even if at least 10 times more compound is required to get the same activity in vitro, they have a significant longer acting period. Interestingly, the analogue 24 with six consecutive ureido residues proved to be efficient despite its 7% potency compared to GFP-1-G$^2$ (2).

In order to validate our results that the pharmaceutical properties of peptide 2 can be improved by substituting amino acids with oligourea triads, we conducted a series of IPGTT studies on the three best hybrids 14, 22, and 23 with peptide 1 as control (FIGS. 5A1, 5A2, 5B1, 5B2, 5C1, 5C2, 5D1, and 5D2). In the first study, fasted healthy mice were submitted to an intra peritoneal glucose tolerance test (IP-GTT) 5 min after dosing 1 and 14 in order to validate the activity of the reference peptide 1. As expected both analogues were active, although 1 had a slightly higher AUC (FIGS. 5A1 and 5A2). Indeed, after 60 min of the glucose challenge, and therefore 65 min after dosing, 1 showed no more significant effect compare to the vehicle while 14 was still active, as expected from the blood glucose study (FIG. 4B). In a second study, an IPGTT was performed 30 min after i.v. injections of 1, 14 and the vehicle (FIGS. 5B1 and 5B2). An effect was observed at T0 before the glucose challenge but already after 30 min (60 min after dosing) there was no significant effect on the blood glucose for peptide 1 in agreement with previous IPGTT study. So when performing an IPGTT after 30 min of the dosing, the native peptide 1 was already inactive while hybrid 14 demonstrated full activity as predicted again from the blood glucose study. A further IPGTT study was done with a glucose challenge after 2 h of the dosing to investigate the prolong activity of hybrids 14, 22, and 23 (FIGS. 5C1 and 5C2). The native peptide 1 had an IPGTT curve similar to the vehicle as expected from previous studies. In contrast, the curve of hybrids 14, 22, and 23 showed a good control of the blood glucose concentration during the IPGTT which is reflected in the AUC. An IPGTT was then performed after 4 h of dosing with compounds 1, 14, and 22 (FIGS. 5D1 and 5D2). Almost no rise in the blood glucose was observed at 30 min post glucose challenge and the effect continued up to 120 min showing that hybrids 14 and 22 are still active after 6 h of the treatment.

To gain additional insight into the pharmacological consequences of modifying the peptide backbone with oligourea triads, we conducted a pharmacokinetic study with 1 and 22. In good agreement with the mouse plasma study and the pharmacodynamics data, hybrid 23 had a longer half-life compared to peptide 1 (FIG. 6) presumably because it has a better proteolytic stability, although other factors might be involved. The NEP study probably indicates the trend while not being the actual enzyme that determines the in vivo half-life of our analogues. All in all, these results clearly show that the activity of peptide 1 in vivo can be prolonged using the oligoureas triads strategy by improving its pharmacodynamics and pharmacokinetics properties.

Figures 37A, 37B:
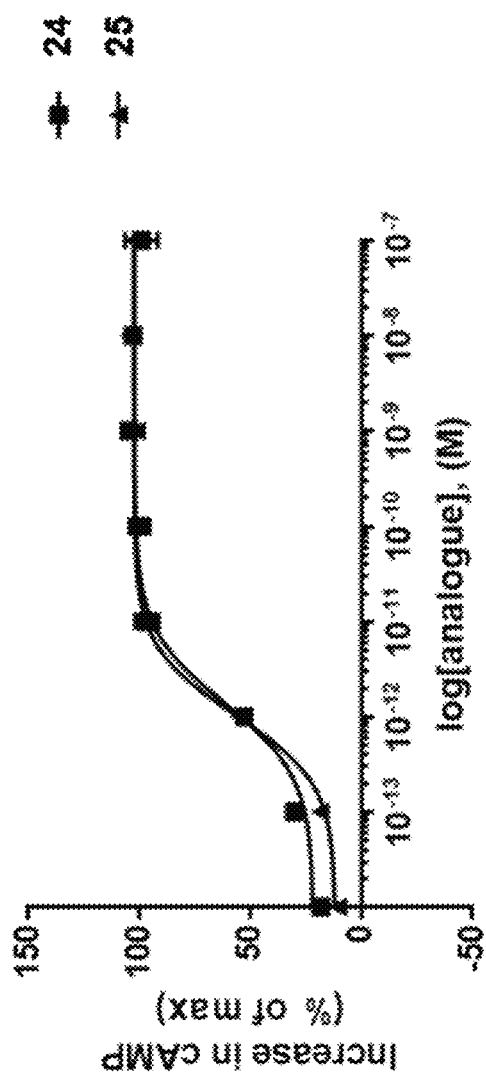
FIGS. 37A and 37B. Demonstrates the concentration-response curve (receptor-mediated cAMP produced) for EC50 determination of oligomer 24 and 25 in cells expressing the GLP-1R (37A). (37B) EC50 values and standard error of the mean values.
Figure 38A:
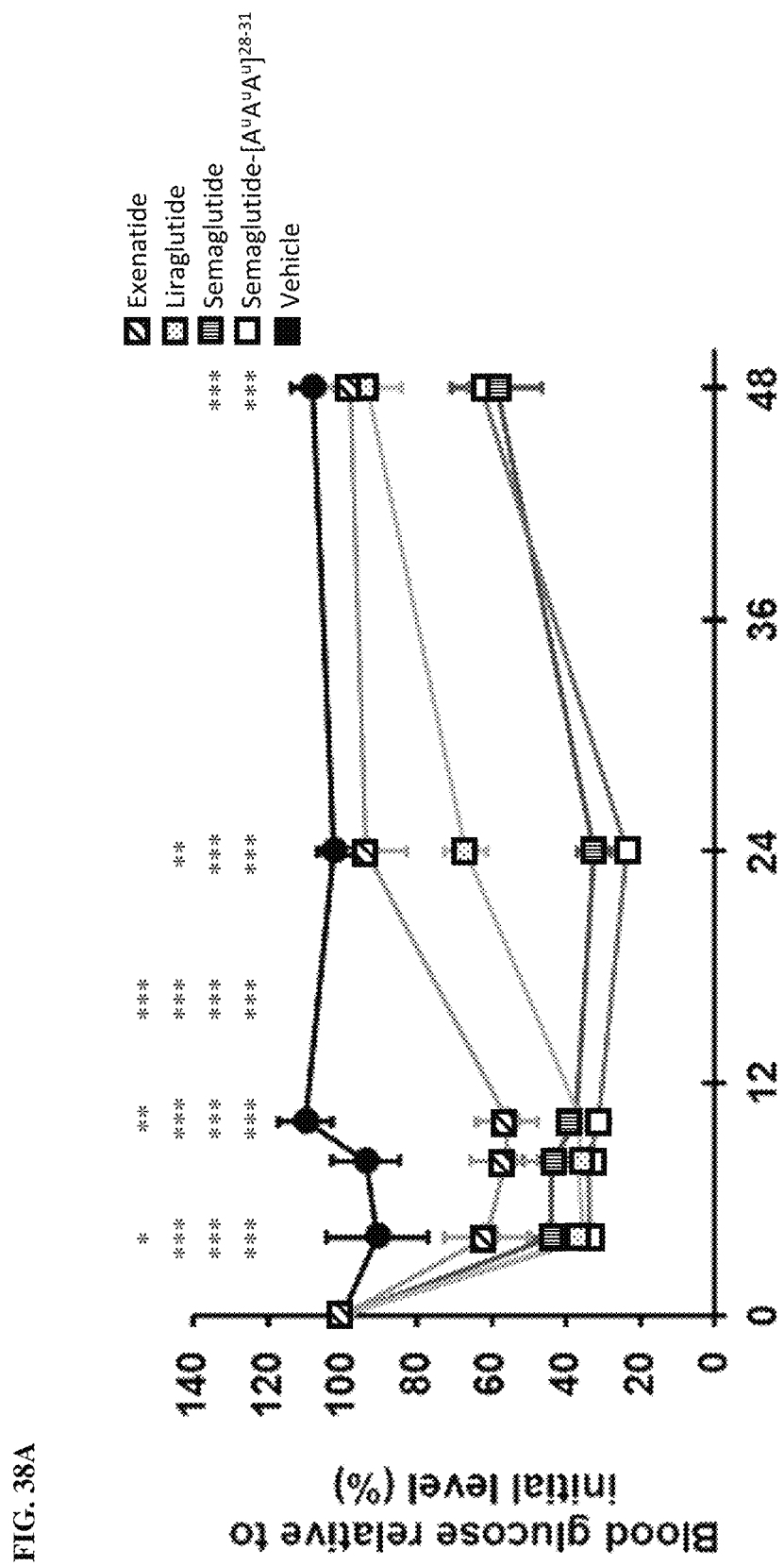
FIGS. 38A, 38B, and 38C. (38A, 38B) Blood glucose concentration in db/db mice (male, 40-45 g, n=5) before and after dosing: 200 µg/kg (50 nmol/kg) intra peritoneal. Formulation: 20 µg/mL in PBS 1×. The dosing was done at T0. (38B) AUC of the IPGTT curves. (38C) Pancreatin degradation assay, (two-way anova and Bonferroni post test: * $p<0.05$;  $p<0.01$; * $p<0.001$; one way anova with Dunnett's multiple comparison test: # $p<0.05$; ###$p<0.001$)
Figure 38C:
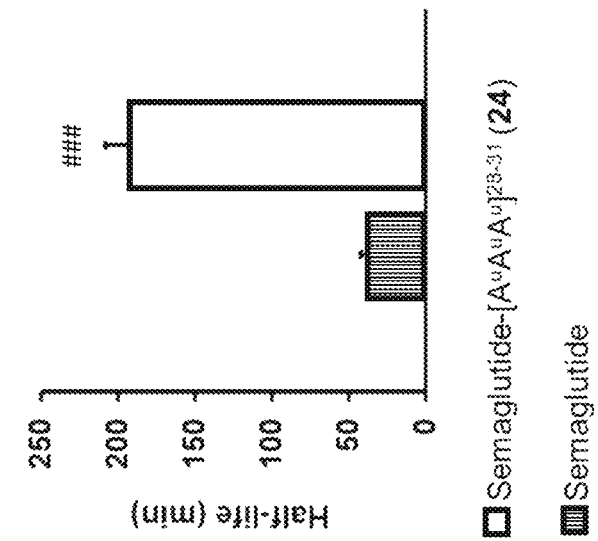
Figure 38B:
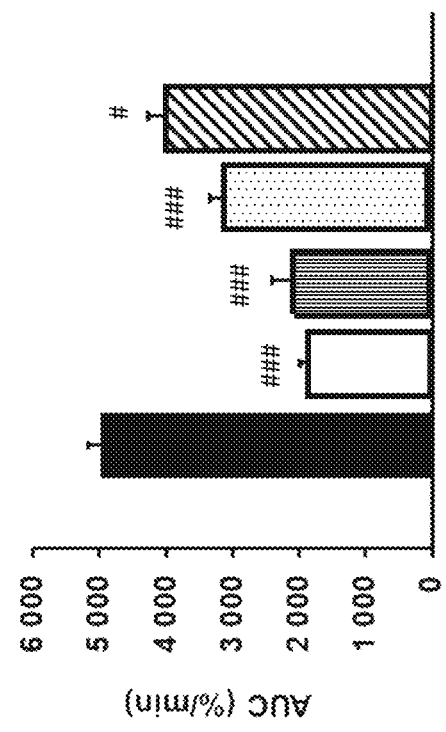

With that proof of concept in hand, we then investigated the possibility of combining the peptide/oligourea hybrid approach with the protraction strategy, which consists of functionalizing a peptide with a fatty acid chain to promote its binding to albumin and prolong its in vivo half-life. Semaglutide is a GLP-1 analogue with an 2-aminoisobutyric (Aib) in position 2 and a C18 chain linked to $K^{20}$ through a small PEG spacer which was accepted by the FDA in 2018 for the treatment of diabetes as a once weekly treatment and is presently in phase 3 clinical trial for a once daily oral treatment.[50,51] We synthesized hybrid 24 which is a semaglutide analogue with an oligourea fragment replacing the four last amino acids (semaglutide-[$A^U A^U A^U$]$^{28\text{-}31}$) like in hybrid 22. In vitro (cAMP production functional assay), hybrid 24 was found to be equally potent to semaglutide (FIGS. 37A and 37B). The pharmacodynamics properties of 24 were next assessed in a study on db/db mice using FDA approved exenatide, liraglutide and semaglutide as positive controls. A single dose of analogues or placebo was injected intra peritoneal and the blood glucose was followed over time. After 48 h, hybrid 24 and semaglutide (25) were still active while exenatide and liraglutide showed no more significant activity. Although hybrid 24 and semaglutide (25) showed similar activities in vitro and in vivo (FIGS. 38A-38C), it is noteworthy that hybrid 24 displays a longer half-life than semaglutide in mouse plasma (160 vs 11 h, FIGS. 34A-34C) and pancreatin (3.2 vs 0.63 h, FIGS. 38C and 35A-35C). Because pancreatin degradation assays are relevant to predict the stability of peptides in the gastrointestinal tract,[52] our data thus suggest that hybrid 24 could be suitable for oral administration and the peptide/oligourea hybrid approach reported here could be used to improve oral delivery of some peptide-based drugs.

In summary, a new and simple approach to modify and modulate the properties of bioactive peptide helices using small foldamer inserts was developed. It consists of replacing 4 consecutive amino acid residues in the sequence of an α-helical peptide by an α-helicomimetic oligourea segment of 3 residues to generate the analogous peptide-oligourea hybrid. Here, the method was applied in a systematic fashion to the 31 amino acid peptide GFP-1 to generate a series of GFP-1-oligourea hybrids among which potent agonists of GFP-1R were identified. Agonists of GFP-1R have proved to be potent treatment against type 2 diabetes mellitus and are promising for other indications such as obesity, NASH, and Alzheimer's disease. It is noteworthy that three hybrids out of the eight tested in mice had significantly prolonged duration of action. This prolonged effect was correlated with both NEP 24.11 and mouse plasma degradation studies, suggesting an increased stabilization towards other peptidases present in the organism. The strategy was then applied to semaglutide, a FDA approved GLP-1 analogue, to generate hybrid 24 and we showed that not only the in vivo activity was preserved, but the stability toward pancreatin was improved opening the way for improvement in oral administration. Overall, this study shows that replacing 4 consecutives amino acid residues with an ureido triad of similar dimension and geometry in a peptide α-helix is a good strategy to improve its pharmaceutical properties. We expect this approach to be useful for the development of new peptide therapeutics and we are currently evaluating its generalization to other peptide sequences and protein targets of therapeutic interest.

Synthesis of Exemplary Oligoureas

Synthesis of GLP-1 analogues. Compounds 1 to 24 were synthesized using solid-phase synthesis starting from Sieber amide resin (160 mg, loading 0.62 mmol/g). The synthesis were conducted with microwave irradiation using the Liberty Blue™ microwave peptide synthesizer from CEM S.A.S. A-Fmoc-α amino acid (5 equiv) were coupled with PyBOP (5 equiv) and DIEA (10 equiv) as coupling reagent using the standard Liberty Blue™ methods. The N-Fmoc protecting group was removed with 20% piperidine in DMF (3 mL) also with the standard methods. Each activated monomer (3 equiv) was coupled twice using DIEA (10 equiv) under microwave irradiation (70° C. 50 W, 20 min) in DMF (4 mL). The reduction of the azido group was performed twice in a mixture of 1,4-dioxane/$H_2O$ (7:3 v/v) (5 mL) with a 1 M $PMe_3$ solution in THF (10 equiv) under microwave irradiation (50° C. 50 W, 30 min). See supplementary data for the remaining steps of the synthesis of 24. After completion of the synthesis, the resin was transferred into a syringe with a frit, and washed three times with DMF, three times with $CH_2Cl_2$ and three times with $Et_2O$. Cleavage from the resin was performed using 95% TFA with 2.5% triisopropylsilane and 2.5% water (3 mL). After 2 h the resin was filtered and discarded. Diethyl ether was added to precipitate the oligomer and the solid was triturated and filtrated. Semi preparative purification of all compound was performed by HPLC using a C18ec column (10×250 mm, 5 μm).

In vitro pharmacology ($EC_{50}$). Evaluation of the agonist activity of compounds 1-23 at the mouse GLP-1 receptor endogenously expressed in βTC6 cells, was determined by measuring their effects on cAMP production using the HTRF detection method (performed by Cerep S.A.). The cells were suspended in HBSS buffer (Invitrogen) complemented with 20 mM HEPES (pH 7.4) and 500 μM IBMX, then distributed in microplates at a density of 1.5×10^4 cells/well and incubated for 10 min at room temperature in the presence of HBSS (basal control), the test compound or the reference agonist. Following incubation, the cells were lysed and the fluorescence acceptor (D2-labeled cAMP) and fluorescence donor (anti-cAMP antibody labeled with europium cryptate) were added. After 60 min at room temperature, the fluorescence transfer was measured at $\lambda_{ex}$=337 nm and $\lambda_{em}$=620 nm and 665 nm using a microplate reader (Rubystar, BMG). The cAMP concentration was determined by dividing the signal measured at 665 nm by that measured at 620 nm (ratio). The results are expressed as a percent of the control response to 10 nM GLP-1. The standard reference agonist is GLP-1, which is tested in each experiment at several concentrations to generate a concentration-response curve from which its $EC_{50}$ value and SE is calculated using GraphPad Prism.

Enzymatic degradation (NEP 24.11). Stock solutions of the oligomers were prepared at a concentration of 400 µM in a solution of 50 mM HEPES buffer, 50 mM NaCl, 0.05% Tween-80, pH 8.0. Stock solution of NEP 24.11 was prepared at a concentration of 100 µg/mL in water. Stability of oligomers to NEP 24.11 was assessed by conducting protease reaction in a 96-well plates at 20° C. To each well was added 2 µL of HEPES buffer, 38 µL of the solution of oligomer to be assayed (final concentration 304 µmol/L) and 10 µL of the solution of enzyme (final concentration 20 µg/mL) for a total volume of 50 µL. Each compound was also incubated in the absence of the enzyme (12 µL of HEPES buffer and 38 µL of oligomer). At the indicated time (1, 2, 4, 6 and 22 hours) an aliquot of 10 µL was removed from each experimental reaction and pipetting into 100 µL of 1% TFA solution to quench the reaction, (t=0 min was determined using the reaction without enzyme). A portion of the quenched reaction solution was analyzed by HPLC. The time course of peptide degradation was determined by integrating the area of each peak in a series of HPLC traces.

Enzymatic degradation (Pancreatin). Stock solutions of the oligomers were prepared at a concentration of 250 µM in DMSO. Stock solution of pancreatin was prepared at a concentration of 10 mg/mL in water. 2 µL of pancreatin stock solution was diluted 1/500 with a solution of TRIS 10 mM pH 7.5 to afford a final concentration of 0.02 mg/mL. The oligomer was then diluted 1/24 with a solution of TRIS 10 mM pH 7.5 to afford a final concentration of 10 µM and incubated at 37° C. (8.3 µL of the oligomer stock solution was diluted with 190 µL of TRIS 10 mM pH 7.5 and 1.7 µL of the pancreatin solution) Each compound was also incubated in the absence of pancreatin (8.3 µL of the oligomer stock solution was diluted with 190 µL of TRIS 10 mM pH 7.5). At the indicated time (20 min and 60 min) an aliquot of 70 µL was removed from each experimental reaction and pipetting into 175 µL of acetonitrile at 0° C. to quench the reaction, (t=0 min was determined using the reaction without pancreatin). The samples were frozen before analysis. The frozen sample were defrost, stirred with a vortex 5 min and finally centrifuged 5 min at 16° C. The supernatant was analyzed by LC-MS. The time course of oligomer degradation was determined by integrating the area of the peak in the extracted ion chromatogram.

Mouse plasma stability. Stock solutions of the oligomers were prepared at a concentration of 250 µM in water. The oligomer was then diluted 1/50 with a solution of plasma/PBS pH 7.4 (1:1) to afford a final concentration of 5 µM and incubated at 37° C. (4 µL of the stock solution was diluted with 196 µL of plasma/PBS, pH 7.4, 1:1) Each compound was also incubated in the absence of plasma (196 µL of $H_2O$/PBS, pH 7.4, 1:1)). At the indicated time (20 min and 60 min) an aliquot of 70 µL was removed from each experimental reaction and pipetting into 175 µL of acetonitrile at 0° C. to quench the reaction, (t=0 min was determined using the reaction without plasma). The samples were frozen before analysis. The frozen sample were defrost, stirred with a vortex 5 min and finally centrifuged 5 min at 16° C. The supernatant was analyzed by LC-MS. The time course of oligomer degradation was determined by integrating the area of the peak in the extracted ion chromatogram.

In Vivo Studies in Mice

Animals. Mice were housed in ventilated and enriched housing cages (310×125×127 mm³) throughout the experimental phase (PD studies: performed by Physiogenex S.A.S; PK study: performed by TechMed$^{ILL}$ (CNRS)). The mice were housed in groups of 3 animals during the study, on a normal 12 hours light cycle (at 8:00 pm lights off), 22±2° C. and 50±10% relative humidity. A standard chow diet (RM1 (E) 801492, SDS) and tap water were provided ad libitum. All procedures were performed in accordance with the *Guide for the Care and Use of Laboratory Animals* (*revised 1996 and 2011, 2010/63/EU*) *and French laws*.

Blood glucose experiment in healthy mice. After the acclimation period (at least 5 days), mice (male C57BL/6J mice (Charles River laboratories) (8 weeks old, 20-25 g)) were randomized into 10 groups (n=3/group) according to their body weight. They were acutely treated via i.v. route at 10 AM (5 µg/mouse). Blood glucose was measured before dosing and at 30 min, 1, 2, 4, 6 h after dosing in fed conditions.

IPGTT experiments in mice. After the acclimation period (at least 5 days), mice (male C57BL/6J mice (Charles River laboratories) (6 weeks old, 20-24 g)) were randomized into 6 groups (n=6/group) according to their body weight. The mice were fasted for 6 h prior being acutely treated via i.v. route (5 µg/mouse i.v. (200 µg/kg, 50 nmol/kg)) formulated at 20 µg/mL in PBS 1×. The IPGTTs were performed (glucose 2 g/kg i.p.) 5 min, 30 min, 2 h or 4 h after dosing and blood glucose was measured 30, 60, 90 and 120 min after the glucose challenge.

Blood glucose experiment in db/db mice. After the acclimation period (at least 5 days), mice (male db/db mice (Charles River laboratories) (7 weeks old, 40 g)) were fasted for 6 hours, then blood was collected to measure levels of glucose and insulin. Mice were then randomized in 5 homogenous groups (n=5/group) according to their 1) BG, 2) HOMA-IR and 3) BW. Then, mice were refed until the day of treatment (at least 2 weeks). At the treatment day, mice received a single intra-peritoneal injection of test items (200 µg/kg, 50 nmol/kg) formulated at 20 µg/mL in PBS 1× or vehicle. Blood was collected from the tail vein and blood glucose levels was measured before the injection and 4, 8, 10, 24, 48 h after dosing in fed conditions.

Pharmacokinetics. Fifteen mice (C57B16) were treated with GLP-1 analogues via i.v. injections (1 mg/kg) formulated at 2 mg/mL in PBS 1×. After 15 min, 1 h, 2 h and 4 h, mice were sacrificed and blood sample were collected. The plasma was separated by centrifugation and the samples were frozen at −80° C. before analysis. A volume of 400 µL of each sample of plasma was mixed with 1 ml of acetonitrile to precipitate the protein and extract the compound. The sample were then vortexed and centrifuged (15 000 g-force, 5 min, 16° C.) to sediment the precipitated protein. The supernatant was analysed by LC-MS/MS using a UHPLC coupled to LC-MS 8030 Shimadzu triple quadrupole.

Statistical analysis. Statistical analyses (two-way anova, Bonferroni post-test and one way anova with Dunnett's multiple comparison test) were applied when indicated. P values lower than 0.05 were considered significant.

Azido building block for oligourea part synthesis on solid support.

The building blocks containing Ala-, Glu- Tyr- and Ile-type side chains were synthesized as previously reported.[1,2]

[1] G. W. Collie, K. Pulka-Ziach, C. M. Lombardo, J. Fremaux, F. Rosu, M. Decossas, L. Mauran, O. Lambert, V. Gabelica, C. D. Mackereth and G. Guichard, *Nat. Chem.*, 2015, 7, 871-878.

[2] C. Douat-Casassus, K. Pulka, P. Claudon and G. Guichard, *Org. Lett.*, 2012, 14, 3130-3133.

Monomer M1; 2,5-dioxopyrrolidin-1-yl (R)-(1-azido-3-phenylpropan-2-yl)carbamate; ($N_3$—$F^{u\alpha}$)

Synthesis of monomer M1

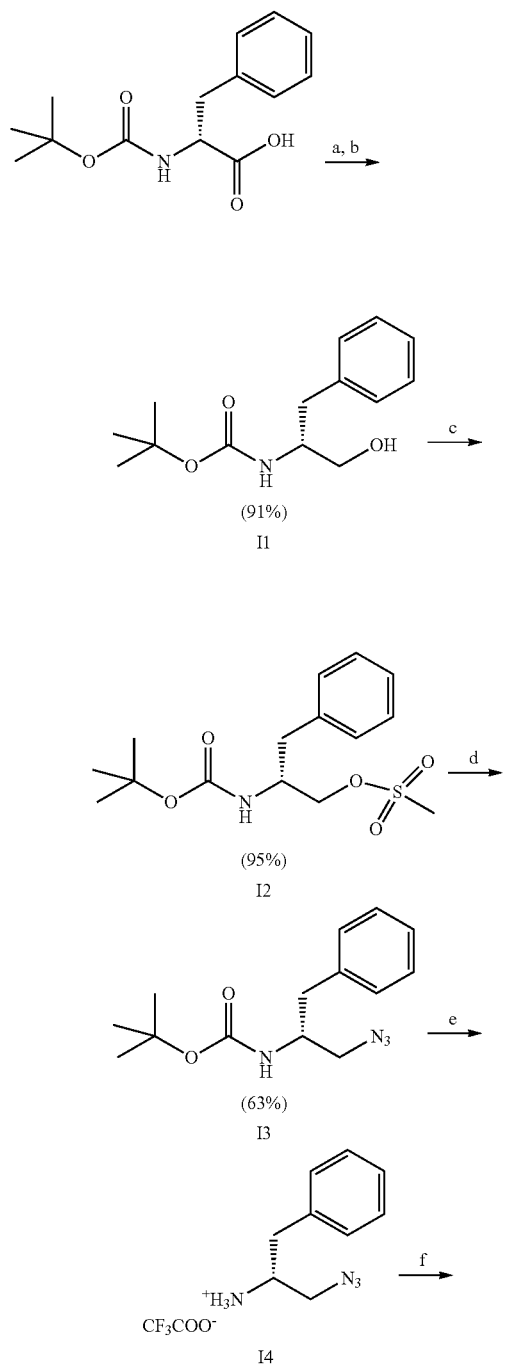

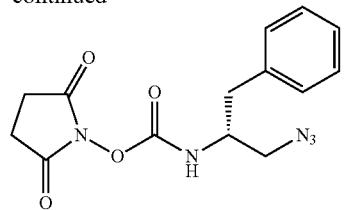

(2 steps 92%)
M1 a: iBuOCOCl, NMM, THF, -10° C.; b: NaBH₄, THF, H₂O, 0° C.; c: MeSO₂Cl, Et₃N, DCM, 0°C.; d: NaN₃, DMF, 80° C.; e: TFA; f: DIEA, DSC, DCM, 0° C.

a: Boc-D-Phe-OH (6.00 g, 22.6 mmol) was dissolved in THF (100 mF) under N₂ at −10° C. 4-Methymorpholine (2.74 mF, 24.9 mmol) was added. Isobutyl chloroformate (2.93 mF, 22.6 mmol) dissolved in THF (10 mF) was added dropwise and the mixture was stirred 45 min at −10° C. The insoluble were filtered.

b: Sodium borohydride (1.71 g, 45.2 mmol) was dissolved in H₂O (4 mF) and the previous filtrate was added dropwise at 0° C. The mixture was stirred overnight at room temperature. THF was evaporated. The compound was dissolved in EtOAc, washed with KHSO₄ (1M), NaHCO₃ (sat) and brine (sat), dried with MgSO₄ and concentrated.

c: I1 (5.16 g, 20.5 mmol) was dissolved in dry DCM (150 mF) under N₂ at 0° C. Triethylamine (2.08 g, 20.5 mmol) was added. Methanesulfonyl chloride (2.35 g, 20.5 mmol) was added dropwise at 0° C. and the mixture was stirred 2 h at 0° C. Organic phase was washed with KHSO₄ (1M), NaHCO₃ (sat) and brine (sat), dried with MgSO₄ and concentrated.

d: I2 (6.44 g, 19.6 mmol) was dissolved in DMF (60.0 mL) and sodium azide (5.08 g, 78.2 mmol) was added with 10 mL of DMF. The mixture was stirred overnight at 80° C. The mixture was cooled down to room temperature. 50 mL of H₂O and 100 mL of EtOAc were added. The aqueous phase was extracted twice with EtOAc. The organic phases were combined, washed with brine (sat), dried with MgSO₄ and concentrated. The compound was purified by flash column chromatography on silica gel. Eluent Cyclohexane/EtOAc 100:0 to 85:15.

e: I3 (3.40 g, 12.3 mmol) was dissolved in trifluoroacetic acid (30 mL) at 0° C. and stirred 45 min. The TFA was evaporated and co-evaporated with cyclohexane.

f: The TFA salt (14) was dissolved in anhydrous DCM (100 mL) under N₂ and cooled to 0° C. N,N-Diisopropylethylamine (2.15 mL, 12.3 mmol) and N,N'-Disuccinimidyl carbonate (3.16 g, 12.3 mmol) were added and the mixture was stirred 3 h at room temperature under N₂. The organic phase was washed with KHSO₄ (1M), and brine (sat), dried with MgSO₄ and concentrated. The compound was triturated in hexane to afford the monomer M1 as a white powder (3.60 g) with a total yield of 50%.

Melting point (M.p.) 112-114° C.; ¹H NMR (CDCl₃, 300 MHz) δ: 7.40-7.20 (m, 5H), 5.86 (d, J=8.1 Hz, 1H), 4.00 (m, 1H), 3.57-3.38 (ddd, J=4.4, 4.6, 12.5 Hz, 2H), 3.06-2.86 (ddd, J=6.0, 8.4, 13.7 Hz, 2H), 2.84 (s, 1H); ¹³C NMR (75 MHz, CDCl₃) δ: 169.86, 150.92, 136.21, 129.32, 128.92, 127.13, 53.09, 52.27, 37.62, 25.48; HRMS (m/z) calcd for $C_{14}H_{15}N_5O_4Na^+[M+Na]^+$ 340.1016, found 340.1004.

Monomer M2; tert-butyl (R)-4-azido-3-((((2,5-dioxopyrrolidin-1-yl)oxy)carbonyl)amino)butanoate; ($N_3$-$D^{u\alpha}$)

Synthesis of monomer M2

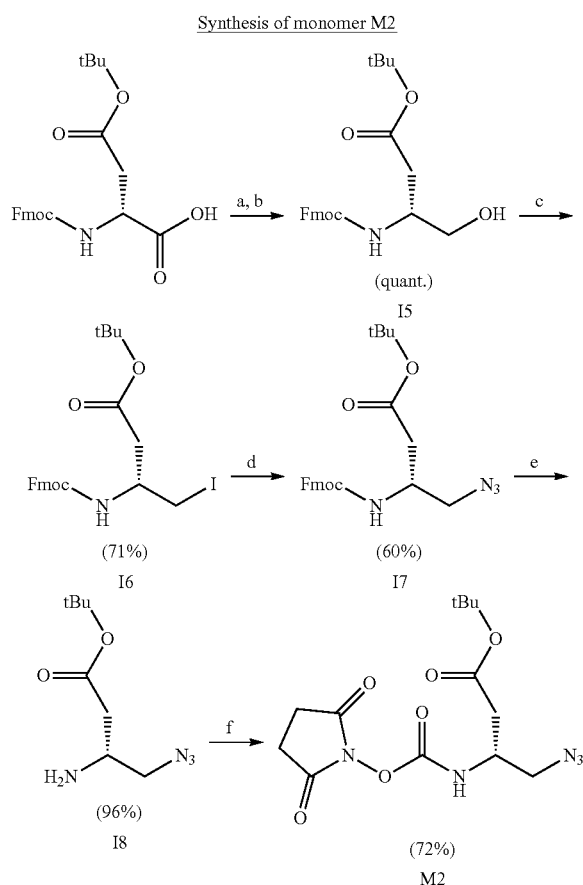

a: iBuOCOCl, NMM, THF, -10° C.; b: NaBH₄, THF, H₂O, 0° C.; c: PPh₃, Imidazole, I₂, DCM; d: NaN₃, DMF; e: Piperidine, THF; f: DSC, EtOAc, 0° C.

a: Fmoc-D-Asp(OtBu)—OH (5.00 g, 11.9 mmol) was dissolved in dry THF (in 500 mF double neck flask) at (-10° C., ice+salt bath) under $N_2$. 4-Methymorpholine (1.45 mF, 13.1 mmol) was added Isobutyl chloroformate (1.62 mF, 12.5 mmol) was added dropwise via an addition funnel. The mixture was stirred 45 min at -10° C. The white precipitate was filtered and washed with THF.

b: Sodium borohydride (901 mg, 23.8 mmol) was dissolved in 5 ml of $H_2O$ and the previous filtrate was added dropwise at 0° C. The mixture was stirred 3 h at RT. THF was evaporated. The compound was solubilized in EtOAc and washed with $KHSO_4$ (1M), $NaHCO_3$ (sat) and brine (sat), dried with $MgSO_4$ and concentrated.

c: Triphenylphosphine (9.56 g, 36.5 mmol) and Imidazole (4.14 g, 60.8 mmol) were dissolved in anhydrous DCM under $N_2$. Iodine (9.25 g, 36.5 mmol) was added. I5 (4.83 g, 12.2 mmol) previously dissolved in anhydrous DCM was added dropwise under $N_2$ and the mixture was stirred 3 h at RT. The solvent was evaporated and the compound was purified by flash column chromatography on silica gel. Eluent Cyclohexane/EtOAc 90:10.

d: I6 (4.40 g, 8.67 mmol) was dissolved in DMF and sodium azide (2.82 g, 43.4 mmol) was added. The mixture was stirred overnight at room temperature. 50 mF of water was added and the compound was extracted with EtOAc three times. Organic phases were combined, dried with $MgSO_4$ and concentrated. The compound was purified by flash column chromatography on silica gel. Eluent Cyclohexane/EtOAc 90:10; 80:20.

e: I7 (2.20 g, 5.21 mmol) was dissolved in THF and Piperidine (10.3 mL, 104 mmol) was added. The mixture was stirred over night at RT. The THF was evaporated and the compound was purified by flash column chromatography on silica gel. Eluent Cyclohexane/EtOAc 70:30; 50:50; 30:70; 0:100 and then EtOAc/MeOH 80:20.

f: N,N'-Disuccinimidyl carbonate (1.45 g, 5.55 mmol) was dissolved in EtOAc (20 mL) at 0° C. I8 (1.00 g, 4.99 mmol) previously dissolved in EtOAc (100 mL) was added dropwise at 0° C. and the mixture was stirred 2 h at room temperature. The solvent was half evaporated. The organic phase was washed with $KHSO_4$ (1M), and brine (sat), dried with $MgSO_4$ and concentrated. The mixture was triturated in hexane to afford the monomer M2 as a white powder (1.37 g) with a total yield of 33%.

Melting point (M.p.) 92-94° C.; $^1H$ NMR (CDCl₃, 300 MHz) δ: 6.34 (d, J=8.46 Hz, 1H), 4.17-4.06 (m, 1H), 3.65-3.50 (m, 2H) 2.85 (s, 4H), 2.63 (d, J=5.72 Hz, 2H), 1.49 (s, 9H); $^{13}C$ NMR (75 MHz, CDCl₃) δ: 169.95, 169.76, 150.91, 82.22, 53.18, 48.87, 36.64, 28.01, 25.48; HRMS (m/z) calcd for $C_{13}H_{19}N_5O_6Na^+[M+Na]^+$ 364.1228, found 364.1213.

General Procedure A for the Synthesis of Oligomers 2-24

Oligomers 2-24 were synthesized using the following general procedure. Sieber resin (≈ 160 mg, loading 0.62 mmol/g) was swelled in DMF (3 mL) for 30 min. All steps were performed under microwave irradiation. The synthesis were conducted with microwave irradiation using the Liberty Blue™ microwave peptide synthesizer from CEM.

A1: Fmoc deprotection. The V-Fmoc protecting group was removed with 20% piperidine in DMF (3 mL) with the standard liberty blue methods.[3]

[3] J. M. Collins, K. A. Porter, S. K. Singh, G. S. Vanier, Org. Lett. 2014, 16, 940-943

A2: Coupling of Fmoc-amino acid. N-Fmoc-α amino acid (5 equiv relative to the resin loading) were coupled with PyBOP (5 equiv relative to the resin loading) and DIE A (10 equiv relative to the resin loading) as coupling reagent using the standard liberty blue methods.[3]

A3: Coupling of activated $N_3$-building bloc. Each activated monomer (3 equiv relative to the resin loading) was coupled twice using DIEA (10 equiv relative to the resin loading) under microwave irradiation (70° C., 50 W, 20 min) in DMF (4 mL).

A4: Reduction of azide group. The reduction of the azido group was performed twice in a mixture of 1,4-dioxane/$H_2O$ (7:3 v/v) (5 mL) with a 1M $PMe_3$ solution in THF (10 equiv relative to the resin loading) under microwave irradiation (50° C., 50 W, 30 min).

A5: Cleavage from the resin. After completion of the synthesis, the resin was transferred into a syringe with a frit, and washed three times with DMF, three times with $CH_2Cl_2$ and three times with $Et_2O$. Cleavage from the resin was performed using 95% TFA with 2.5% triisopropylsilane and 2.5% water (3 mL). After 2 h the resin was filtered and discarded. Diethyl ether was added to precipitate the oligomer and the solid was triturated and filtrated.

A6: Purification and characterization. Analytical RP-HPLC analyses were performed on a Dionex U3000SD using a Macherey-Nagel Nucleodur C18ec column (4×100 mm, 3 μm) at a flow rate of 1 mL/min with UV detection at 200 nm. The mobile phase was composed of 0.1% (v/v) TFA-$H_2O$ (Solvent A) and 0.1% (v/v) TFA-$CH_3CN$ (solvent B).

Semi preparative purification of all compounds was performed on a Dionex U3000SD using a Macherey-Nagel Nucleodur C18ec column (10×250 mm, 5 μm) at a flow rate of 4 mL/min with UV detection at 200 nm. The mobile phase was composed of 0.1% (v/v) TFA-H$_2$O (Solvent A) and 0.1% (v/v) TFA-CH$_3$CN (solvent B).

LC-MS analyses were carried out on a UHPLC (Agilent 1290 Infinity) coupled to a ESI-MS Tof (Agilent 6230 ESI).

Electrospray ionization mass spectrometry (ESI-MS) experiments were performed on an Agilent 6560 DTIMS-Q-TOF spectrometer (Agilent Technologies, Santa Clara, Calif.), with the dual-ESI source operated in positive ion mode.

Procedure B for the Synthesis of Oligomer 25

A-Fmoc-Lys(Boc)—OH at position 20 was replaced by A-Fmoc-Lys(Alloc)-OH and A-Fmoc-His(Trt)-OH at position 1 was replaced by A-Boc-His(Boc)-OH.

B1: Synthesis

The oligomer was synthesized using procedure A. Then the resin was transferred in a 10 mL syringe, 5 mL of DCM was added and the Alloc group was removed using Pd(Ph$_3$)$_4$ (30 mg, 0.25 equiv relative to the resin loading) and phenylsilane (135 µL, 1.1 equiv relative to the resin loading) at room temperature for 45 min. After filtration and washes (3×DCM), DCM (5 mL), Fmoc-OcO$_2$—OH (193 mg, 5 equiv), PyBop (260 mg, 5 equiv relative to the resin loading) and DIEA (93 µL, 5 equiv relative to the resin loading) were loaded on the resin and it was shaken for 2 hours at room temperature. After filtration and washes (3×DCM, 3×DMF) Fmoc group was removed with piperidine in DMF (20%), 2 times 20 min. The resin was washed with DMF (2×) and DCM (3×), then DCM (5 mF), Fmoc-OcO$_2$—OH (193 mg, 5 equiv relative to the resin loading), PyBop (260 mg, 5 equiv relative to the resin loading) and DIEA (93 µF, 5 equiv relative to the resin loading) were loaded on the resin and it was shaken for 2 hours at room temperature and again Fmoc group was removed with piperidine (20%) twice. The resin was washed with DMF (2×) and DCM (3×), then DCM (5 mF), N-Fmoc-Glu(OH)—OtBu (222 mg, 5 equiv relative to the resin loading), PyBop (260 mg, 5 equiv relative to the resin loading), and DIEA (93 µF, 5 equiv relative to the resin loading) were loaded on the resin and it was shaken for 2 hours at room temperature. Fmoc group was removed with piperidine in DMF (20%), 2 times 20 min. The resin was washed with DMF (2×) and DCM (3×), then the 18-(terbutoxy)18-oxooctadecanoic acid (111 mg, 3 equiv relative to the resin loading), ByBop (156 mg, 3 equiv relative to the resin loading) and DIEA (52 µF, 3 equiv relative to the resin loading) were loaded on the resin and it was shaken for 2 hours at room temperature.

B2: Cleavage

Same as A5

B3: Purification and Characterization

Same as A6

Procedure C for the Synthesis of Semaglutide (25)

N-Fmoc-Lys(Boc)-OH at position 20 was replaced by N-Fmoc-Fys(Alloc)-OH and N-Fmoc-His(Trt)-OH at position 1 was replaced by N-Boc-His(Boc)-OH.

C1: Attachment to Benzyl Alcohol Resin

N-Fmoc-Gly-OH was coupled on the resin with mixt anhydride (novabiochem procedure[4]). N-Fmoc-Gly-OH (300 mg, 5 equiv relative to the resin loading) was dissolved in dry DCM (3 mF) under inert atmosphere. N,N'-Dicyclohexylcarbodiimide (103 mg, 2.5 equiv relative to the resin loading) was added and the mixture was stirred 20 min at 0° C. then DCM was concentrated and DMF was added. The mixture was loaded on the swollen Wang resin (loading 0.51 mmol/g) with a catalytic amount of 4-Dimethylaminopyridine (DMAP). The resin was shaked for 2 hours at room temperature.

[4] Novabiochem® 2014/2015, 3.6 (Method 3-8)

C2: Synthesis

The oligomer was synthesized using procedure B1.

C3: Cleavage

Same as A5

C4: Purification and Characterization

Same as A6

Characterization of oligomers 1-25 (analysis, resistance to NEP 24.11 degradation and GLP-1R agonist activity)

(SEQ ID NO. 1)
H-HGEGTFTSDVSSYLEGQAAKEFIAWLVKGRG-NH$_2$

Peptide 1 was synthesized using the general procedure A starting from sieber resin (160 mg, 0.1 mmol). The final product 1 was purified by semi-preparative HPLC. 6.1 mg was obtained (yield 1.8%). HPLC: R$_t$=5.29 min (10-100%; CH$_3$CN 0.1% TFA in H$_2$O 0.1% TFA, 10 min, C18); LC-MS (m/z 3340.71): 668.78 [M+5H]$^{5+}$, 835.75 [M+4H]$^{4+}$, 1114.36 [M+3H]$^{3+}$ 1671.10 [M+2H]$^{2+}$.

FIG. 7A demonstrates the concentration-response curve (receptor-mediated cAMP produced) for EC50 determination of peptide 1 in cells expressing the GFP-1R. FIG. 7B demonstrates the enzymatic degradation of peptide 2 by NEP 24.11. FIG. 7C demonstrates the mouse plasma degradation results for peptide 2.

(SEQ ID NO. 2)
H-HGEGTFTSD"ᵘ"ᵃ"ᵃ"YLEGQAAKEFIAWLVKGRG-NH$_2$

Peptide-oligourea hybrid 2 was synthesized using the general procedure A starting from sieber resin (160 mg, 0.1 mmol). The final product 2 was purified by semi-preparative HPLC. 10.13 mg was obtained (yield 3.1%). HPLC: R$_t$=5.28 min (10-100% CH$_3$CN 0.1% TFA in H$_2$O 0.1% TFA, 10 min, C18); LC-MS (m/z 3296.70): 660.15 [M+5H]$^{5+}$, 825.19[M+4H]$^{4+}$, 1099.58 [M+3H]$^{3+}$, 1649.37 [M+2H]$^{2+}$.

FIG. 8A demonstrates the concentration-response curve (receptor-mediated cAMP produced) for EC50 determination of peptide-oligourea hybrid 2 in cells expressing the GLP-1R. FIG. 8B demonstrates the enzymatic degradation of peptide 2 by NEP 24.11. FIG. 8C demonstrates the mouse plasma degradation results for peptide-oligourea 3.

(SEQ ID NO. 3)
H-HGEGTFTSDA"ᵃ"ᵃ"LEGQAAKEFIAWLVKGRG-NH$_2$

Peptide-oligourea hybrid 4 was synthesized using the general procedure A starting from sieber resin (160 mg, 0.1 mmol). The final product 3 was purified by semi-preparative HPLC. 28.4 mg was obtained (yield 8.9%). HPLC: R$_t$=5.25 min (10-100% CH$_3$CN 0.1% TFA in H$_2$O 0.1% TFA, 10 min, C18); ESI+ (m/z 3204.61): 641.67 [M+5H]$^{5+}$, 802.13 [M+4H]$^{4+}$, 1069.27 [M+3H]$^{3+}$, 1603.27 [M+2H]$^{2+}$.

Figure 9:
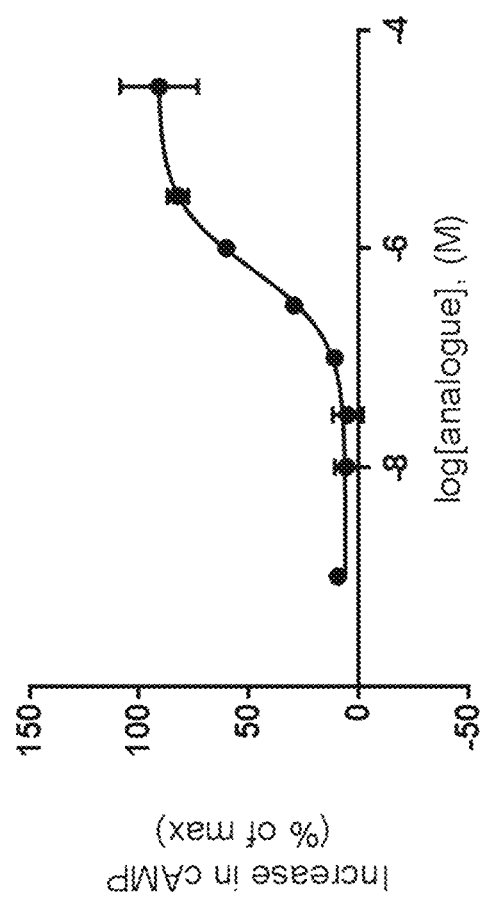
FIG. 9. Demonstrates the concentration-response curve (receptor-mediated cAMP produced) for EC50 determination of peptide-oligourea SEQ ID NO: 3 in cells expressing the GLP-1R.

FIG. 9 demonstrates the concentration-response curve (receptor-mediated cAMP produced) for EC50 determination of peptide-oligourea 3 in cells expressing the GFP-1R.

(SEQ ID NO. 4)
H-HGEGTFTSDVA"ᵃ"ᵃ"EGQAAKEFIAWLVKGRG-NH$_2$

Peptide-oligourea hybrid 4 was synthesized using the general procedure A starting from sieber resin (160 mg, 0.1 mmol). The final product 4 was purified by semi-preparative HPLC. 7.0 mg was obtained (yield 2.2%). HPLC: R$_t$=5.01 min (10-100% CH$_3$CN 0.1% TFA in H$_2$O 0.1% TFA, 10 min, C18); ESI+ (m/z 3190.58): 639.13 [M+5H]$^{5+}$, 798.60 [M+4H]$^{4+}$, 1064.47 [M+3H]$^{3+}$, 1595.87 [M+2H]$^{2+}$.

Figure 10:
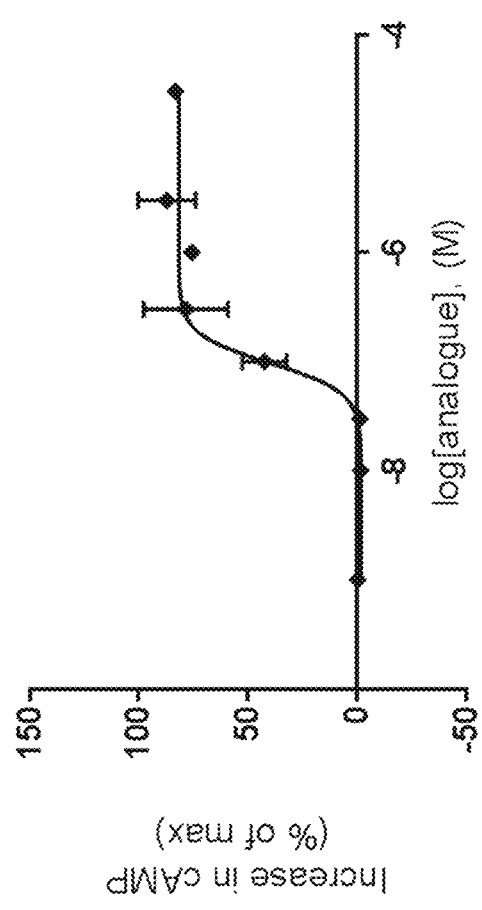
FIG. 10. Demonstrates the concentration-response curve (receptor-mediated cAMP produced) for EC50 determination of peptide-oligourea SEQ ID NO: 4 in cells expressing the GLP-1R.

FIG. 10 demonstrates the concentration-response curve (receptor-mediated cAMP produced) for EC50 determination of peptide-oligourea 4 in cells expressing the GFP-1R.

(SEQ ID NO. 5)
H-HGEGTFTSDVA"Y"A"EGQAAKEFIAWLVKGRG-NH$_2$

Peptide-oligourea hybrid 5 was synthesized using the general procedure A starting from Sieber resin (160 mg, 0.1 mmol). The final product 5 was purified by semi-preparative HPLC. 2.4 mg was obtained (yield 0.8%). HPLC: R$_t$=5.08 min (10-100% CH$_3$CN 0.1% TFA in H$_2$O 0.1% TFA, 10 min, C18); FC-MS (m/z 3282.67): 657.36[M+5H]$^{5+}$, 821.45 [M+4H]$^{4+}$, 1094.93 [M+3H]$^{3+}$, 1641.89 [M+2H]$^{2+}$.

Figure 11A:
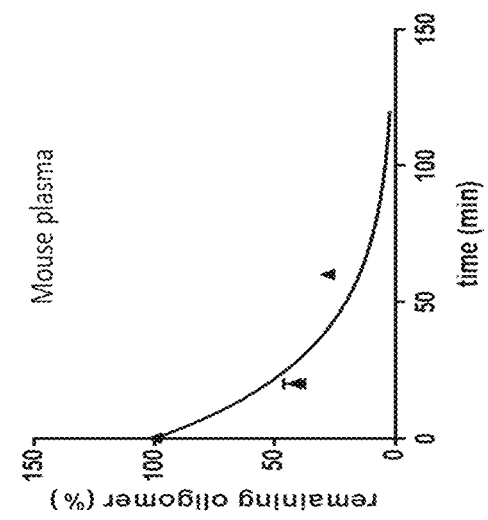
FIGS. 11A, 11B, and 11C. (11A) demonstrates the concentration-response curve (receptor-mediated cAMP produced) for EC50 determination of peptide-oligourea SEQ ID NO: 5 in cells expressing the GLP-1R. (11B) demonstrate the enzymatic degradation of peptide-oligourea SEQ ID NO: 5 by NEP 24.11. (11C) demonstrates the mouse plasma degradation of peptide-oligourea hybrid SEQ ID NO: 5.
Figure 11B:
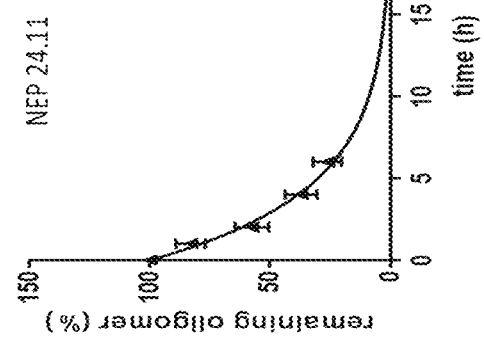
Figure 11C:
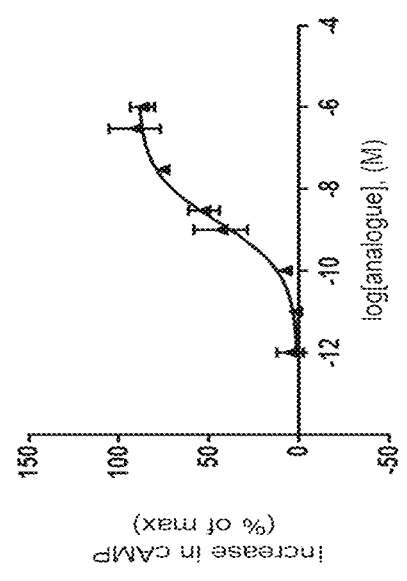

FIG. 11 demonstrates the concentration-response curve (receptor-mediated cAMP produced) for EC50 determination of peptide-oligourea 5 in cells expressing the GFP-1R (FIG. 11A). FIG. 11B demonstrate the enzymatic degradation of peptide-oligourea hybrid 6 by NEP 24.11. FIG. 11C demonstrates the mouse plasma degradation of peptide-oligourea hybrid 5.

(SEQ ID NO. 6)
H-HGEGTFTSDVSA"A"A"GQAAKEFIAWLVKGRG-NH$_2$

Peptide-oligourea hybrid 6 was synthesized using the general procedure A starting from sieber resin (160 mg, 0.1 mmol). The final product 6 was purified by semi-preparative HPLC. 9.3 mg was obtained (yield 2.95%). HPLC: R$_t$=5.08 min (10-100% CH$_3$CN 0.1% TFA in H$_2$O 0.1% TFA, 10 min, C18); ESI+ (m/z 3148.54): 630.67 [M+5H]$^{5+}$, 788.00 [M+4H]$^{4+}$, 1050.27 [M+3H]$^{3+}$, 1575.33 [M+2H]$^{2+}$.

Figure 12:
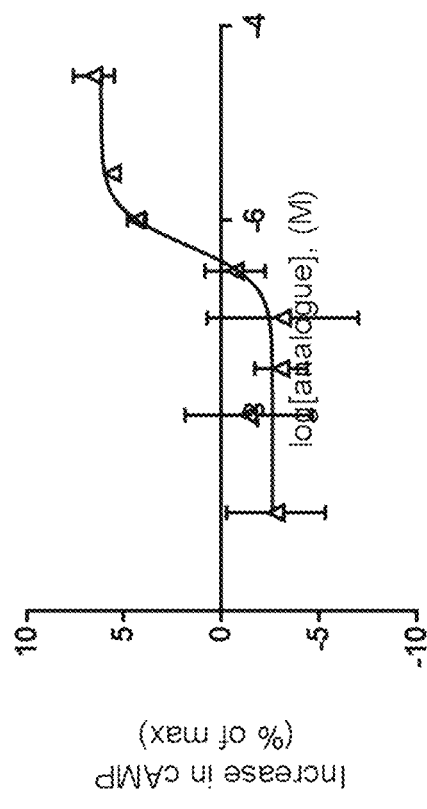
FIG. 12. Demonstrates the concentration-response curve (receptor-mediated cAMP produced) for EC50 determination of peptide-oligourea SEQ ID NO: 6 in cells expressing the GLP-1R.

FIG. 12 demonstrates the concentration-response curve (receptor-mediated cAMP produced) for EC50 determination of peptide-oligourea 6 in cells expressing the GFP-1R.

(SEQ ID NO. 8)
H-HGEGTFTSDVSSA"A"A"QAAKEFIAWLVKGRG-NH$_2$

Peptide-oligourea hybrid 7 was synthesized using the general procedure A starting from sieber resin (160 mg, 0.1 mmol). The final product 7 was purified by semi-preparative HPLC. 11.88 mg was obtained (yield 3.7%). HPLC: R$_t$=5.13 min (10-100% CH$_3$CN 0.1% TFA in H$_2$O 0.1% TFA, 10 min, C18); ESI+ (m/z 3178.57): 795.51 [M+4H]$^{4+}$, 1060.63 [M+3H]$^{3+}$, 1590.80 [M+2H]$^{2+}$.

Figure 13:
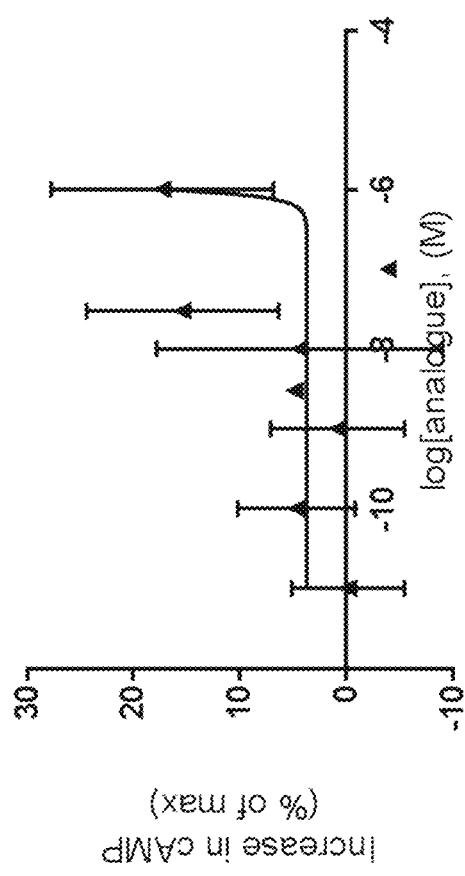
FIG. 13. Demonstrates the concentration-response curve (receptor-mediated cAMP produced) for EC50 determination of peptide-oligourea hybrid SEQ ID NO: 7 in cells expressing the GLP-1R.

FIG. 13 demonstrates the concentration-response curve (receptor-mediated cAMP produced) for EC50 determination of peptide-oligourea 7 in cells expressing the GLP-1R.

(SEQ ID NO. 8)
H-HGEGTFTSDVSSYA"A"A"AAKEFIAWLVKGRG-NH$_2$

Peptide-oligourea hybrid 8 was synthesized using the general procedure A starting from sieber resin (160 mg, 0.1 mmol). The final product 8 was purified by semi-preparative HPLC. 3.22 mg was obtained (yield 1.0%). HPLC: R$_t$=5.20 min (10-100% CH$_3$CN 0.1% TFA in H$_2$O 0.1% TFA, 10 min, C18); ESI+ (m/z 3213.61): 643.60 [M+5H]$^{5+}$, 804.33 [M+4H]$^{4+}$, 1072.07 [M+3H]$^{3+}$, 1607.73[M+2H]$^{2+}$.

Figure 14:
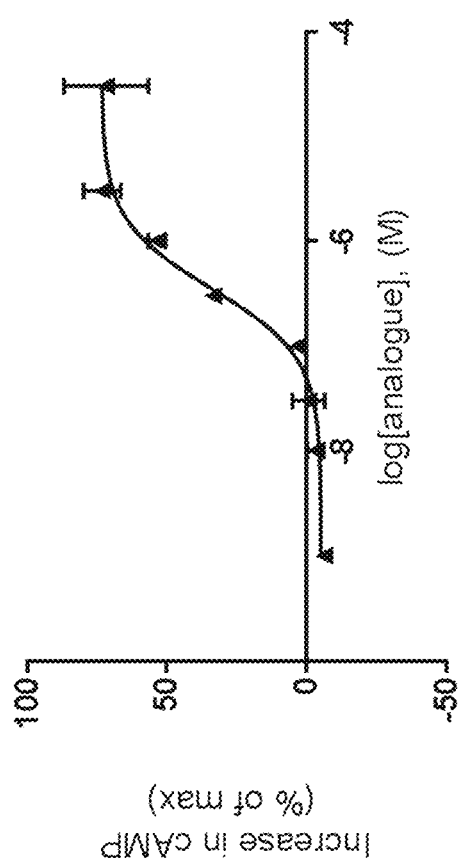
FIG. 14. Demonstrates the concentration-response curve (receptor-mediated cAMP produced) for EC50 determination of peptide-oligourea hybrid SEQ ID NO: 8 in cells expressing the GLP-1R.

FIG. 14 demonstrates the concentration-response curve (receptor-mediated cAMP produced) for EC50 determination of peptide-oligourea hybrid 8 in cells expressing the GFP-1R.

(SEQ ID NO. 9)
H-HGEGTFTSDVSSYY"E"A"AAKEFIAWLVKGRG-NH$_2$

Peptide-oligourea hybrid 9 was synthesized using the general procedure A starting from sieber resin (160 mg, 0.1 mmol). The final product 9 was purified by semi-preparative HPLC. 2.3 mg was obtained (yield 0.7%). HPLC: R$_t$=5.11 min (10-100% CH$_3$CN 0.1% TFA in H$_2$O 0.1% TFA, 10 min, C18); FC-MS (m/z 3363.74): 673.74 [M+5H]$^{5+}$, 841.68 [M+4H]$^{4+}$, 1121.90 [M+3H]$^{3+}$, 1682.85 [M+2H]$^{2+}$.

FIG. 15 demonstrates the concentration-response curve (receptor-mediated cAMP produced) for EC50 determination of peptide-oligourea 9 in cells expressing the GFP-1R (FIG. 15A). FIG. 15B demonstrate the enzymatic degradation of peptide-oligourea hybrid 9 by NEP 24.11. FIG. 15C demonstrates the mouse plasma degradation of peptide-oligourea hybrid 9.

(SEQ ID NO. 10)
H-HGEGTFTSDVSSYLA"A"A"AKEFIAWLVKGRG-NH$_2$

Peptide-oligourea 10 was synthesized using the general procedure A starting from sieber resin (160 mg, 0.1 mmol). The final product 10 was purified by semi-preparative HPLC. 13.02 mg was obtained (yield 4.0%). HPLC: R$_t$=5.31 min (10-100% CH$_3$CN 0.1% TFA in H$_2$O 0.1% TFA, 10 min, C18); ESI+ (m/z 3255.69): 814.80 [M+4H]$^{4+}$, 1086.33 [M+3H]$^{3+}$, 1628.33 [M+2H]$^{2+}$.

FIG. 16 demonstrates the concentration-response curve (receptor-mediated cAMP produced) for EC50 determination of peptide-oligourea hybrid 10 in cells expressing the GLP-1R.

(SEQ ID NO. 11)
H-HGEGTFTSDVSSYLE"A"A"AKEFIAWLVKGRG-NH$_2$

Peptide-oligourea hybrid 11 was synthesized using the general procedure A starting from sieber resin (160 mg, 0.1 mmol). The final product 11 was purified by semi-preparative HPLC. 17.6 mg was obtained (yield 5.3%). HPLC: R$_t$=5.27 min (10-100% CH$_3$CN 0.1% TFA in H$_2$O 0.1% TFA, 10 min, C18); LC-MS (m/z 3313.73): 663.55 [M+5H]$^{5+}$, 829.19 [M+4H]$^{4+}$, 1105.25 [M+3H]$^{3+}$.

FIG. 17 demonstrates the concentration-response curve (receptor-mediated cAMP produced) for EC50 determination of peptide-oligourea hybrid 11 in cells expressing the GLP-1R (FIG. 17A). FIG. 17B demonstrates the enzymatic degradation of peptide-oligourea hybrid 11 by NEP 24.11. FIG. 17C demonstrates the mouse plasma degradation of peptide-oligourea hybrid 11.

(SEQ ID NO. 12)
H-HGEGTFTSDVSSYLEA"A"A"KEFIAWLVKGRG-NH$_2$

Peptide-oligourea hybrid 12 has been synthesized using the general procedure A starting from sieber resin (160 mg, 0.1 mmol). The final product 12 was purified by semi-preparative HPLC. 10.2 mg was obtained (yield 3.1%). HPLC: R$_t$=5.19 min (10-100% CH$_3$CN 0.1% TFA in H$_2$O 0.1% TFA, 10 min, C18); ESI+ (m/z 3313.73): 829.53 [M+4H]$^{4+}$, 1105.40 [M+3H]$^{3+}$, 1657.87 [M+2H]$^{2+}$.

FIG. 18 demonstrates the concentration-response curve (receptor-mediated cAMP produced) for EC50 determination of peptide-oligourea hybrid 12 in cells expressing the GLP-1R.

(SEQ ID NO. 13)
H-HGEGTFTSDVSSYLEGA"A"A"EFIAWLVKGRG-NH$_2$

Peptide-oligourea hybrid 13 has been synthesized using the general procedure A starting from sieber resin (160 mg, 0.1 mmol). The final product 13 was purified by semi-preparative HPLC. 10.98 mg was obtained (yield 3.4%). HPLC: R$_f$=5.45 min (10-100% CH$_3$CN 0.1% TFA in H$_2$O 0.1% TFA, 10 min, C18); ESI+ (m/z 3242.61): 811.53 [M+4H]$^{4+}$, 1081.73 [M+3H]$^{3+}$, 1621.87 [M+2H]$^{2+}$.

Figure 19:
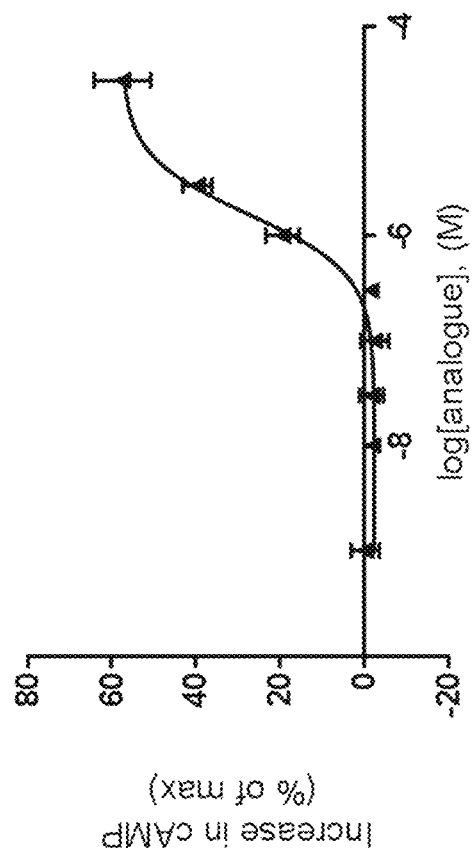
FIG. 19. Demonstrates the concentration-response curve (receptor-mediated cAMP produced) for EC50 determination of peptide-oligourea hybrid SEQ ID NO: 13 in cells expressing the GLP-1R.

FIG. 19 demonstrates the concentration-response curve (receptor-mediated cAMP produced) for EC50 determination of peptide-oligourea hybrid 13 in cells expressing the GLP-1R.

(SEQ ID NO. 14)
H-HGEGTFTSDVSSYLEGQA"A"A"FIAWLVKGRG-NH$_2$

Peptide-oligourea hybrid 14 has been synthesized using the general procedure A starting from sieber resin (160 mg, 0.1 mmol). The final product 14 was purified by semi-preparative HPLC. 6.0 mg was obtained (yield 1.85%). HPLC: R$_f$=5.48 min (10-100% CH$_3$CN 0.1% TFA in H$_2$O 0.1% TFA, 10 min, C18); LC-MS (m/z 3241.62): 649.14 [M+5H]$^{5+}$, 811.17[M+4H]$^{4+}$, 1081.23 [M+3H]$^{3+}$, 1621.33 [M+2H]$^{2+}$.

Figure 20C:
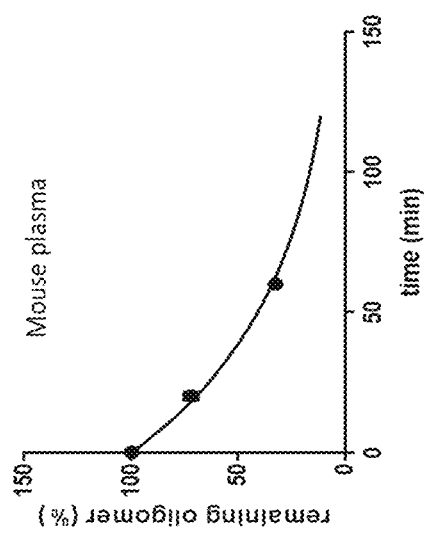
FIGS. 20A, 20B, and 20C. (20A) Demonstrates the concentration-response curve (receptor-mediated cAMP produced) for EC50 determination of peptide-oligourea hybrid SEQ ID NO: 14 in cells expressing the GLP-1R. (20B) demonstrates the enzymatic degradation of peptide-oligourea SEQ ID NO: 14 by NEP 24.11. (20C) demonstrates the mouse plasma degradation of peptide-oligourea hybrid SEQ ID NO: 14.
Figure 20B:
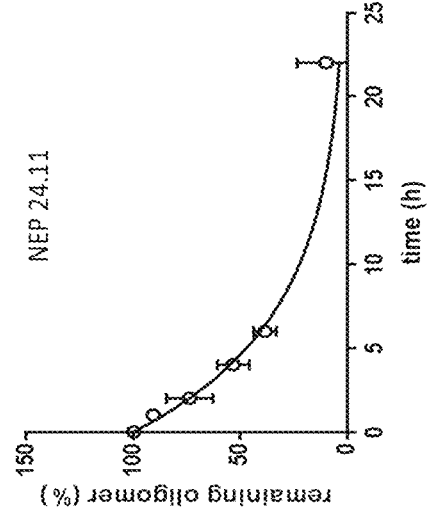
Figure 20A:
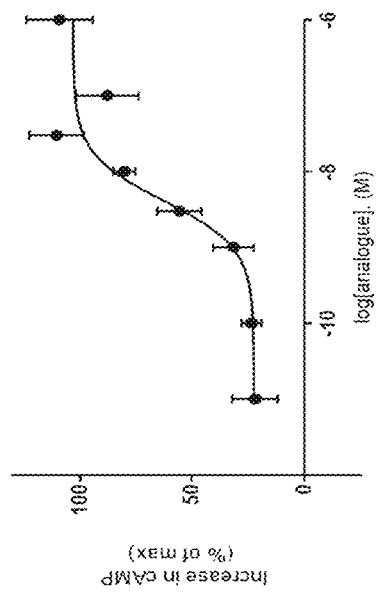

FIG. 20 demonstrates the concentration-response curve (receptor-mediated cAMP produced) for EC50 determination of peptide-oligourea hybrid 14 in cells expressing the GLP-1R (FIG. 20A). FIG. 20B demonstrates the enzymatic degradation of peptide-oligourea 14 by NEP 24.11. FIG. 20C demonstrates the mouse plasma degradation of peptide-oligourea hybrid 14.

(SEQ ID NO. 15)
H-HGEGTFTSDVSSYLEGQAA"A"A"IAWLVKGRG-NH$_2$

Peptide-oligourea hybrid 15 has been synthesized using the general procedure A starting from sieber resin (160 mg, 0.1 mmol). The final product 15 was purified by semi-preparative HPLC. 8.4 mg was obtained (yield 2.6%). HPLC: R$_f$=5.05 min (10-100% CH$_3$CN 0.1% TFA in H$_2$O 0.1% TFA, 10 min, C18); ESI+ (m/z 3165.52): 792.27 [M+4H]$^{4+}$, 1056.00 [M+3H]$^{3+}$, 1583.53 [M+2H]$^{2+}$.

Figure 21:
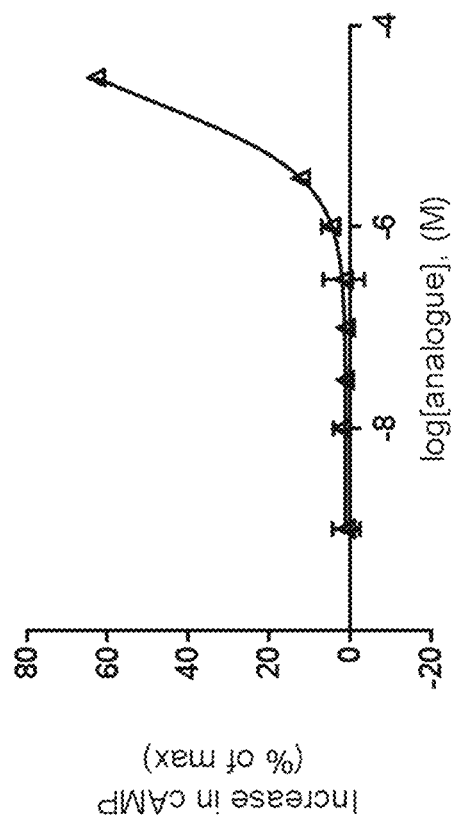
FIG. 21. Demonstrates the concentration-response curve (receptor-mediated cAMP produced) for EC50 determination of peptide-oligourea hybrid SEQ ID NO: 15 in cells expressing the GLP-1R.

FIG. 21 demonstrates the concentration-response curve (receptor-mediated cAMP produced) for EC50 determination of peptide-oligourea hybrid 15 in cells expressing the GLP-1R.

(SEQ ID NO. 16)
H-HGEGTFTSDVSSYLEGQAAKEF"$^\alpha$"I"A"LVKGRG-NH$_2$

Peptide-oligourea hybrid 16 was synthesized using the general procedure A starting from sieber resin (160 mg, 0.1 mmol). The final product 16 was purified by semi-preparative HPLC. 4.8 mg was obtained (yield 1.5%). HPLC: R$_f$=5.07 min (10-100% CH$_3$CN 0.1% TFA in H$_2$O 0.1% TFA, 10 min, C18); ESI+ (m/z 3241.62): 811.60 [M+4H]$^{4+}$, 1081.53 [M+3H]$^{3+}$, 1621.80 [M+2H]$^{2+}$.

Figure 22C:
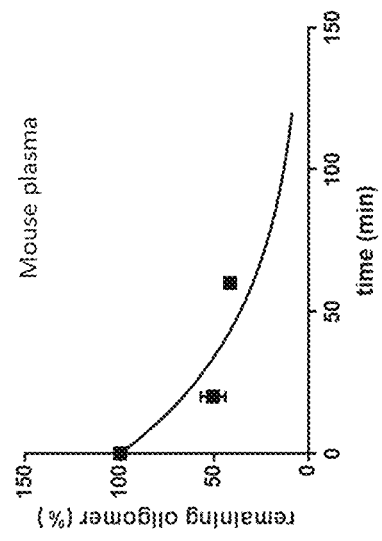
FIGS. 22A, 22B, and 22C. (22A) Demonstrates the concentration-response curve (receptor-mediated cAMP produced) for EC50 determination of peptide-oligourea SEQ ID NO: 16 in cells expressing the GLP-1R. (22B) demonstrates the enzymatic degradation of peptide-oligourea hybrid SEQ ID NO: 16 by NEP 24.11. (22C) demonstrates the mouse plasma degradation of peptide-oligourea SEQ ID NO: 16.
Figure 22B:
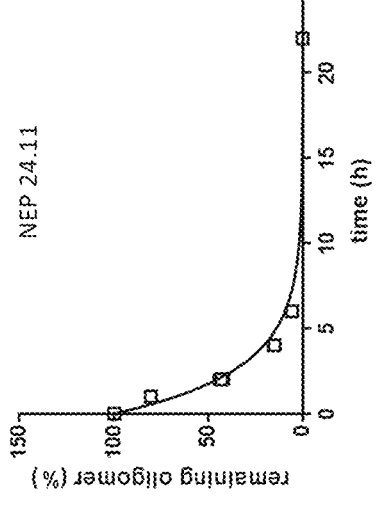
Figure 22A:
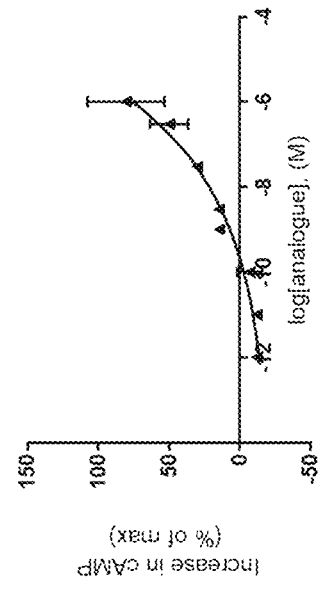

FIG. 22 demonstrates the concentration-response curve (receptor-mediated cAMP produced) for EC50 determination of peptide-oligourea 16 in cells expressing the GFP-1R (FIG. 22A). FIG. 22B demonstrates the enzymatic degradation of peptide-oligourea hybrid 16 by NEP 24.11. FIG. 22C demonstrates the mouse plasma degradation of peptide-oligourea 16.

(SEQ ID NO. 17)
H-HGEGTFTSDVSSYLEGQAAKEFA"A"A"VKGRG-NH$_2$

Peptide-oligourea hybrid 17 was synthesized using the general procedure A starting from sieber resin (160 mg, 0.1 mmol). The final product 17 was purified by semi-preparative HPLC. 10.3 mg was obtained (yield 3.3%). HPLC: R$_f$=4.52 min (10-100% CH$_3$CN 0.1% TFA in H$_2$O 0.1% TFA, 10 min, C18); ESI+ (m/z 3157.46): 632.47 [M+5H]$^{5+}$, 790.20 [M+4H]$^{4+}$, 1053.27 [M+3H]$^{3+}$, 1579.73 [M+2H]$^{2+}$.

Figure 23:
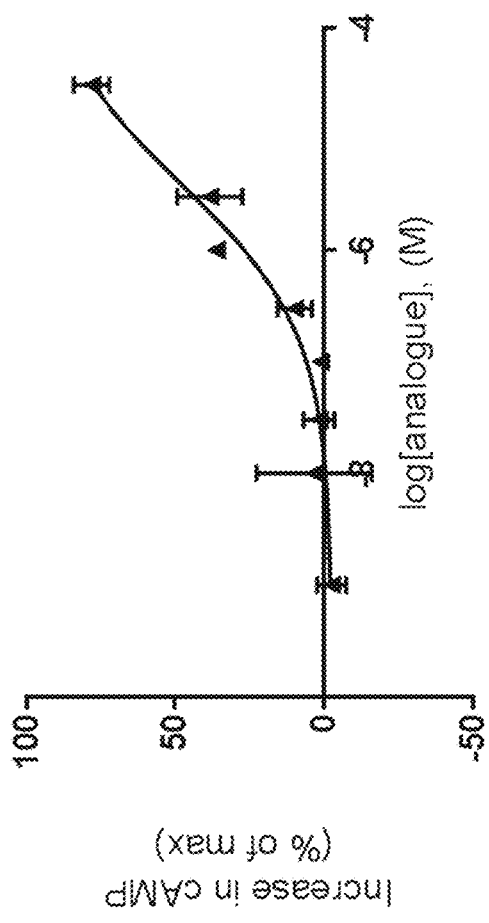
FIG. 23. Demonstrates the concentration-response curve (receptor-mediated cAMP produced) for EC50 determination of peptide-oligourea hybrid SEQ ID NO: 17 in cells expressing the GLP-1R.

FIG. 23 demonstrates the concentration-response curve (receptor-mediated cAMP produced) for EC50 determination of peptide-oligourea hybrid 17 in cells expressing the GLP-1R.

(SEQ ID NO. 18)
H-HGEGTFTSDVSSYLEGQAAKEFIA"A"A"KGRG-NH$_2$

Peptide-oligourea hybrid 18 was synthesized using the general procedure A starting from sieber resin (160 mg, 0.1 mmol). The final product 18 was purified by semi-preparative HPLC. 10.0 mg was obtained (yield 3.2%). HPLC: R$_f$=4.60 min (10-100% CH$_3$CN 0.1% TFA in H$_2$O 0.1% TFA, 10 min, C18); ESI+ (m/z 3171.48): 635.07 [M+5H]$^{5+}$, 794.00 [M+4H]$^{4+}$, 1058.20 [M+3H]$^{3+}$, 1586.73 [M+2H]$^{2+}$.

Figure 24:
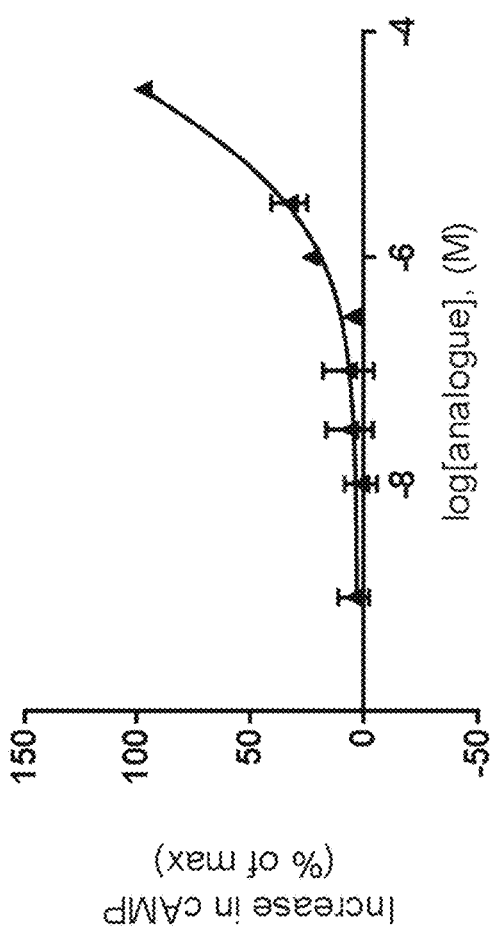
FIG. 24. Demonstrates the concentration-response curve (receptor-mediated cAMP produced) for EC50 determination of peptide-oligourea hybrid SEQ ID NO: 18 in cells expressing the GLP-1R.

FIG. 24 demonstrates the concentration-response curve (receptor-mediated cAMP produced) for EC50 determination of peptide-oligourea hybrid 18 in cells expressing the GLP-1R.

(SEQ ID NO. 19)
H-HGEGTFTSDVSSYLEGQAAKEFIAA"A"A"GRG-NH$_2$

Peptide-oligourea hybrid Oligomer 19 was synthesized using the general procedure A starting from sieber resin (160 mg, 0.1 mmol). The final product 19 was purified by semi-preparative HPLC. 2.3 mg was obtained (yield 0.7%). HPLC: R$_f$=4.68 min (10-100% CH$_3$CN 0.1% TFA in H$_2$O 0.1% TFA, 10 min, C18); FC-MS (m/z 3114.39): 623.72 [M+5H]$^{5+}$, 779.39 [M+4H]$^{4+}$, 1038.86 [M+3H]$^{3+}$, 1557.78 [M+2H]$^{2+}$.

Figure 25:
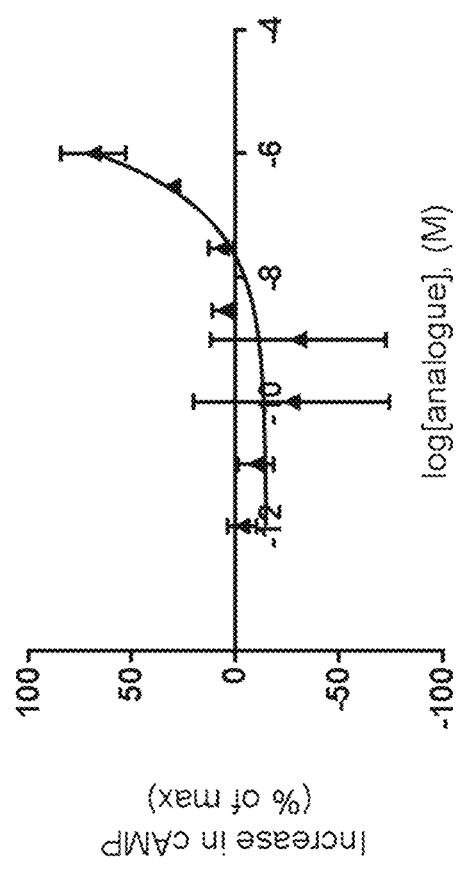
FIG. 25. Demonstrates the concentration-response curve (receptor-mediated cAMP produced) for EC50 determination of peptide-oligourea hybrid SEQ ID NO: 19 in cells expressing the GLP-1R.

FIG. 25 demonstrates the concentration-response curve (receptor-mediated cAMP produced) for EC50 determination of peptide-oligourea hybrid 19 in cells expressing the GLP-1R.

(SEQ ID NO. 20)
H-HGEGTFTSDVSSYLEGQAAKEFIAWA"A"A"RG-NH$_2$

Peptide-oligourea hybrid 20 was synthesized using the general procedure A starting from sieber resin (160 mg, 0.1 mmol). The final product 20 was purified by semi-preparative HPLC. 2.05 mg was obtained (yield 0.6%). HPLC: R$_f$=5.21 min (10-100% CH$_3$CN 0.1% TFA in H$_2$O 0.1% TFA, 10 min, C18); LC-MS (m/z 3243.55): 649.59 [M+5H]$^{5+}$, 811.73 [M+4H]$^{4+}$, 1081.95 [M+3H]$^{3+}$, 1622.41 [M+2H]$^{2+}$.

Figure 26:
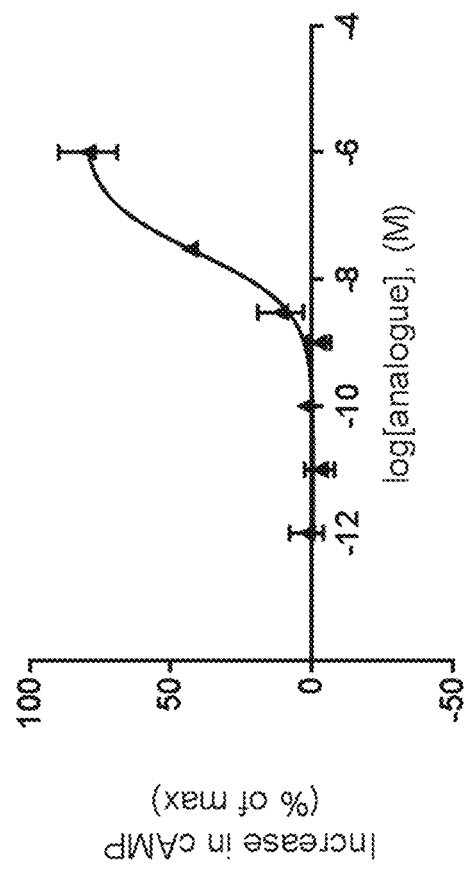
FIG. 26. Demonstrates the concentration-response curve (receptor-mediated cAMP produced) for EC50 determination peptide-oligourea hybrid SEQ ID NO: 20 in cells expressing the GLP-1R.

FIG. 26 demonstrates the concentration-response curve (receptor-mediated cAMP produced) for EC50 determination peptide-oligourea hybrid 20 in cells expressing the GLP-1R.

(SEQ ID NO. 21)
H-HGEGTFTSDVSSYLEGQAAKEFIAWLA"A"A"G-NH₂

Peptide-oligourea hybrid 21 was synthesized using the general procedure A starting from sieber resin (160 mg, 0.1 mmol). The final product 21 was purified by semi-preparative HPLC. 2.7 mg was obtained (yield 0.8%). HPLC: $R_t$=5.81 min (10-100% $CH_3CN$ 0.1% TFA in $H_2O$ 0.1% TFA, 10 min, C18); LC-MS (m/z 3200.52): 800.97 $[M+4H]^{4+}$, 1067.95 $[M+3H]^{3+}$, 1600.89 $[M+2H]^{2+}$.

Figure 27:
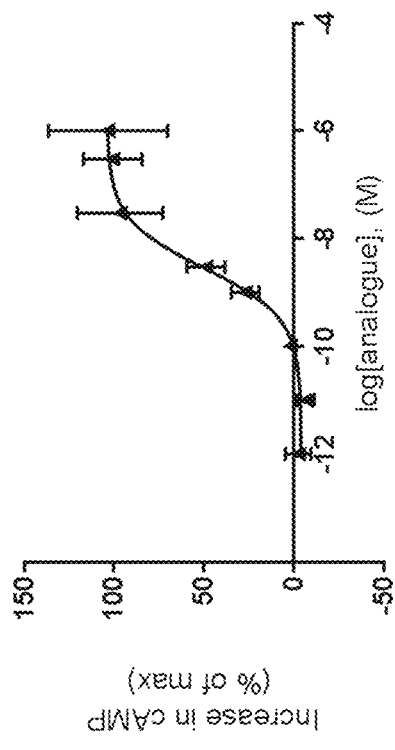
FIG. 27. Demonstrates the concentration-response curve (receptor-mediated cAMP produced) for EC50 determination of peptide-oligourea hybrid SEQ ID NO: 21 in cells expressing the GLP-1R.

FIG. 27 demonstrates the concentration-response curve (receptor-mediated cAMP produced) for EC50 determination of peptide-oligourea hybrid 21 in cells expressing the GLP-1R.

(SEQ ID NO. 22)
H-HGEGTFTSDVSSYLEGQAAKEFIAWLVA"A"A"-NH₂

Peptide-oligourea hybrid 22 was synthesized using the general procedure A starting from sieber resin (160 mg, 0.1 mmol). The final product 22 was purified by semi-preparative HPLC. 2.2 mg was obtained (yield 0.7%). HPLC: $R_t$=6.45 min (10-100% $CH_3CN$ 0.1% TFA in $H_2O$ 0.1% TFA, 10 min, C18); LC-MS (m/z 3242.60): 649.59 $[M+5H]^{5+}$, 811.48 $[M+4H]^{4+}$, 1081.63 $[M+3H]^{3+}$, 1621.91 $[M+2H]^{2+}$.

Figure 28C:
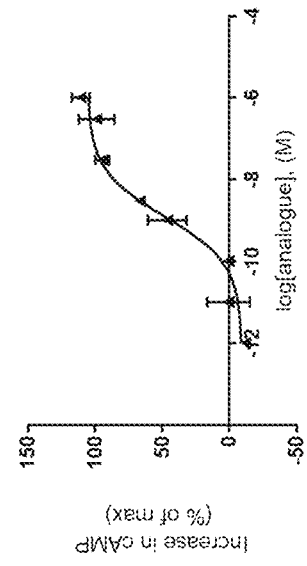
FIGS. 28A, 28B, and 28C. (28A) Demonstrates the concentration-response curve (receptor-mediated cAMP produced) for EC50 determination of peptide-oligourea SEQ ID NO: 22 in cells expressing the GLP-1R. (28B) demonstrates the enzymatic degradation of peptide-oligourea hybrid SEQ ID NO: 22 by NEP 24.11. (28C) demonstrates the muse plasma degradation of peptide-oligourea hybrid SEQ ID NO: 22.
Figure 28B:
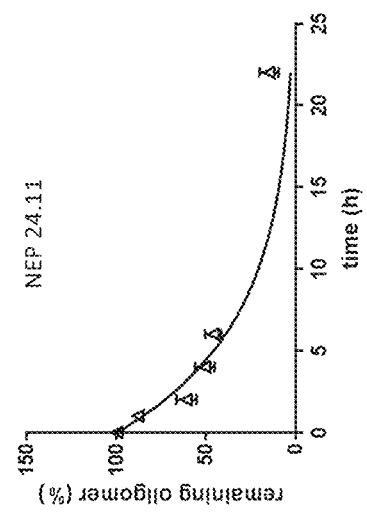
Figure 28A:
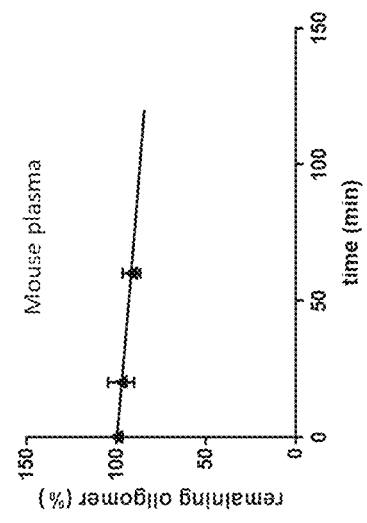

FIG. 28 demonstrates the concentration-response curve (receptor-mediated cAMP produced) for EC50 determination of peptide-oligourea 22 in cells expressing the GLP-1R (FIG. 28A). FIG. 28B demonstrates the enzymatic degradation of peptide-oligourea hybrid 22 by NEP 24.11. FIG. 28C demonstrates the muse plasma degradation of peptide-oligourea hybrid 22.

(SEQ ID NO. 23)
H-HGEGTFTSDVSSY"E"A"A"A"FIAWLVKGRG-NH₂

Peptide-oligourea hybrid 23 was synthesized using the general procedure A starting from sieber resin (160 mg, 0.1 mmol). The final product 23 was purified by semi-preparative HPLC. 5.5 mg was obtained (yield 1.7%). HPLC: $R_t$=5.57 min (10-100% $CH_3CN$ 0.1% TFA in $H_2O$ 0.1% TFA, 10 min, C18); LC-MS (m/z 3264.66): 653.69 $[M+5H]^{5+}$, 816.87 $[M+4H]^{4+}$, 1088.84 $[M+3H]^{3+}$.

Figure 29A:
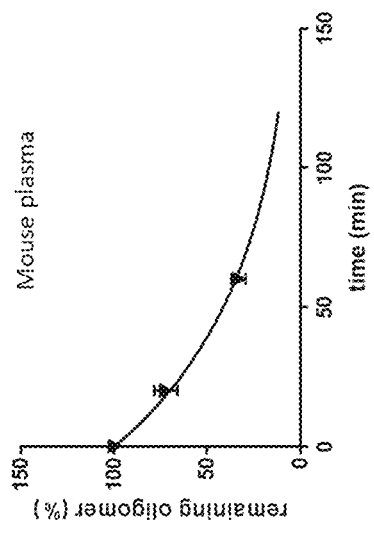
FIGS. 29A, 29B, and 29C. (29A) Demonstrates the concentration-response curve (receptor-mediated cAMP produced) for EC50 determination of peptide-oligourea hybrid SEQ ID NO: 23 in cells expressing the GLP-1R. (29B) demonstrates the enzymatic degradation of peptide-oligourea hybrid SEQ ID NO: 23 by NEP 24.11. (29C) demonstrates the mouse plasma degradation of peptide-oligourea hybrid SEQ ID NO: 23.
Figure 29B:
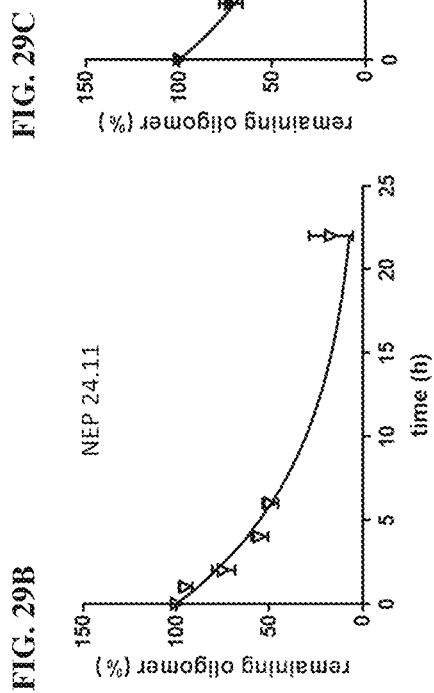
Figure 29C:
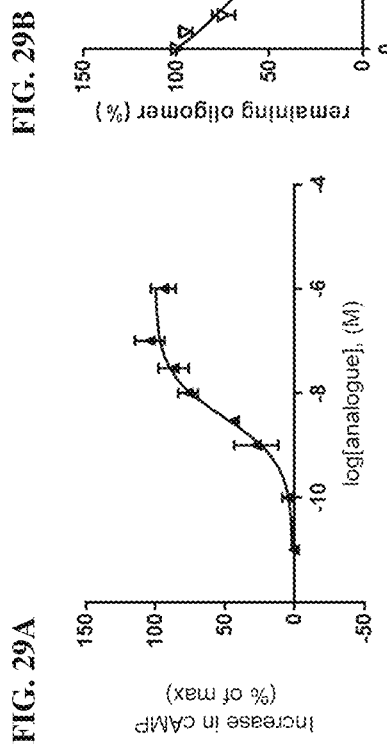

FIG. 29 demonstrates the concentration-response curve (receptor-mediated cAMP produced) for EC50 determination of peptide-oligourea hybrid 23 in cells expressing the GLP-1R (FIG. 29A). FIG. 29B demonstrates the enzymatic degradation of peptide-oligourea hybrid 23 by NEP 24.11. FIG. 29C demonstrates the mouse plasma degradation of peptide-oligourea hybrid 24.

(SEQ ID NO. 24)
H-HAibEGTFTSDVSSYLEGQAAK(2xOEG-γE-C18 diacid)
EFIAWLVA"A"A"-NH₂

2xOEG-γE-C18 diacid =

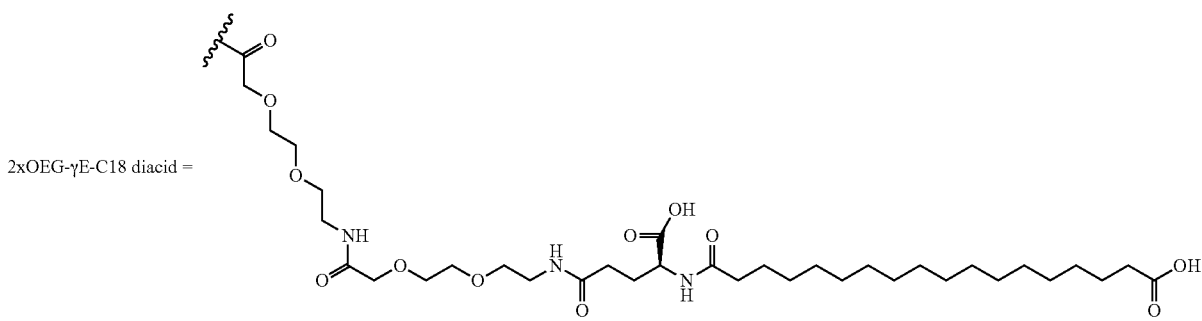 [SMILES: *C(=O)COCCOCCNC(=O)COCCOCCNC(=O)CC[C@H](NC(=O)CCCCCCCCCCCCCCCCC(=O)O)C(=O)O]

Peptide-oligourea hybrid 24 was synthesized using the general procedure B starting from rink resin (196 mg, 0.1 mmol). The final product 25 was purified by semi-preparative HPLC. 1.45 mg was obtained (yield 0.4%). HPLC: $R_t$=8.27 min (10-100% $CH_3CN$ 0.1% TFA in $H_2O$ 0.1% TFA, 10 min, C18); FC-MS (m/z 3986.54): 997.67 $[M+4H]^{4+}$, 1329.87 $[M+3H]^{3+}$, 1994.26 $[M+2H]^{2+}$.

Figure 30A:
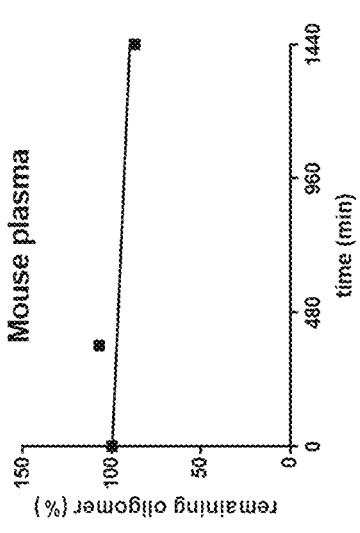
FIGS. 30A, 30B, and 30C. (30A) Demonstrates the concentration-response curve (receptor-mediated cAMP produced) for EC50 determination of peptide-oligourea hybrid SEQ ID NO: 24 in cells expressing the GLP-1R. (30B) demonstrates the enzymatic degradation of peptide-oligourea hybrid SEQ ID NO: 24 by Pancreatin. (30C) demonstrates the mouse plasma degradation of peptide-oligourea hybrid SEQ ID NO: 24.
Figure 30B:
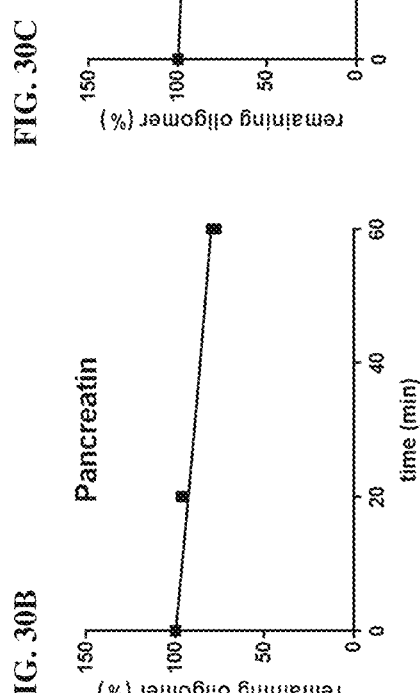
Figure 30C:
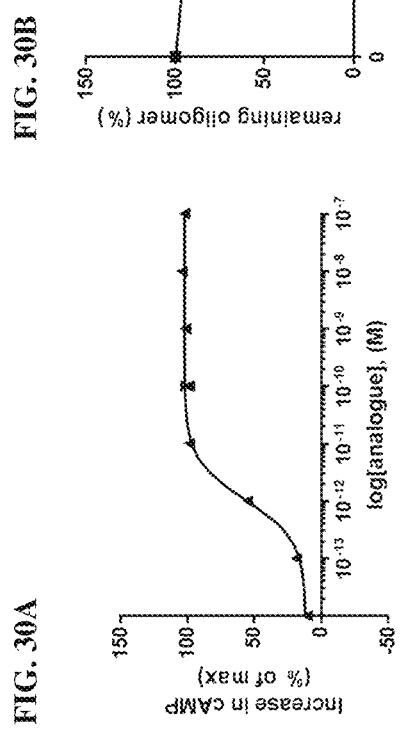

FIG. 30 demonstrates the concentration-response curve (receptor-mediated cAMP produced) for EC50 determination of peptide-oligourea hybrid 24 in cells expressing the GFP-1R (FIG. 30A). FIG. 30B demonstrates the enzymatic degradation of peptide-oligourea hybrid 24 by Pancreatin. FIG. 30C demonstrates the mouse plasma degradation of peptide-oligourea hybrid 24.

```
H-HAibEGTFTSDVSSYLEGQAAK(2xOEG-γE-C18 diacid)
EFIAWLVRGRG-OH (SEQ ID NO. 25, Semaglutide)
```

2xOEG-γE-C18 diacid =

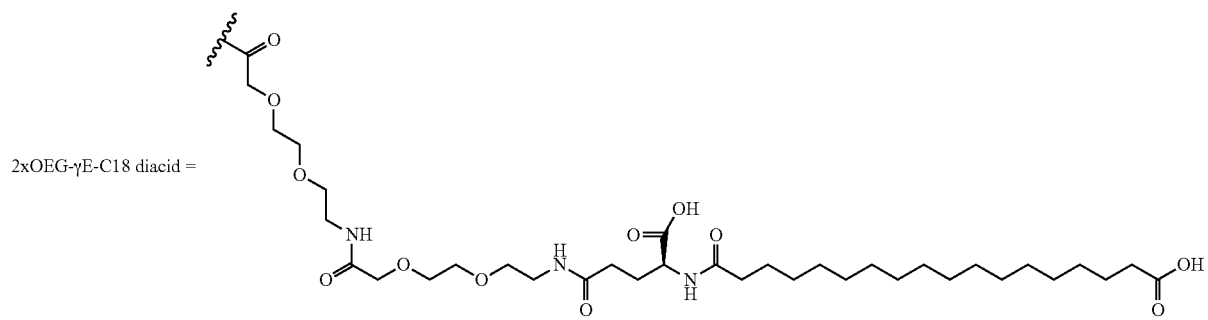 [SMILES: *C(=O)COCCOCCNC(=O)COCCOCCNC(=O)CC[C@H](NC(=O)CCCCCCCCCCCCCCCCC(=O)O)C(=O)O]

Peptide 25 was synthesized using the general procedure C starting from wang resin (220 mg, 0.1 mmol). The final product 25 was purified by semi-preparative HPLC. 2.2 mg was obtained (yield 0.5%). HPLC: $R_t$=6.13 min (10-100% $CH_3CN$ 0.1% TFA in $H_2O$ 0.1% TFA, 10 min, C18); LC-MS (m/z 4113.60): 823.76 $[M+5H]^{5+}$, 1029.44 $[M+4H]^{4+}$, 1372.22 $[M+3H]^{3+}$.

Figure 31A:
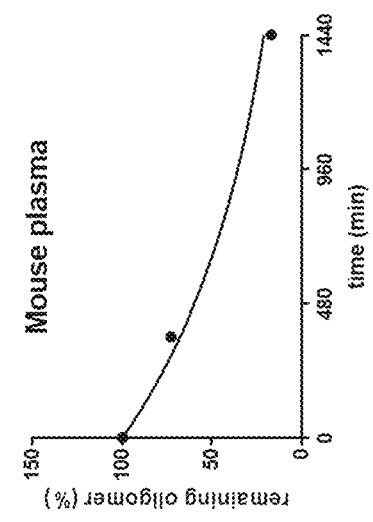
FIGS. 31A, 31B, and 31C. Demonstrates the concentration-response curve (receptor-mediated cAMP produced) for EC50 determination of peptide 25 in cells expressing the GLP-1R (31A). (31B) demonstrate the enzymatic degradation of peptide 25 by Pancreatin. (31C) demonstrates the mouse plasma degradation of peptide 25.
Figure 31B:
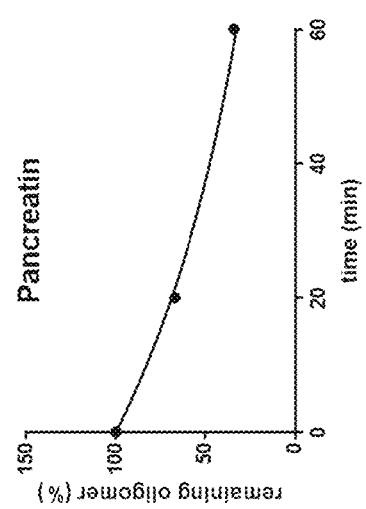
Figure 31C:
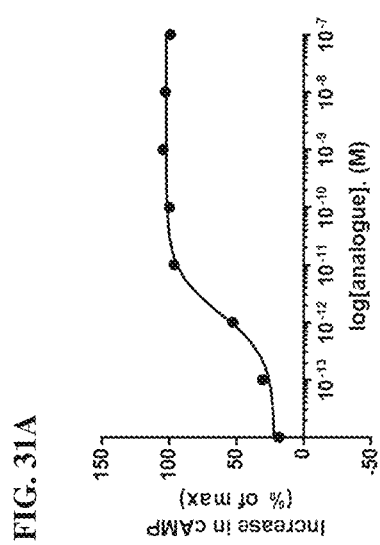

FIG. 31 demonstrates the concentration-response curve (receptor-mediated cAMP produced) for EC50 determination of peptide 26 in cells expressing the GLP-1R (FIG. 31A). FIG. 31B demonstrate the enzymatic degradation of peptide 25 by Pancreatin. FIG. 31C demonstrates the mouse plasma degradation of peptide 25.

NEP 24.11 Degradation Assay

FIG. 32 demonstrates the enzymatic degradation by NEP 24.11 of the respective peptides (SEQ ID NO: 1, 2, 5, 9, 11, 14, 16, 22, and 23). (two-way anova and Bonferroni post test: *$p<0.05$;  $p<0.01$; * $p<0.001$).

Mouse Plasma Degradation Assay

Figure 33:
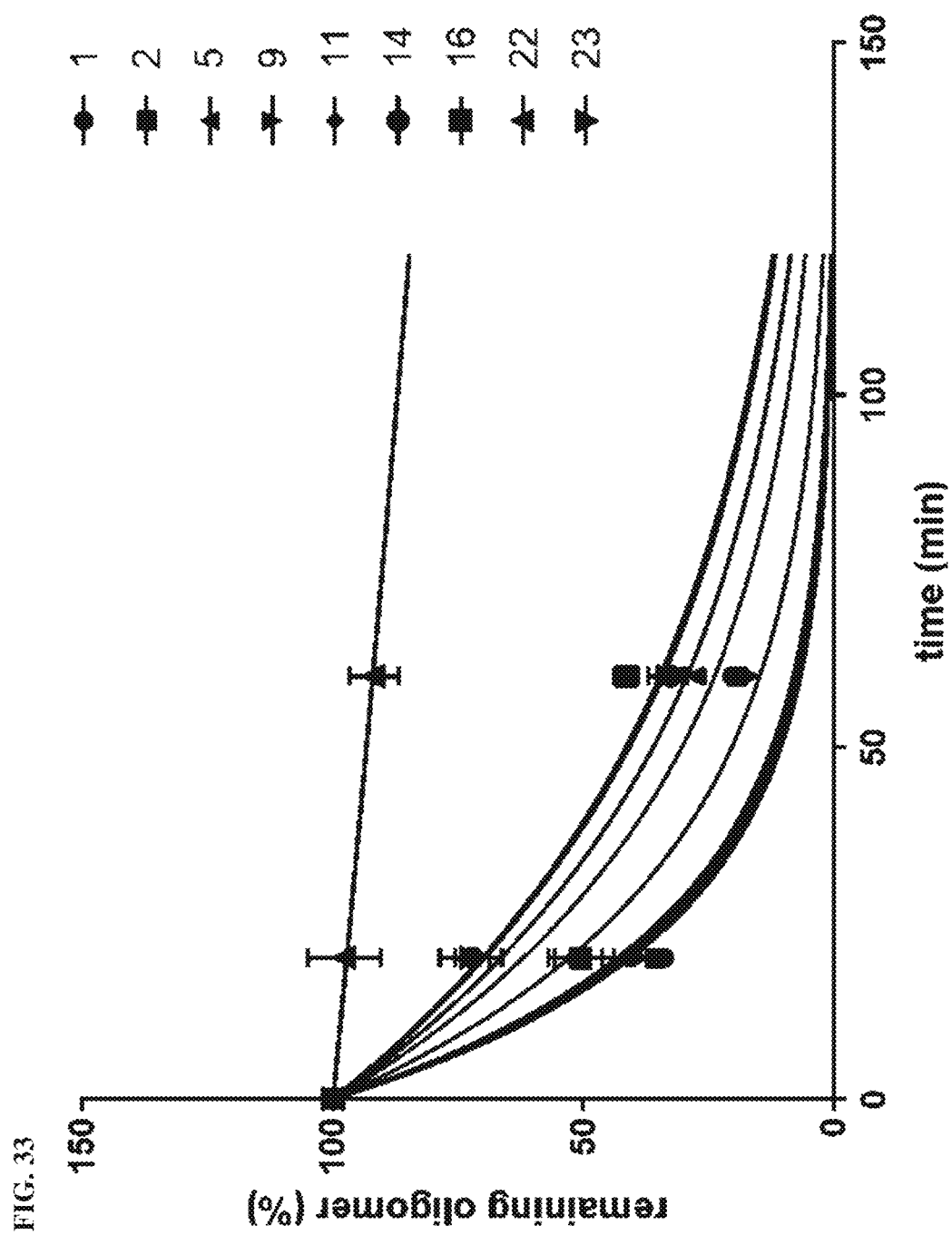
FIG. 33. Demonstrates the mouse plasma degradation of the respective peptides (SEQ ID Nos: 1, 2, 5, 9, 11, 14, 16, 22, and 23).

FIG. 33 demonstrates the mouse plasma degradation of the respective peptides (SEQ ID NO: 1, 2, 5, 9, 11, 14, 16, 22, and 23).

FIG. 34 demonstrates the mouse plasma degradation assay (two-way anova and Bonferroni post test: *$p<0.05$;  $p<0.01$; * $p<0.001$) (A); (B) Half life in pancreatin (two-way anova and Dunnett post test: *$p<0.05$;  $p<0.01$; * $p<0.001$); (C) EC50 values and standard error of the mean values.

Pancreatin Degradation Assay

FIG. 35 demonstrates the enzymatic degradation (Pancreatin) (two-way anova and Bonferroni post test: *$p<0.05$;  $p<0.01$; * $p<0.001$) (A); (B) Half life in pancreatin (two-way anova and Dunnett post test: *$p<0.05$;  $p<0.01$; * $p<0.001$); (C) EC50 values and standard error of the mean values.

IPGTT 2 h after dosing: Blood glucose measurements before the IPGTT

Figure 36:
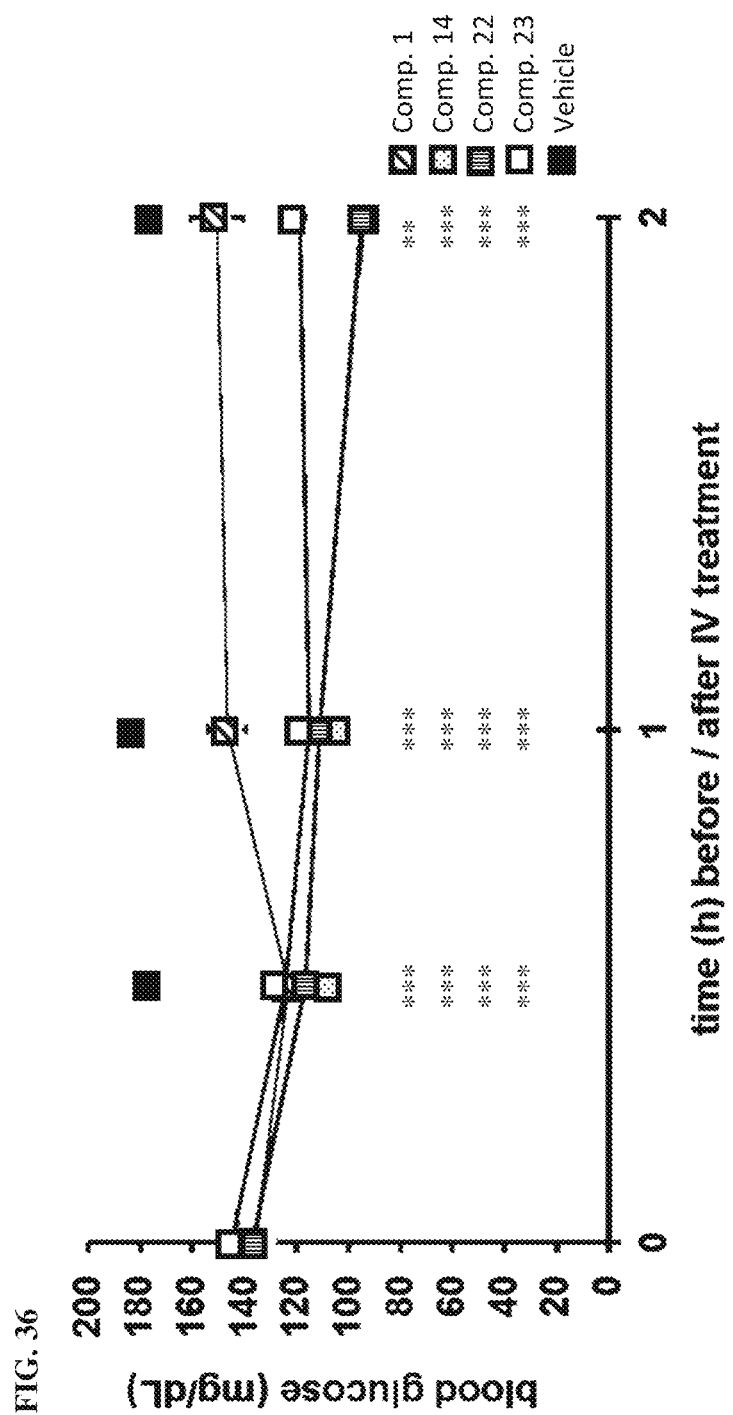
FIG. 36. Demonstrates the fasting blood glucose (mg/dL) before and after i.v treatment in mice treated with vehicle, 1, 14, 22, 23, 5 µg/mouse (two-way ANOVA and Bonferroni post-test:  $p<0.01$; * $p<0.001$).

FIG. 36 demonstrates the fasting blood glucose (mg/dL) before and after i.v treatment in mice treated with vehicle, 1, 14, 22, 23, 5 μg/mouse (two-way ANOVA and Bonferroni post-test:  $p<0,01$; * $p<0,001$).

In Vitro Pharmacology ($EC_{50}$)—Second Method

Evaluation of the agonist activity of hybrid 24 and semaglutide (25) at the human GLP-1 receptor exogenously expressed in HEK293T cells, was determined by measuring their effects on cAMP production using the HTRF detection method (performed by Ureka). The cells were suspended in cell culture media (DMEM 1×+GlutaMAX (Gibco 31966-021)) complemented with FBS 10% (Sigma Aldrich F7524), Pen/Strep 1% (Sigma Aldrich P4333) and 500 μM IBMX, then distributed in 384-well microplates at a density of $1.0×10^4$ cells/well (35 μL). Stock solutions of the compounds were prepared at a concentration of 1 mM in DMSO. Then, Compounds to be tested were diluted in assay buffer and a 35 μL aliquot transferred to the plate containing the cells to reach final assay concentrations of $1*10^{-14}$-$1*10^{-7}$ M. The plate was incubated for 15 min at 5% $CO_2$ at 37° C. Following incubation, the cells were lysed and the fluorescence acceptor (D2-labeled cAMP) and fluorescence donor (anti-cAMP antibody labeled with europium cryptate) were added. After 120 min at room temperature, the fluorescence transfer was measured at $\lambda_{ex}$=337 nm and $\lambda_{em}$=620 nm and 665 nm using a microplate reader (F500 Tecan). The cAMP concentration was determined by dividing the signal measured at 665 nm by that measured at 620 nm (ratio). The results are expressed as a percent of the control response to 10 nM Forskolin. The standard reference agonist is GFP-1-$G^2$-$NH_2$, which is tested in each experiment at several concentrations to generate a concentration-response curve from which its $EC_{50}$ value and SEM is calculated using GraphPad Prism.

FIG. 37 demonstrates the concentration-response curve (receptor-mediated cAMP produced) for EC50 determination of oligomer 24 and 25 in cells expressing the GFP-1R (A). (B) EC50 values and standard error of the mean values.

Thus, the experimental results demonstrate that peptide-oligourea chimeric foldamers (compounds having a polypeptide portion contiguous with or linked to oligomers of amino acids having an N,N'-linked urea bridging unit) demonstrate enhanced or improved properties relative to the parental or cognate "natural" peptide. Oligoureas can be derived from building blocks with any desired amino acid side chain. In particular, the chimeric compounds as described herein demonstrate regular and persistent helical conformations and improved helix stability. Because the chimeric foldamers as described herein can adopt desired secondary structures similar to native peptides, including, e.g., linear, cyclic or helicoidal structures, they can serve as, for example, receptor ligands, effector molecules, agonists, antagonists, modulators of protein-protein interactions, organocatalysts or enzymes.

```
SEQUENCES OF THE PRESENT DISCLOSURE
Compound 1
                                          (SEQ ID NO: 1)
HGEGTFTSDVSSYLEGQAAKEFIAWLVKGRG-NH2

Compound 2
                                          (SEQ ID NO: 2)
HGEGTFTSD"α"A"A"YLEGQAAKEFIAWLVKGRG-NH2

Compound 3
                                          (SEQ ID NO: 3)
HGEGTFTSDA"A"A"LEGQAAKEFIAWLVKGRG-NH2

Compound 4
                                          (SEQ ID NO: 4)
HGEGTFTSDVA"A"A"EGQAAKEFIAWLVKGRG-NH2

Compound 5
                                          (SEQ ID NO: 5)
HGEGTFTSDVA"Y"A"EGQAAKEFIAWLVKGRG-NH2

Compound 6
                                          (SEQ ID NO: 6)
HGEGTFTSDVSA"A"A"GQAAKEFIAWLVKGRG-NH2

Compound 7
                                          (SEQ ID NO: 7)
HGEGTFTSDVSSA"A"A"QAAKEFIAWLVKGRG-NH2

Compound 8
                                          (SEQ ID NO: 8)
HGEGTFTSDVSSYA"A"A"AAKEFIAWLVKGRG-NH2

Compound 9
                                          (SEQ ID NO: 9)
HGEGTFTSDVSSYY"E"A"AAKEFIAWLVKGRG-NH2

Compound 10
                                         (SEQ ID NO: 10)
HGEGTFTSDVSSYLA"A"A"AKEFIAWLVKGRG-NH2

Compound 11
                                         (SEQ ID NO: 11)
HGEGTFTSDVSSYLE"A"A"AKEFIAWLVKGRG-NH2

Compound 12
                                         (SEQ ID NO: 12)
HGEGTFTSDVSSYLEA"A"A"KEFIAWLVKGRG-NH2

Compound 13
                                         (SEQ ID NO: 13)
HGEGTFTSDVSSYLEGA"A"A"EFIAWLVKGRG-NH2

Compound 14
                                         (SEQ ID NO: 14)
HGEGTFTSDVSSYLEGQA"A"A"FIAWLVKGRG-NH2

Compound 15
                                         (SEQ ID NO: 15)
HGEGTFTSDVSSYLEGQAA"A"A"IAWLVKGRG-NH2

Compound 16
                                         (SEQ ID NO: 16)
HGEGTFTSDVSSYLEGQAAKEF"α"I"A"LVKGRG-NH2

Compound 17
                                         (SEQ ID NO: 17)
HGEGTFTSDVSSYLEGQAAKEFA"A"A"VKGRG-NH2

Compound 18
                                         (SEQ ID NO: 18)
HGEGTFTSDVSSYLEGQAAKEFIA"A"A"KGRG-NH2

Compound 19
                                         (SEQ ID NO: 19)
HGEGTFTSDVSSYLEGQAAKEFIAA"A"A"GRG-NH2

Compound 20
                                         (SEQ ID NO: 20)
HGEGTFTSDVSSYLEGQAAKEFIAWA"A"A"RG-NH2

Compound 21
                                         (SEQ ID NO: 21)
HGEGTFTSDVSSYLEGQAAKEFIAWLA"A"A"G-NH2

Compound 22
                                         (SEQ ID NO: 22)
HGEGTFTSDVSSYLEGQAAKEFIAWLVA"A"A"-NH2

Compound 23
                                         (SEQ ID NO: 23)
HGEGTFTSDVSSYY"E"A"A"A"FIAWLVKGRG-NH2

Compound 24
                                         (SEQ ID NO: 24)
HAibEGTFTSDVSSYLEGQAAK(2xOEG-γE-C18 diacid)

EFIAWLVA"A"A"

Compound 25
                                         (SEQ ID NO: 25)
HAibEGTFTSDVSSYLEGQAAK(2xOEG-γE-C18diacid)

EFIAWLVRGRG-OH (semaglutide)

Compound 26
                                         (SEQ ID NO: 26)
HGEGTFTSDVSSYLEGQAAKEFIAWLVKGRG-OH(GLP-1)
```

While preferred embodiments of the disclosure have been shown and described herein, it will be understood that such embodiments are provided by way of example only. Numerous variations, changes and substitutions will occur to those skilled in the art without departing from the spirit of the disclosure. Accordingly, it is intended that the appended claims cover all such variations as fall within the spirit and scope of the disclosure.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the disclosure described herein. Such equivalents are intended to be encompassed by the following claims. It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:

1. A glucagon-like peptide-1 (GLP-1) peptide-oligourea hybrid foldamer comprising a GLP-1 peptide wherein four consecutive amino acid residues are replaced with three consecutive oligourea residues of formula (II) or eight consecutive amino acid residues are replaced with six consecutive oligourea residues of formula (II):

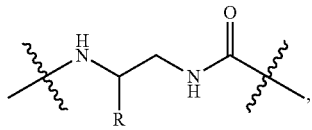

(II)

wherein R is a proteinogenic amino acid side chain selected from alanine and a side chain at the corresponding position in the GLP-1 peptide.

2. The peptide-oligourea hybrid of claim 1, wherein the GLP-1 peptide-oligourea hybrid demonstrates a resistance to dipeptidyl peptidase-4 (DPP-4) in PBS or in serum that is greater than native or naturally occurring GLP-1.

3. The peptide-oligourea hybrid of claim 1, wherein the GLP-1 peptide-oligourea hybrid demonstrates a resistance to neutral endopeptidase 24.11 (NEP 24.11) in PBS or in serum that is greater than native or naturally occurring GLP-1.

4. The peptide-oligourea hybrid of claim 1, wherein the GLP-1 peptide-oligourea hybrid demonstrates an EC50 of less than about 10 μM.

5. The peptide-oligourea hybrid of claim 1, wherein the GLP-1 peptide-oligourea hybrid demonstrates binding to GLP-1 receptor (GLP-1R).

6. The peptide-oligourea hybrid of claim 1, wherein the GLP-1 peptide-oligourea hybrid demonstrates bioactivity in a cAMP production assay.

7. A peptide-oligourea hybrid selected from the group consisting of at least one sequence of SEQ ID NO: 2-24.

8. A peptide-oligourea hybrid selected from the group of SEQ ID NO: 5, 9, 11, 14, 16, 22, 23, and 24.

9. A pharmaceutical formulation comprising a GLP-1 peptide-oligourea hybrid of claim 1, and a pharmaceutically acceptable excipient.

10. A method of treating a metabolic disorder, comprising administering to a subject in need thereof a composition comprising an effective amount of a GLP-1 peptide-oligourea hybrid of claim 1, wherein composition is effective at ameliorating at least one symptom or treating the metabolic disorder.

11. The method of claim 10, wherein the disease is diabetes.

* * * * *